United States Patent
Collins, Jr. et al.

(10) Patent No.: US 8,012,136 B2
(45) Date of Patent: *Sep. 6, 2011

(54) OPHTHALMIC FLUID DELIVERY DEVICE AND METHOD OF OPERATION

(75) Inventors: James F. Collins, Jr., Long Island City, NY (US); Michael Joseph Jobin, Boston, MA (US); Alexander Kirby Tee, Somerville, MA (US)

(73) Assignee: Optimyst Systems, Inc., West Islip, NY (US)

(*) Notice: Subject to any disclaimer, the term of this patent is extended or adjusted under 35 U.S.C. 154(b) by 684 days.

This patent is subject to a terminal disclaimer.

(21) Appl. No.: 11/698,438

(22) Filed: Jan. 26, 2007

(65) Prior Publication Data

US 2007/0119968 A1    May 31, 2007

Related U.S. Application Data

(63) Continuation-in-part of application No. 10/851,611, filed on May 20, 2004, now Pat. No. 7,883,031.

(60) Provisional application No. 60/471,883, filed on May 20, 2003, provisional application No. 60/485,305, filed on Jul. 3, 2003.

(51) Int. Cl.
    *A61M 35/00* (2006.01)
(52) U.S. Cl. ........................................ 604/298; 604/294
(58) Field of Classification Search ........... 604/294–300
    See application file for complete search history.

(56) References Cited

U.S. PATENT DOCUMENTS

| 429,407 A | 6/1890 | Reichi et al. |
| 772,028 A | 10/1904 | Carpenter |
| 1,482,747 A * | 2/1924 | Howe ........................... 239/351 |
| 1,988,637 A | 1/1935 | Tinkham |
| 2,189,643 A | 2/1940 | Ward |

(Continued)

FOREIGN PATENT DOCUMENTS

DE    199 34 582    1/2001

(Continued)

OTHER PUBLICATIONS

European Supplementary Search Report for European Application No. EP 04 75 3072 mailed on Feb. 27, 2009.

(Continued)

*Primary Examiner* — Tatyana Zalukaeva
*Assistant Examiner* — Paula L Craig
(74) *Attorney, Agent, or Firm* — Brinks Hofer Gilson & Lione

(57) ABSTRACT

The present invention provides an ophthalmic fluid delivery device adapted to deliver an ophthalmic fluid in the form of a mist to an ocular region of a patient. The ophthalmic fluid delivery device comprises a nozzle defining an aperture through which the ophthalmic fluid can flow and at least one shutter positioned proximate to the aperture of the nozzle. The shutter is mounted for movement with respect to the aperture of the nozzle between an open position permitting flow of the ophthalmic fluid through the aperture of the nozzle and a closed position at least partially covering the aperture. A shutter actuator is positioned proximate to the shutter. The shutter actuator is mounted for movement with respect to the nozzle, and the shutter actuator is coupled to the shutter such that the movement of the shutter actuator moves the shutter between the open position and the closed position.

12 Claims, 44 Drawing Sheets

U.S. PATENT DOCUMENTS

| | | | |
|---|---|---|---|
| 2,200,008 A | 5/1940 | Nowak | |
| 2,249,608 A | 7/1941 | Greene | |
| 2,322,808 A | 6/1943 | Hothersall | |
| 2,552,857 A | 5/1951 | Knapp | |
| 2,595,317 A | 5/1952 | White, Jr. | |
| 2,987,439 A * | 6/1961 | Wittlinger | 424/45 |
| 3,170,462 A | 2/1965 | Hall | |
| 3,187,757 A | 6/1965 | Jones, Jr. et al. | |
| 3,237,809 A | 3/1966 | Daragan et al. | |
| 3,310,830 A * | 3/1967 | Gattone | 401/190 |
| 3,314,426 A | 4/1967 | Carroll | |
| 3,439,674 A | 4/1969 | Lelicoff | |
| 3,602,399 A | 8/1971 | Litman et al. | |
| 3,658,257 A | 4/1972 | Rood | |
| 3,709,235 A | 1/1973 | Washburn et al. | |
| 3,779,245 A | 12/1973 | Windsor | |
| 3,780,950 A | 12/1973 | Brennan | |
| 3,795,351 A | 3/1974 | Lehmann | |
| 3,812,854 A | 5/1974 | Michaels et al. | |
| 3,826,258 A | 7/1974 | Abraham | |
| 3,845,764 A | 11/1974 | Windsor | |
| 3,901,443 A | 8/1975 | Mitsui et al. | |
| 3,906,949 A | 9/1975 | Holland | |
| 3,913,575 A | 10/1975 | Windsor | |
| 3,934,585 A | 1/1976 | Maurice | |
| 4,002,168 A | 1/1977 | Petterson | |
| 4,052,985 A | 10/1977 | Coleman et al. | |
| 4,067,499 A | 1/1978 | Cohen | |
| 4,098,431 A | 7/1978 | Palmer et al. | |
| D249,709 S | 9/1978 | Trovinger | |
| 4,119,096 A | 10/1978 | Drews | |
| 4,122,556 A | 10/1978 | Poler | |
| 4,131,115 A | 12/1978 | Peng | |
| 4,173,226 A | 11/1979 | Shell | |
| 4,175,704 A | 11/1979 | Cohen | |
| 4,175,706 A | 11/1979 | Gerstmann | |
| 4,264,837 A | 4/1981 | Gaboriaud | |
| 4,296,071 A | 10/1981 | Weiss et al. | |
| 4,319,155 A | 3/1982 | Nakai et al. | |
| 4,323,530 A | 4/1982 | Voss et al. | |
| 4,338,936 A | 7/1982 | Nelson | |
| 4,356,528 A | 10/1982 | Coffee | |
| 4,381,533 A | 4/1983 | Coffee | |
| 4,390,542 A | 6/1983 | Schachar | |
| 4,398,909 A | 8/1983 | Portnoff | |
| 4,465,234 A | 8/1984 | Maehara et al. | |
| 4,471,890 A | 9/1984 | Dougherty | |
| 4,476,515 A | 10/1984 | Coffee | |
| 4,479,609 A | 10/1984 | Maeda et al. | |
| 4,493,119 A | 1/1985 | Baumann | |
| 4,543,096 A | 9/1985 | Keene | |
| 4,544,570 A | 10/1985 | Plunkett et al. | |
| 4,564,016 A | 1/1986 | Maurice et al. | |
| 4,580,721 A | 4/1986 | Coffee et al. | |
| 4,605,167 A | 8/1986 | Maehara | |
| 4,605,398 A | 8/1986 | Herrick | |
| 4,627,845 A | 12/1986 | DeMotte | |
| 4,641,384 A | 2/1987 | Landsberger et al. | |
| 4,642,581 A | 2/1987 | Erickson | |
| 4,658,290 A | 4/1987 | McKenna | |
| 4,659,014 A | 4/1987 | Soth et al. | |
| 4,679,551 A | 7/1987 | Anthony | |
| 4,685,906 A | 8/1987 | Murphy | |
| 4,701,167 A | 10/1987 | Chekan | |
| 4,702,418 A | 10/1987 | Carter et al. | |
| 4,706,848 A | 11/1987 | D'Andrade | |
| 4,740,206 A | 4/1988 | Allander | |
| 4,742,713 A | 5/1988 | Abe et al. | |
| 4,750,650 A | 6/1988 | Ling | |
| 4,750,902 A | 6/1988 | Wuchinich et al. | |
| 4,758,237 A * | 7/1988 | Sacks | 604/294 |
| 4,758,727 A | 7/1988 | Tomei et al. | |
| 4,759,755 A | 7/1988 | Hein et al. | |
| 4,779,768 A | 10/1988 | St. Amand | |
| 4,784,652 A | 11/1988 | Wikstrom | |
| 4,790,479 A | 12/1988 | Matsumoto et al. | |
| 4,792,334 A | 12/1988 | Py | |
| 4,793,339 A | 12/1988 | Matsumoto et al. | |
| 4,796,807 A | 1/1989 | Bendig et al. | |
| 4,798,599 A | 1/1989 | Thomas | |
| 4,809,914 A * | 3/1989 | Goncalves | 239/327 |
| 4,815,661 A | 3/1989 | Anthony | |
| 4,826,025 A | 5/1989 | Abiko et al. | |
| 4,850,534 A | 7/1989 | Takahashi et al. | |
| 4,863,073 A | 9/1989 | Burt et al. | |
| 4,863,443 A | 9/1989 | Hornung | |
| 4,863,457 A | 9/1989 | Lee | |
| 4,871,091 A | 10/1989 | Preziosi | |
| 4,877,989 A | 10/1989 | Drews et al. | |
| 4,880,146 A | 11/1989 | Hudgins | |
| 4,881,283 A | 11/1989 | Liautaud | |
| 4,886,189 A | 12/1989 | Vanderjagt | |
| 4,896,832 A * | 1/1990 | Howlett | 239/322 |
| 4,908,024 A | 3/1990 | Py | |
| 4,912,357 A | 3/1990 | Drews et al. | |
| 4,917,274 A | 4/1990 | Asa et al. | |
| 4,927,062 A | 5/1990 | Walsh | |
| 4,927,115 A | 5/1990 | Bahroos et al. | |
| 4,946,452 A | 8/1990 | Py | |
| 4,952,212 A | 8/1990 | Booth et al. | |
| 4,961,885 A | 10/1990 | Avrahami et al. | |
| 4,969,869 A | 11/1990 | Burgin et al. | |
| 4,981,479 A | 1/1991 | Py | |
| 4,996,502 A | 2/1991 | Endo | |
| 5,007,905 A | 4/1991 | Bauer | |
| 5,019,037 A | 5/1991 | Wang et al. | |
| 5,029,579 A | 7/1991 | Trammell | |
| 5,030,214 A | 7/1991 | Spector | |
| 5,032,111 A | 7/1991 | Morris et al. | |
| 5,037,012 A | 8/1991 | Langford | |
| 5,040,706 A | 8/1991 | Davis et al. | |
| 5,047,009 A | 9/1991 | Morris et al. | |
| 5,048,727 A | 9/1991 | Vlasich | |
| 5,053,000 A | 10/1991 | Booth et al. | |
| 5,054,477 A | 10/1991 | Terada et al. | |
| 5,064,420 A | 11/1991 | Clarke et al. | |
| 5,066,276 A | 11/1991 | Wang | |
| 5,069,675 A | 12/1991 | Menchel et al. | |
| 5,085,651 A | 2/1992 | Py | |
| 5,098,375 A | 3/1992 | Baier | |
| 5,133,702 A | 7/1992 | Py | |
| 5,134,993 A | 8/1992 | van der Linden et al. | |
| 5,139,496 A | 8/1992 | Hed | |
| 5,145,113 A | 9/1992 | Burwell et al. | |
| 5,152,435 A * | 10/1992 | Stand et al. | 222/309 |
| 5,152,456 A | 10/1992 | Ross et al. | |
| 5,163,929 A | 11/1992 | Py | |
| 5,164,740 A | 11/1992 | Ivri | |
| 5,170,782 A | 12/1992 | Kocinski | |
| 5,176,856 A | 1/1993 | Takahashi et al. | |
| 5,193,745 A | 3/1993 | Holm | |
| 5,201,726 A | 4/1993 | Kirkham | |
| 5,203,506 A | 4/1993 | Gross et al. | |
| 5,226,538 A | 7/1993 | Roselle | |
| 5,259,385 A | 11/1993 | Miller et al. | |
| 5,261,601 A | 11/1993 | Ross et al. | |
| 5,267,986 A | 12/1993 | Py | |
| 5,276,867 A | 1/1994 | Kenley et al. | |
| 5,299,739 A | 4/1994 | Takahashi et al. | |
| 5,316,159 A | 5/1994 | Douglas et al. | |
| 5,318,014 A | 6/1994 | Carter | |
| 5,320,845 A | 6/1994 | Py | |
| 5,346,132 A * | 9/1994 | Hahn et al. | 239/71 |
| 5,354,032 A | 10/1994 | Sims et al. | |
| 5,364,405 A | 11/1994 | Zaleski | |
| 5,368,582 A | 11/1994 | Bertera | |
| 5,401,259 A | 3/1995 | Py | |
| 5,405,614 A | 4/1995 | D'Angelo et al. | |
| 5,431,663 A | 7/1995 | Carter | |
| 5,435,282 A | 7/1995 | Haber et al. | |
| 5,435,465 A * | 7/1995 | El-Amin | 222/108 |
| 5,462,586 A | 10/1995 | Sugiyama et al. | |
| 5,485,828 A | 1/1996 | Hauser | |
| 5,496,411 A | 3/1996 | Candy | |
| 5,499,751 A | 3/1996 | Meyer | |
| D368,774 S | 4/1996 | Py | |
| 5,515,841 A | 5/1996 | Robertson et al. | |

| | | | | | | |
|---|---|---|---|---|---|---|
| 5,515,842 | A | 5/1996 | Ramseyer et al. | 6,569,131 | B1 | 5/2003 | Michael et al. |
| 5,518,179 | A | 5/1996 | Humberstone et al. | 6,569,387 | B1 * | 5/2003 | Furner et al. ............... 422/123 |
| 5,529,055 | A | 6/1996 | Gueret | 6,601,581 | B1 | 8/2003 | Babaev |
| D374,719 | S | 10/1996 | Py | 6,610,033 | B1 | 8/2003 | Melanson et al. |
| 5,584,823 | A * | 12/1996 | Valberg ..................... 604/294 | 6,612,302 | B1 | 9/2003 | Rand |
| 5,586,550 | A | 12/1996 | Ivri et al. | 6,615,824 | B2 | 9/2003 | Power |
| 5,588,564 | A | 12/1996 | Hutson et al. | 6,619,562 | B2 | 9/2003 | Hamaguchi et al. |
| 5,607,410 | A | 3/1997 | Branch | 6,622,720 | B2 | 9/2003 | Hadimioglu |
| 5,613,957 | A | 3/1997 | Py | 6,629,646 | B1 | 10/2003 | Ivri |
| 5,614,545 | A | 3/1997 | Martin et al. | 6,640,804 | B2 | 11/2003 | Ivri et al. |
| 5,630,793 | A | 5/1997 | Rowe | 6,650,935 | B1 | 11/2003 | Watmough |
| 5,641,004 | A | 6/1997 | Py | 6,651,650 | B1 | 11/2003 | Yamamoto et al. |
| 5,657,926 | A | 8/1997 | Toda | 6,659,364 | B1 | 12/2003 | Humberstone et al. |
| 5,665,079 | A | 9/1997 | Stahl | 6,669,961 | B2 | 12/2003 | Kim et al. |
| 5,685,869 | A | 11/1997 | Py | 6,676,034 | B2 | 1/2004 | Tanaka et al. |
| 5,687,874 | A | 11/1997 | Omori et al. | 6,679,436 | B1 | 1/2004 | Onishi et al. |
| 5,707,636 | A | 1/1998 | Rodriguez et al. | 6,684,681 | B1 | 2/2004 | Zombo |
| 5,724,021 | A | 3/1998 | Perrone | 6,684,879 | B1 | 2/2004 | Coffee et al. |
| 5,730,723 | A | 3/1998 | Castellano et al. | 6,719,770 | B2 | 4/2004 | Laufer et al. |
| 5,735,811 | A | 4/1998 | Brisken | 6,732,944 | B2 | 5/2004 | Litherland et al. |
| 5,740,947 | A | 4/1998 | Flaig et al. | 6,736,904 | B2 | 5/2004 | Poniatowski et al. |
| 5,746,728 | A | 5/1998 | Py | 6,748,944 | B1 | 6/2004 | Della Vecchia et al. |
| 5,758,637 | A | 6/1998 | Ivri et al. | 6,761,286 | B2 | 7/2004 | Py et al. |
| 5,803,106 | A | 9/1998 | Cohen et al. | 6,789,741 | B2 | 9/2004 | Varanasi et al. |
| 5,807,357 | A | 9/1998 | Kang | 6,814,071 | B2 | 11/2004 | Klimowicz et al. |
| 5,823,428 | A | 10/1998 | Humberstone et al. | 6,851,626 | B2 | 2/2005 | Patel et al. |
| 5,838,350 | A | 11/1998 | Newcombe et al. | 6,854,662 | B2 | 2/2005 | Chen |
| 5,843,109 | A | 12/1998 | Mehta et al. | 6,863,224 | B2 | 3/2005 | Terada et al. |
| 5,855,322 | A | 1/1999 | Py | 6,877,642 | B1 | 4/2005 | Maddox et al. |
| 5,893,515 | A | 4/1999 | Hahn et al. | 6,901,926 | B2 | 6/2005 | Yamamoto et al. |
| 5,894,841 | A | 4/1999 | Voges | 6,913,205 | B2 | 7/2005 | Cornet et al. |
| 5,938,117 | A | 8/1999 | Ivri | 6,921,020 | B2 | 7/2005 | Ivri |
| D413,668 | S | 9/1999 | Mannberg et al. | 6,926,208 | B2 | 8/2005 | Ivri |
| 5,957,943 | A | 9/1999 | Vaitekunas | 6,946,117 | B1 | 9/2005 | Schutt et al. |
| 5,970,974 | A | 10/1999 | Van Der Linden et al. | 6,964,647 | B1 | 11/2005 | Babaev |
| 5,996,903 | A | 12/1999 | Asai et al. | 6,969,165 | B2 | 11/2005 | Olsen |
| 5,997,518 | A * | 12/1999 | Laibovitz et al. ............. 604/296 | 6,974,450 | B2 | 12/2005 | Weber et al. |
| 6,008,468 | A | 12/1999 | Tanaka et al. | 6,976,279 | B1 | 12/2005 | Berke et al. |
| 6,027,450 | A | 2/2000 | Brown et al. | 6,976,969 | B2 | 12/2005 | Messerly |
| 6,039,565 | A | 3/2000 | Chou et al. | 6,978,945 | B2 | 12/2005 | Wong et al. |
| 6,062,212 | A | 5/2000 | Davison et al. | 7,017,573 | B1 | 3/2006 | Rasor et al. |
| 6,083,922 | A | 7/2000 | Montgomery | 7,032,590 | B2 | 4/2006 | Loeffler et al. |
| 6,085,740 | A | 7/2000 | Ivri et al. | 7,040,549 | B2 | 5/2006 | Ivri et al. |
| 6,135,427 | A | 10/2000 | Tsai | 7,066,398 | B2 | 6/2006 | Borland et al. |
| 6,152,383 | A | 11/2000 | Chen | 7,081,757 | B2 | 7/2006 | Unsworth et al. |
| 6,159,188 | A | 12/2000 | Laibovitz et al. | 7,083,112 | B2 | 8/2006 | Ivri |
| 6,193,683 | B1 | 2/2001 | Ludin et al. | 7,104,463 | B2 | 9/2006 | Litherland et al. |
| 6,221,038 | B1 | 4/2001 | Brisken | 7,108,197 | B2 | 9/2006 | Ivri |
| 6,228,046 | B1 | 5/2001 | Brisken | 7,121,275 | B2 | 10/2006 | Noolandi et al. |
| 6,235,024 | B1 | 5/2001 | Tu | D533,658 | S | 12/2006 | Collins, Jr. et al. |
| 6,254,579 | B1 | 7/2001 | Cogger et al. | 7,153,315 | B2 | 12/2006 | Miller |
| 6,254,587 | B1 | 7/2001 | Christ et al. | 7,161,269 | B2 | 1/2007 | Kayama et al. |
| 6,263,872 | B1 | 7/2001 | Schuster et al. | 7,168,633 | B2 | 1/2007 | Wang et al. |
| 6,273,342 | B1 | 8/2001 | Terada et al. | D537,160 | S | 2/2007 | Lowell |
| 6,296,626 | B1 | 10/2001 | Stein | 7,174,888 | B2 | 2/2007 | Ivri et al. |
| 6,336,917 | B1 | 1/2002 | Berke | 7,201,732 | B2 * | 4/2007 | Anderson et al. ............... 604/66 |
| 6,341,732 | B1 | 1/2002 | Martin et al. | 7,204,820 | B2 | 4/2007 | Akahoshi et al. |
| 6,357,671 | B1 | 3/2002 | Cewers | 7,229,028 | B2 | 6/2007 | Chen et al. |
| 6,367,685 | B1 | 4/2002 | Jiang et al. | 7,234,460 | B2 | 6/2007 | Greenleaf et al. |
| 6,387,671 | B1 | 5/2002 | Rubinsky et al. | 7,314,187 | B2 | 1/2008 | Hochrainer et al. |
| 6,394,363 | B1 | 5/2002 | Arnott et al. | 7,316,067 | B2 | 1/2008 | Blakey |
| 6,398,737 | B2 | 6/2002 | Moore et al. | 7,331,339 | B2 | 2/2008 | Smith et al. |
| 6,398,766 | B1 * | 6/2002 | Branch ........................ 604/302 | 7,357,133 | B2 | 4/2008 | Goodchild |
| 6,423,040 | B1 * | 7/2002 | Benktzon et al. ............. 604/300 | 7,472,701 | B2 | 1/2009 | Pfichner et al. |
| 6,425,888 | B1 | 7/2002 | Embleton et al. | 7,527,613 | B2 * | 5/2009 | Gaynes ..................... 604/295 |
| 6,427,682 | B1 | 8/2002 | Klimowicz et al. | D597,206 | S | 7/2009 | Collins, Jr. et al. |
| 6,442,423 | B1 | 8/2002 | Domb et al. | 7,712,466 | B2 | 5/2010 | Addington et al. |
| 6,467,476 | B1 | 10/2002 | Ivri et al. | 7,883,031 | B2 | 2/2011 | Collins, Jr. et al. |
| 6,471,095 | B1 * | 10/2002 | Cann .......................... 222/190 | 2001/0010338 | A1 * | 8/2001 | Ganan-Calvo ................... 239/8 |
| 6,524,287 | B1 * | 2/2003 | Cogger ....................... 604/298 | 2001/0025190 | A1 | 9/2001 | Weber et al. |
| 6,526,976 | B1 | 3/2003 | Baran | 2001/0049608 | A1 | 12/2001 | Hochman |
| 6,530,370 | B1 | 3/2003 | Heinonen | 2001/0056258 | A1 | 12/2001 | Evans |
| 6,540,153 | B1 | 4/2003 | Ivri | 2002/0016576 | A1 | 2/2002 | Lee |
| 6,540,154 | B1 | 4/2003 | Ivri et al. | 2002/0039502 | A1 | 4/2002 | Matsumoto et al. |
| 6,543,443 | B1 | 4/2003 | Klimowicz et al. | 2002/0043262 | A1 * | 4/2002 | Langford et al. ........ 128/200.23 |
| 6,546,927 | B2 | 4/2003 | Litherland et al. | 2002/0073989 | A1 | 6/2002 | Hadimioglu |
| 6,550,472 | B2 | 4/2003 | Litherland et al. | 2002/0074362 | A1 | 6/2002 | Py et al. |
| 6,554,201 | B2 | 4/2003 | Klimowicz et al. | 2002/0107492 | A1 * | 8/2002 | Brach et al. ..................... 604/296 |
| 6,554,801 | B1 | 4/2003 | Steward et al. | 2002/0121285 | A1 | 9/2002 | Poniatowski et al. |

| | | | |
|---|---|---|---|
| 2002/0124843 A1 | 9/2002 | Skiba et al. | |
| 2002/0161344 A1 | 10/2002 | Peclat et al. | |
| 2003/0032930 A1* | 2/2003 | Branch | 604/298 |
| 2003/0078551 A1* | 4/2003 | Hochrainer et al. | 604/295 |
| 2003/0114901 A1 | 6/2003 | Loeb et al. | |
| 2003/0144594 A1 | 7/2003 | Gellman | |
| 2003/0185892 A1 | 10/2003 | Bell et al. | |
| 2003/0192532 A1 | 10/2003 | Hopkins | |
| 2004/0010239 A1 | 1/2004 | Hochrainer et al. | |
| 2004/0045547 A1 | 3/2004 | Yamamoto et al. | |
| 2004/0050953 A1 | 3/2004 | Terada et al. | |
| 2004/0082884 A1 | 4/2004 | Pal et al. | |
| 2004/0164099 A1 | 8/2004 | Diestelhorst et al. | |
| 2004/0176757 A1 | 9/2004 | Sinelnikov et al. | |
| 2004/0186384 A1 | 9/2004 | Babaev | |
| 2004/0256487 A1* | 12/2004 | Collins et al. | 239/338 |
| 2005/0029307 A1 | 2/2005 | Py et al. | |
| 2005/0077315 A1 | 4/2005 | Pavlu et al. | |
| 2005/0077392 A1 | 4/2005 | Geser et al. | |
| 2005/0089545 A1 | 4/2005 | Kuwano et al. | |
| 2005/0195598 A1 | 9/2005 | Dancs et al. | |
| 2005/0199236 A1 | 9/2005 | Fink et al. | |
| 2005/0240162 A1* | 10/2005 | Chen et al. | 604/298 |
| 2005/0244339 A1 | 11/2005 | Jauernig et al. | |
| 2005/0261641 A1 | 11/2005 | Warchol et al. | |
| 2005/0263608 A1 | 12/2005 | Ivri | |
| 2005/0275310 A1 | 12/2005 | Ripoll | |
| 2005/0279350 A1 | 12/2005 | Rasor et al. | |
| 2006/0024374 A1 | 2/2006 | Gasco et al. | |
| 2006/0057216 A1 | 3/2006 | Salamone et al. | |
| 2006/0196518 A1 | 9/2006 | Hon | |
| 2006/0201501 A1 | 9/2006 | Morrison et al. | |
| 2006/0213503 A1 | 9/2006 | Borgschulte et al. | |
| 2006/0258993 A1 | 11/2006 | Hochrainer et al. | |
| 2007/0023547 A1 | 2/2007 | Borland et al. | |
| 2007/0119968 A1 | 5/2007 | Collins, Jr. et al. | |
| 2007/0119969 A1* | 5/2007 | Collins et al. | 239/102.1 |
| 2008/0097359 A1 | 4/2008 | Hochrainer et al. | |
| 2008/0142624 A1 | 6/2008 | Ivri | |
| 2008/0164339 A1 | 7/2008 | Duru | |
| 2008/0299049 A1 | 12/2008 | Stangl | |
| 2008/0308096 A1 | 12/2008 | Borgschulte et al. | |
| 2009/0025713 A1 | 1/2009 | Keller et al. | |
| 2009/0114742 A1* | 5/2009 | Collins, Jr. | 239/338 |
| 2009/0149829 A1* | 6/2009 | Collins, Jr. | 604/500 |
| 2009/0182291 A1* | 7/2009 | Eilat | 604/290 |
| 2009/0192443 A1* | 7/2009 | Collins, Jr. | 604/24 |
| 2009/0212133 A1* | 8/2009 | Collins, Jr. | 239/338 |
| 2010/0222752 A1 | 9/2010 | Collins, Jr. | |

FOREIGN PATENT DOCUMENTS

| | | |
|---|---|---|
| EP | 0 150 571 A1 | 8/1985 |
| EP | 0 150 571 B1 | 7/1988 |
| EP | 823246 | 2/1998 |
| EP | 0 933 138 A2 | 4/1999 |
| EP | 0933138 A2 | 3/2004 |
| GB | 558 866 | 1/1944 |
| GB | 558 866 A | 1/1944 |
| GB | 1 569 707 | 6/1980 |
| WO | WO 91/12687 A1 | 8/1991 |
| WO | WO 91/14468 | 10/1991 |
| WO | WO 93/20949 | 10/1993 |
| WO | WO 94/13305 | 6/1994 |
| WO | WO 94/23788 | 10/1994 |
| WO | WO9705060 A1 | 2/1997 |
| WO | WO 97/12687 | 4/1997 |
| WO | WO 97/17933 | 5/1997 |
| WO | WO9819383 | 5/1998 |
| WO | WO 99/17888 A1 | 4/1999 |
| WO | WO 00/18455 | 4/2000 |
| WO | WO 00/18455 A1 | 4/2000 |
| WO | WO 0066277 | 11/2000 |
| WO | WO 01/03645 | 1/2001 |
| WO | WO 01/03645 A2 | 1/2001 |
| WO | WO 01/19437 | 3/2001 |
| WO | WO 01/58236 | 8/2001 |
| WO | WO 02 28545 A1 | 4/2002 |
| WO | WO 02/055131 | 7/2002 |
| WO | WO 02/072169 | 9/2002 |
| WO | WO 03 0002045 A1 | 1/2003 |
| WO | WO 03002045 | 1/2003 |
| WO | WO 03002265 | 1/2003 |
| WO | WO 03/026556 | 4/2003 |
| WO | WO 03097139 | 11/2003 |
| WO | WO 2004/050065 | 6/2004 |
| WO | WO 2004/103478 A1 | 12/2004 |
| WO | WO 2004/105864 | 12/2004 |
| WO | WO 2006/006963 A2 | 1/2006 |
| WO | WO 2006/082588 A2 | 8/2006 |
| WO | WO 2006/082588 A2 | 8/2006 |
| WO | WO 2008/015394 A1 | 2/2008 |

OTHER PUBLICATIONS

Communication Relating to the Results of the Partial International Search Report of International Application No. PCT/US2008/001053, filed Jan. 25, 2008.

International Search Report dated Sep. 2, 2004.

Aqueous Ophthalmic Spray as a Novel Method for Delivery of Artificial Tears to the Ocular Surface (JHU Ref. DM-3883), Inventors: Al-Abdulla, Nael A., Snyder, Lee; Web Page www.hohpkinsmedicine.org/lbd/otl/3883.html; Feb. 10, 2004; John Hopkins Medicine; Technology Licensing Opportunities.

Bespak Drug Delivery Technologies, Web page www.bespak.com/drug_compliance.asp?id=7; viewed May 26, 2004.

Dhand, Rajiv M.D.; "Nebulizers That Use a Vibrating Mesh or Plate with Multiple Apertures to Generate Aerosol"; Respiratory Care, Dec. 2002; vol. 47, No. 12; pp. 1406-1418.

HTTP:/WWW.VIOLIGHT.COM, VIOlight toothbrush sanitizer, website, Oct. 12, 2005.

Lee S., Dausch S., Maierhofer G., Dausch D., A new Therapy concept for the treatment of dry eye—the usefulness of phospholipid liposomes, PubMed, Oct. 2004, vol. 221, Issue No. 10, pp. 825-836, Germany.

Visine® Pure tears: A Preservative-free Formula in a Multi-dose bottle, Refractive Eyecare, Sep. 2005, p. 24 and 26.

Monte Kahn, Bioavailability of vitamin $B_{12}$ using a small-volume nebulizer ophthalmic drug delivery system, Clinical and Experimental Ophthalmology, 2005, vol. 33, pp. 402-407.

S. Lee, D. Dausch, S. Dausch, A new therapy concept with a liposome eye spray for the therapy of the "dry eye": First clinical results of a statistical analysis of a long-term study, gms, Oct. 27, 2005, pp. 1-2.

HTTP://WWW.MEDINSTILL.COM, MEDInstill, 2005.

HTTP://WWW1.MYSTICPHARMACEUTICALS.COM, Mystic Pharmaceuticals, Copyright 2004-2005.

Mark B. Abelson, Gail Torkildsen, Aaron Shapiro, Thinking Outside the Eyedropper, Review of Ophthalmology, Sep. 2005, pp. 78-80.

Marco Fabrizio Saettone, Progress and Problems in Ophthalmic Drug Delivery, Business Briefing: Pharmatech 2002, pp. 1-6.

R. Gurny, H. Ibrahim, A. Aebi and P. Buri, Design and evaluation of controlled release systems for the eye, Journal of Controlled Release, vol. 6, Issue 1, Dec. 1987, pp. 367-373.

Linda Roach, Inside the Eye: Precision Drug Delivery, EyeNet Magazine, Jan. 2003.

Medical Instill Technologies, Inc. Brochure, MEDInstill, 2003.

International Search Report for International Application No. PCT/US2008/001053 dated Aug. 27, 2008.

Halberg, G.P., et al., "Drug delivery systems for topical ophthalmic medication," Ann. Ophthalmol. vol. 7, No. 9, Sep. 1975, pp. 1199-1209.

March, W.F., et al., "Abstract of Duration of effect of pilocarpine gel," Arch Ophthalmol, vol. 100, No. 8, Aug., 1982, pp. 1270 1271, one page.

Prince, D.S., "Respiratory arrest following first dose of timolol ophthalmic solution," Chest, vol. 84, No. 5, 1983, pp. 640-641.

Brown, M.M., et al., Abstract of "Improper topical self-administration of ocular medication among patients with glaucoma," Can. J. Ophtalmol. vol. 19, No. 1, Feb. 1984, pp. 2-5 available at www.pubmed.gov, date of availability unknown, one page.

U.S. Appl. No. 12/287,149, dated Oct. 6, 2008, Collins, Jr.
U.S. Appl. No. 12/287,150, dated Oct. 6, 2008, Collins, Jr.
U.S. Appl. No. 12/650,008, dated Dec. 30, 2009, Collins, Jr.
U.S. Appl. No. 11/698,647, dated Jan. 26, 2007, Collins, Jr.

U.S. Appl. No. 12/287,147, dated Oct. 6, 2008, Collins, Jr.

Kumar, V., et al., "Systemic absorption and cardiovascular effects of phenylephrine eyedrops," Am. J. Ophthalmol. vol. 99, No. 22, Feb. 1985, pp. 180-184.

Brown, R.H., et al., "Creating smaller eyedrops by reducing eyedropper tip dimensions," Am. J. Ophthalmol., vol. 99, Apr., 1985, pp. 460-464.

Fraunfelder, F., et al., "Systemic adverse reactions to glaucoma medicationsm," Int. Ophthalmol. Clin. vol. 29, No. 3, Fall 1989, pp. 143-146.

Winfield, A.J., et al., "A study of the causes of non-compliance by patents prescribed eyedrops," Br. J. Ophthalmol., vol. 74, No. 8, 1990, pp. 477-480.

Salminen, L., "Abstract of Review: systemic absorption of topically applied ocular drugs in humans," J. Ocul. Pharmacol., vol. 6, No. 3, pp, 243-249, one page.

Smith, S.E., "Eyedrop installation for reluctant children," Br. J. Ophthalmol., vol. 75, 1991, pp. 480-481.

Burns, E., et al., "Practical problems with eye drops among elderly ophthalmology outpatients," Age and Ageing, Vo. 21, 1992, pp. 168-170.

Stevens, J.D., et al., "Survey of the contamination of eyedrops of hospital in patients and recommendations for the changing of current practice in eyedrop dispensing," Br. J. Ophthalmol., Vo. 76, 1992, pp. 36-38.

Siovin, E.M. et al., *"Bioadhesives in Ocular Drug Delivery,"* Biopharmaceutics of Ocular Drug Delivery, Edman, P., ed., CRC Press, Inc., Boca Raton, F, 1993, chap.9, pp. 145-157.

Van Ooteghem, M., *Biopharmaceutics Ocular Drug Delivery*, Edman, P., ed., CRC Press, Inc., Boca Raton, FL 1993, pp. 27-42, 174-176.

Schoenwald R., "Pharmacokinetics in Ocular Drug Delivery," Edman P, ed. Biopharmaceutics of Ocular Drug Delivery, Boca Raton: CRC Press Inc., 1993, Chapter 10, pp. 159-190.

Hughes, F, et al., "Abstract of Systemic and local tolerability of ophthalmic drug formulations, An update", Drug Saf., 1993, vol. 8, pp. 365-380, one page.

Flach, A., "Abstract of Systemic toxicity. Associated with topical ophthalmic medications," J. Fla. Med. Assoc., 1994; vol. 81, pp. 256-260, one page.

O'Donoghue, E., "Beta blockers and the elderly with glaucoma: are we adding insult to injury?," Br. J. Ophthalmol., vol. 79, 1995, pp. 794-796.

Leino, M., et al., "Delivery Systemic Absorption of Topical Glaucoma Drugs," *Ocular Therapeutics and Drug Delivery*, Reddy, I.K., Technomic Publishing Co., Inc., Lancaster, PA, 1996, p. 255.

Joshin, A., "Microparticulates as an Ocular Delivery System," *Ocular Therapeutics and Drug Delivery*, Reddy, I.K., Technomic Publishing Co., Inc., Lancaster, PA, 1996, chap. 15, pp. 441-457.

Kahn, M. A., et al., "Polymers in Ophthalmic Drug Delivery Systems," *Ocular Therapeutics and Drug Delivery*, published by Technomic Publishing Co., Inc., Lancaster, PA, 1996, chap. 14, pp. 405-431.

Gangrade, N. K., et al., "Topical ophthalmic formulations: Basic considerations," Reddy IK, ed. Ocular therapeutics and drug delivery a multi-disciplinary approach. Lancaster: Technomic, 1996, Chapter 13, p. 377.

Diamond, J., "Systemic adverse effects of topical ophthalmic agents. Implications for older patients," Drugs Aging, 1997, vol. 11, No. 5, pp. 352-360, one page.

Velez, Gisela, et al., "New Developments in Sustained Release Drug Delivery for the Treatment of Intraocular Disease," Br. J. Ophthalmol., vol. 83, Nov., 1999, pp. 1225-1229, available at http://bjo.bmjjournals.com/cgi/content/full/83/11/1225 as of Jan. 16, 2006, 16 pages.

Wakayama, Nobuko I., et al., "Magnetic Acceleration of Inhaled and Exhaled Flows in Breathing," Jap. Journ. Appl. Phys., vol. 39, Part 2, No. 3A/B, Mar. 15, 2000, pp. L262-L264.

Sica, Domenic A., "Ophthalmically Administered β Blockers and their Cardiopulmonary Effects," Journal of Clinical Hypertension, vol. Iii, No. III., May-Jun. 2001, pp. 175-178 and 182.

Kumar, M.T. et al., "Novel therapeutic approaches for uveitis and retinitis," J. Pharm. Pharmaceut. Sci., vol. 4, No. 3, 2001, pp. 248-254.

Macha et al., "Overview of ocular drug delivery," Mitra A.K. ed., Ophthalmic drug Delivery Systems, 2nd ed. Marcel Dekker, Inc., New York, New York, 2003, p. 8.

Van Santvliet, Luc., et al., "Determinants of Eye Drop Size," Survey of Ophthalmology, vol. 49, No. 2., Mar.-Apr. 2004, pp. 197-212.

Lee, S., et al., Abstract of "A new therapy concept with a liposome eye spray for the therapy of the "dry eye": First clinical results of a statistical analysis of a long-term study," regarding Sep. 26, 2004 meeting held in Berlin $102_{nd}$ Jahresteagung der DOG Deutsche Ophthalmologische Gesellschaft e.V. published by gms, available at http://www.egms.de/en/meetings/dog2004/04dog064.shtml as of Oct. 27, 2005, 2 pages.

Kahn, Monte, "Bioavailability of vitamin $B_{12}$ using a small-vol. nebulizer ophthalmic drug delivery system," Clinical and Experimental Ophthalmology, vol. 33, 2005, pp. 402-407.

Tattersall, C., et al., Abstract of "Resting pulse rate in a glaucoma clinic: the effect of topical and systemic beta-blocker usage," Eye, Apr. 1, 2005 available at http://www.ncbi.nlm.nih.gov/entrez/query.fcgi?cmd=Retrieve&db=pubmed&dopt=Abstract . . . as of Oct. 17, 2005, 1 page.

Abelson, Mark B., et al., "Thinking Outside the Eyedropper," Review of Ophthalmology, Sep. 2005, pp. 78-80.

Author unknown, "Visine® Pure Tears: A Preservative-free Formula in a Multi-dose Bottle," Refractive Eyecare, Sep. 2005, pp. 24 and 26.

Author unknown, "Violight™—Frequently Asked Questions" available at http://www.violight.com as of Oct. 12, 2005, 1 page.

Author unknown, "Violight™—Shop Violight" available at http://www.violight.com as of Oct. 12, 2005, 1 page.

Author unknown, "Violigh™—How it Works" available at http://www.violight.com as of Oct. 12, 2005, 1 page.

http://images.businessweek.com/ss/05/06/idea2005/source/115.htm as of Oct. 12, 2005, 1 page.

Kesner, J., "Guarantee clean hygiene" Sep. 8, 2005 article available at http://www.violight.com as of oct. 12, 2005, 1 page.

Audia, et al., "Close your eyes now, make a wish!" advertisement, available at http://vvww.wveyes.com/Tears%20Apain%20Lipisome%20Spray.htm as at of Oct. 27, 2005, one page.

Author unknown, "Tears Again Lipisome" advertisement, available at http://www.aclens.com/da.asp?ID=29&Mode=Enlarge as of Oct. 27, 2005, one page.

Lee, S., et al., Abstract of "A new therapy concept for the treatment of dry eye—the usefulness of phospholipid liposomes," Klin Monatsbl Augenheilkd., vol. 221, No. 10, Oct. 2004, pp. 825-836 available at http://www.ncbi.nlm.nih.gov/entrez/query.fcgi?cmd=Retrieve&db=pubmed&dopt=Abstract . . . as of Oct. 27, 2005, 2 pages.

Zhu, Shengwei, et al., Abstract of "Study on inhalation region by means of CFD analysis and experiment," Building and Environment, vol. 40, No. 10, Oct., 2005, pp. 1329-1336, available at http://www.sciencedirect.com/science?_ob=ArticleURL&_udiB6V23-4F4VVYM5-1&_us . . . as of Apr. 12, 2008, 2 pages.

* cited by examiner

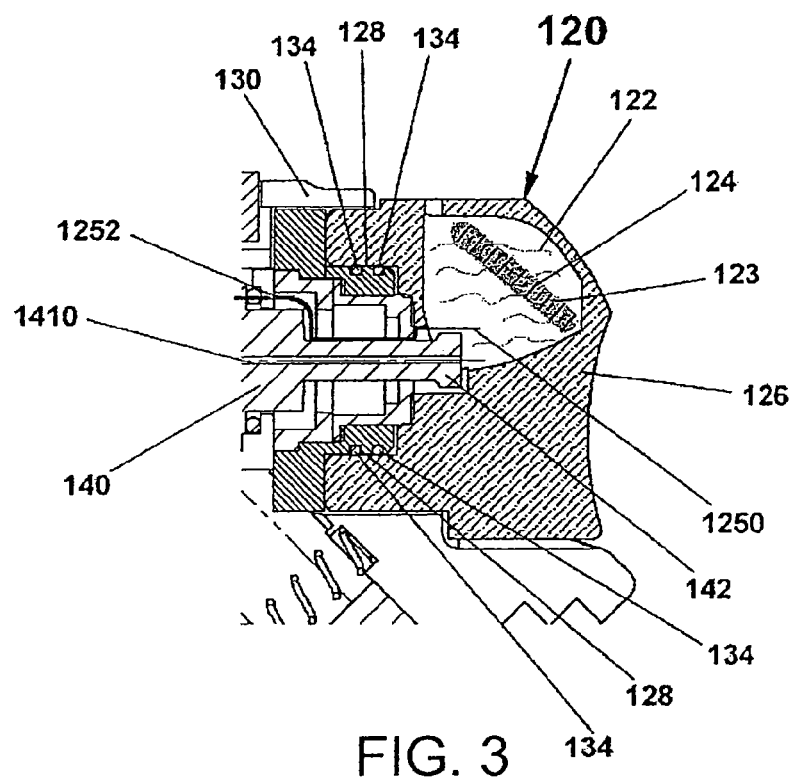
FIG. 3
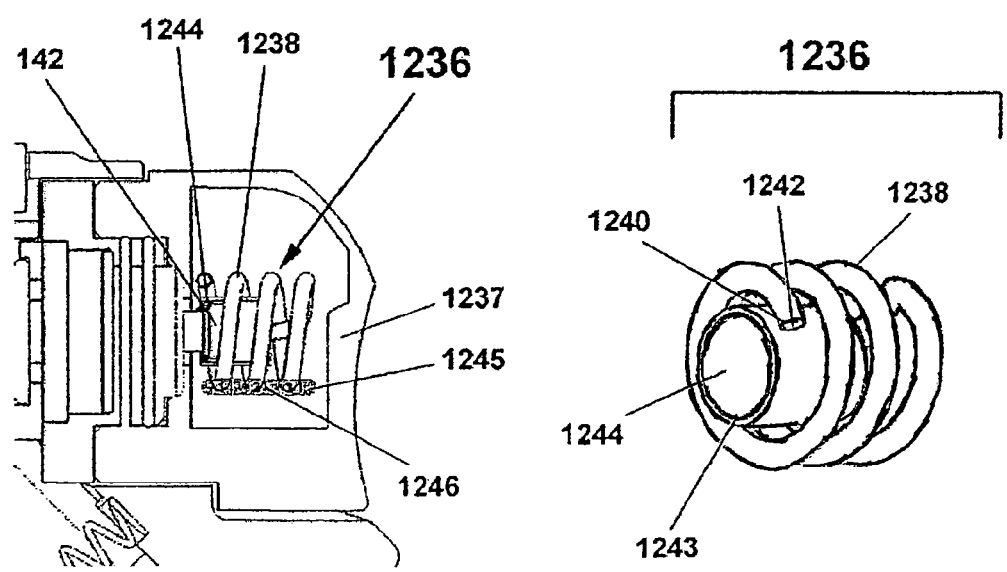
FIG. 7
FIG. 8

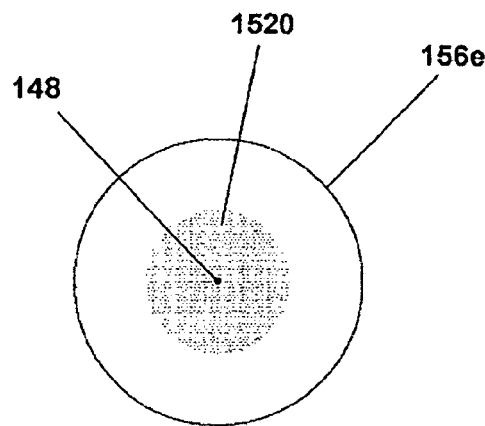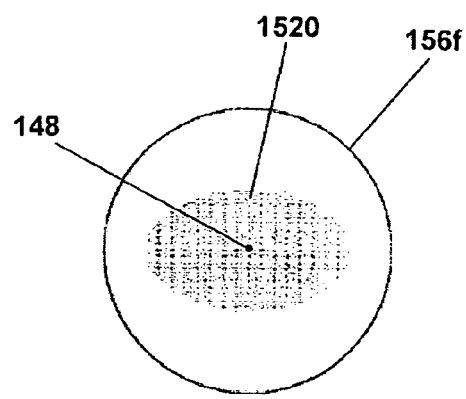
FIG. 13A  FIG. 13B
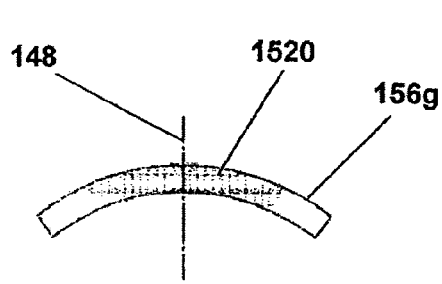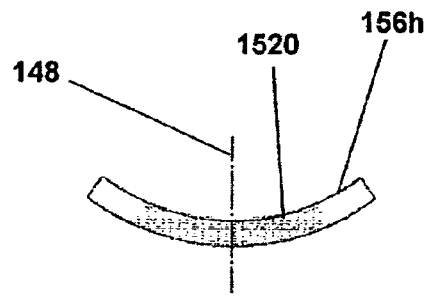
FIG. 13C  FIG. 13D
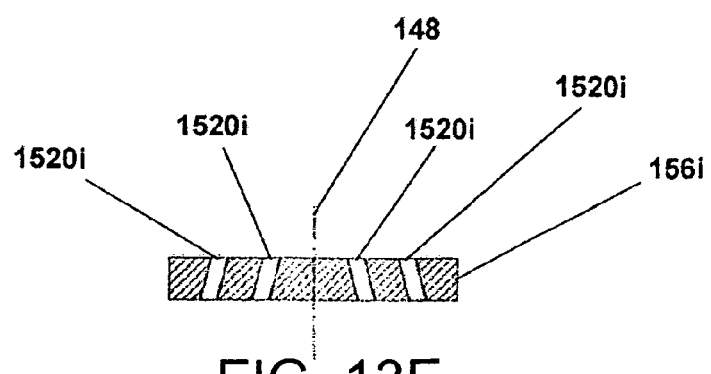
FIG. 13E

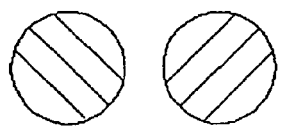 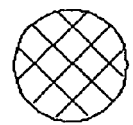 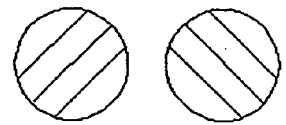
FIG. 17A  FIG. 17B  FIG. 17C
 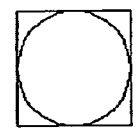 
FIG. 18A  FIG. 18B  FIG. 18C
 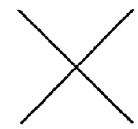 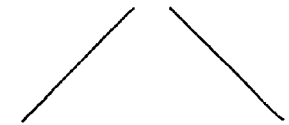
FIG. 19A  FIG. 19B  FIG. 19C
 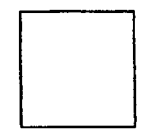 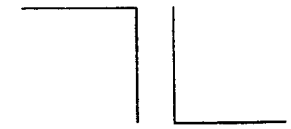
FIG. 20A  FIG. 20B  FIG. 20C
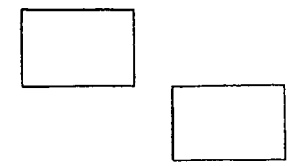  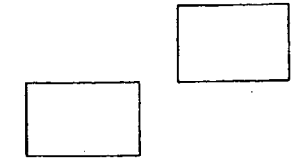
FIG. 21A  FIG. 21B  FIG. 21C

OPHTHALMIC FLUID DELIVERY DEVICE AND METHOD OF OPERATION

CROSS REFERENCE TO RELATED APPLICATIONS

The present application is a Continuation-in-Part Application of U.S. patent application Ser. No. 10/851,611, filed May 20, 2004, which claims priority from U.S. Provisional Patent Application Ser. No. 60/471,883, filed May 20, 2003 and from U.S. Provisional Patent Application Ser. No. 60/485,305, filed Jul. 3, 2003, each of which applications is incorporated herein by reference in its entirety.

FIELD OF THE INVENTION

The present invention relates to drug delivery devices for dispensing liquid as an aerosol or atomized mist and, more particularly, for dispensing medicaments and other fluids to the eye.

BACKGROUND OF THE INVENTION

Presently, conventional eye drops are the standard means of delivering medicaments to the eye. This means of ophthalmic drug delivery, however, has numerous problems. For example, the average eye drop (approximately 50 micro liters) far exceeds the eye's capacity (7 micro liters in the pre-corneal tear film and a maximum of about 30 micro liters in the lower cul-de-sac) effectively destabilizing and stripping the natural tear film. This results in a brief period of massive over-dosage, which is quickly cleared by reflex lacrimation, blinking and nasolacrimal drainage, resulting in sub-therapeutic drug levels until the next medication application. This approach represents very inefficient pharmacokinetics. Far smaller volumes of medicament (approximately one tenth of a conventional drop) are desirable and are, in fact, retained by the eye and "bio-available" for a substantially longer time.

Attempts to prolong ocular contact time by various adaptations, such as the use of particulate suspensions, have led to other drawbacks including ocular irritation and excessively slow drug release. Ointments and gels, though providing prolonged contact time, create obvious visual disturbances.

Further, local irritations and toxicities often result from the regular use of eye drops. These situations vary widely depending on the pharmacologic agent, preservatives and other additives being used, but this is clearly a very non-physiologic and inefficient system of medication administration. Chronic use of eye drops for such conditions as glaucoma and prolonged infections and inflammations can, in fact, cause substantial morbidity. Additionally, serious and even fatal reactions to sympathomimetic and beta-adrenergic blocking agents have occurred as a result of systemic absorption of eye drops via nasolacrimal drainage.

Besides the above issues, there are a great many difficulties that patients experience with the mechanics of eye drop administration. Elderly patients, the largest group of eye drop users, often have hand-eye coordination problems, tremors or arthritis, affecting the hands and/or the cervical spine, making eye drop administration difficult if not impossible. Many users report that they have trouble keeping track of their regimens and often repeat doses or miss them entirely, suffering potential consequences in either event. Further, pediatric patients, often unable to comprehend the reasons and benefits behind the administration of eye medication, often fight such application, typically resulting in underdosing due to the patient's attempts to prevent the eye drops from being administered, or overdosing, as a result of the administrator's attempt to ensure that sufficient dosage is being applied.

Additionally, very few regular users of eye drops, in any age group, actually observe the ideal technique of administration, including tear sac compression, to minimize excretory loss and potential systemic absorption. It is sometimes difficult to tell if the drop was properly instilled. Direct application to the cornea can result in the drop "bouncing" from the eye with little or no benefit.

Regular eye drop users commonly report using several drops which "missed" the eye until they are sure they properly instilled the drop. Also, many eye drop bottles are fabricated in such a way that loss is unavoidable as soon as the dropper is tilted. Finally, a significant number of regular users put another drop or two in the eye "just to be sure". All of the above represent needless waste of expensive medication (many glaucoma medications cost $70-$80 for a 5 ml bottle) and also increased the risk of side effects, while actually reducing the therapeutic benefit.

The ophthalmic literature is rife with references to the need for a better means of ophthalmic drug delivery. With an estimate of 25 million users of eye drops in the United States alone, the magnitude of the public health issue is considerable. Accordingly, a new means of ophthalmic drug delivery is needed.

The concept of "spraying" medicated solutions on to the eye is not a new one. A number of devices have been conceptualized and developed for this purpose. Various means of atomizing and propelling solutions including mechanical pumps, gas-propelled jets and pistons, etc. which have inherent drawbacks relating to difficulties with calibrating the flow velocity, volume and particle size of the emitted spray. See, for example, U.S. Pat. Nos. 3,170,462; 5,630,793; and 6,062,212.

It is hypothesized that the generated mist will expand and "therapeutically alter" but not significantly disrupt the physiologic tear film allowing for a more natural process in the transmission of therapeutic agents to the surface and the interior of the eye. A much smaller volume of solution can be administered below the blink and lacrimation thresholds, allowing for a prolonged time of application. The aggregate administration of a drug in thousands of 5-micron particles should significantly exceed that of a single eye drop, leading to greater concentrations of the drug (bioavailability). Furthermore, the surface tension of a standard drop is a barrier to "mixing" and tear film incorporation. This problem is expected to be avoided with micronebulization.

An additional benefit to mist administration of eye medications is the avoidance of dropper bottle contamination which commonly occurs from contact with the eyelid. In the professional office setting, this problem has led to many documented epidemics of viral keratoconjunctivitis. During medication administration via a dropper bottle to a patient with viral keratoconjunctivitis, the bottle tip may inadvertently touch the eye or eyelid of the affected patient, transferring the virus to the bottle tip. Subsequent medication administrations to other patients using the same dropper bottle transmits the virus to those patients.

Some of the beneficial features of an ophthalmic medication spray dispenser include the following: great ease of use; can be used in any "attitude" (i.e. with patient sitting, erect, lying down, head tilted back, etc.); abbreviated treatment cycle as compared to eye drop usage; improved bioavailability/efficacy; improved safety (reduced local and systemic side effects); improved sterility; increased compliance due to ease of use and "alert" systems; possibility of singular efficacy in the treatment of certain vision threatening infections; conservation of material (reduced volume, diminished waste/loss); and system (fixation target to help ensure proper application).

It would be beneficial to provide a system for applying the desired small amounts (7 to 10 micro liters) of optical medication, along with at least some of the above-listed beneficial features, while eliminating the drawbacks associated with previous means of drug delivery.

BRIEF SUMMARY OF THE INVENTION

Briefly, and according to one exemplary aspect, the present invention provides an ophthalmic fluid delivery device adapted to deliver an ophthalmic fluid in the form of a mist to an ocular region of a patient. The ophthalmic fluid delivery device comprises a nozzle defining an aperture through which the ophthalmic fluid can flow and at least one shutter positioned proximate to the aperture of the nozzle. The shutter is mounted for movement with respect to the aperture of the nozzle between an open position permitting flow of the ophthalmic fluid through the aperture of the nozzle and a closed position at least partially covering the aperture. A shutter actuator is positioned proximate to the shutter. The shutter actuator is mounted for movement with respect to the nozzle, and the shutter actuator is coupled to the shutter such that the movement of the shutter actuator moves the shutter between the open position and the closed position.

Additionally, and according to another exemplary aspect, the present invention provides an ophthalmic fluid delivery device adapted to deliver an ophthalmic fluid in the form of a mist to an ocular region of a patient. The ophthalmic fluid delivery device comprises a nozzle assembly configured to deliver the ophthalmic fluid to the ocular region of the patient generally along a nozzle axis. A handle assembly is coupled to the nozzle assembly and configured to be gripped by a hand of the patient or another user of the ophthalmic fluid delivery device. The handle assembly is oriented generally along a handle axis. The nozzle axis and the handle axis together define an angle greater than 90 degrees such that the ophthalmic fluid is delivered to the ocular region of the patient along the nozzle axis that is obtuse with respect to the handle axis.

Further, and according to yet another exemplary aspect, the present invention provides an ophthalmic fluid delivery device adapted to deliver an ophthalmic fluid in the form of a mist to an ocular region of a patient from a reservoir containing the ophthalmic fluid. The ophthalmic fluid delivery device comprises a body defining a cavity sized to accommodate the reservoir and a nozzle assembly coupled to said body proximate the cavity. The nozzle assembly is configured to deliver the ophthalmic fluid from the reservoir and toward the ocular region of the patient. An aperture is defined by the body adjacent the cavity defined by the body. The aperture is positioned to permit visualization of the reservoir from outside said body when the reservoir is positioned within the cavity of the body.

Also, and according to still another exemplary aspect, the present invention provides an ophthalmic fluid delivery device adapted to deliver an ophthalmic fluid in the form of a mist to an ocular region of a patient from a reservoir containing the ophthalmic fluid. The reservoir defines a reservoir surface contour unique to the ophthalmic fluid. The ophthalmic fluid delivery device comprises a keyed contour positioned to receive the reservoir surface contour to permit insertion of said reservoir in a predetermined alignment and to prevent insertion of the reservoir in an alignment other than the predetermined alignment.

According to yet another exemplary aspect, the present invention also provides a method of delivering an ophthalmic fluid using an ophthalmic fluid delivery device. The method includes moving at least one shutter with respect to an aperture of a nozzle of the ophthalmic fluid delivery device from a closed position at least partially covering the aperture toward an open position permitting flow of the ophthalmic fluid through the aperture. Ophthalmic fluid is discharged through the aperture of the nozzle of the ophthalmic fluid delivery device.

According to still another exemplary aspect, the present invention provides a method of delivering an ophthalmic fluid from an ophthalmic fluid delivery device having a handle axis and a discharge axis. The method includes the steps of orienting the discharge axis between about 105 degrees and about 125 degrees from the handle axis and discharging the ophthalmic fluid along the discharge axis.

Further, and according to yet another exemplary aspect, the present invention provides a method of preparing an ophthalmic fluid delivery device to deliver an ophthalmic fluid. The method includes inserting a reservoir containing the ophthalmic fluid into a cavity defined by the delivery device. A label on the reservoir is visualized through an aperture defined by the delivery device.

According to still another exemplary aspect, the present invention provides a method of preparing an ophthalmic fluid delivery device to deliver an ophthalmic fluid. The method includes selecting a reservoir containing the ophthalmic fluid from among a group of reservoirs containing a group of ophthalmic fluids. The reservoir is inserted into a cavity of the delivery device such that a contour on the reservoir aligns with a contour of the cavity, thereby maintaining the reservoir in a predetermined alignment and preventing an alignment other than the predetermined alignment.

Additionally, and according to another exemplary aspect, the present invention provides a method of preparing an ophthalmic fluid delivery device to deliver an ophthalmic fluid. The method includes switching the device from an "off" position to an "on" position and performing at least one of the following steps: opening an aperture of the ophthalmic fluid delivery device to permit flow of ophthalmic fluid therethrough; opening a venturi passage defined by the ophthalmic fluid delivery device to permit flow of air through the aperture with the ophthalmic fluid; or activating an indicator to indicate that the ophthalmic fluid delivery device is ready to deliver the ophthalmic fluid.

Further, according to yet another exemplary aspect, the present invention provides an ophthalmic fluid delivery device adapted to deliver an ophthalmic fluid in the form of a mist to an ocular region of a patient. The ophthalmic fluid delivery device includes a transducer configured to advance the ophthalmic fluid toward the ocular region of the patient. The transducer defines a lumen for the flow of the ophthalmic fluid having an aspect ratio of between about 22 and about 26.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain features of the invention. In the drawings:

FIG. 3 is an enlarged side profile view of a first embodiment of a fluid reservoir connected to the device.

FIG. 7 is an enlarged side profile view of a third embodiment of a fluid reservoir.

FIG. 8 is a perspective view of the reservoir of FIG. 7.

FIG. 13*a* is a top plan view of a first embodiment of a mesh plate.

FIG. 13*b* is a top plan view of a second embodiment of a mesh plate.

FIG. 13*c* is a side view, in section of a third embodiment of a mesh plate.

FIG. 13*d* is a side view, in section, of a fourth embodiment of a mesh plate.

FIG. 13*e* is an enlarged partial sectional view of a fifth embodiment of a mesh plate.

FIG. 17*a* is a schematic view of a first embodiment of a targeting mechanism showing the device too close to the target.

FIG. 17*b* is a schematic view of the first embodiment of the targeting mechanism showing the device a correct distance from the target.

FIG. 17*c* is a schematic view of the first embodiment of the targeting mechanism showing the device too far from the target.

FIG. 18*a* is a schematic view of a second embodiment of a targeting mechanism showing the device too close to the target.

FIG. 18*b* is a schematic view of the second embodiment of the targeting mechanism showing the device a correct distance from the target.

FIG. 18*c* is a schematic view of the second embodiment of the targeting mechanism showing the device too far from the target.

FIG. 19*a* is a schematic view of a third embodiment of a targeting mechanism showing the device too close to the target.

FIG. 19*b* is a schematic view of the third embodiment of the targeting mechanism showing the device a correct distance from the target.

FIG. 19*c* is a schematic view of the third embodiment of the targeting mechanism showing the device too far from the target.

FIG. 20*a* is a schematic view of a fourth embodiment of a targeting mechanism showing the device too close to the target.

FIG. 20*b* is a schematic view of the fourth embodiment of the targeting mechanism showing the device a correct distance from the target.

FIG. 20*c* is a schematic view of the fourth embodiment of the targeting mechanism showing the device too far from the target.

FIG. 21*a* is a schematic view of a fifth embodiment of a targeting mechanism showing the device too close to the target.

FIG. 21*b* is a schematic view of the fifth embodiment of the targeting mechanism showing the device a correct distance from the target.

FIG. 21*c* is a schematic view of the fifth embodiment of the targeting mechanism showing the device too far from the target.

FIG. 28 is a side elevational view of an alternative embodiment of a device according to the present invention.

FIG. 29 is a top plan view of the device of FIG. 28.

FIG. 30 is a sectional view of the device, taken along lines 30—30 of FIG. 29.

FIG. 31 is an enlarged view of internal portions of the device shown in FIG. 30.

FIG. 32 is an exploded view of selected assemblies of the device of FIG. 28.

FIG. 33 is a perspective view of a body assembly of the device of FIG. 28.

FIG. 34 is a side view, in section, of the body assembly of FIG. 33.

FIG. 35 is an exploded perspective view of a top housing assembly of the device shown in FIG. 28.

FIG. 36 is a side view, in section, of the top housing assembly of FIG. 35.

FIG. 37 is a perspective view of a transducer assembly of the device shown in FIG. 28.

FIG. 38 is a side elevational view, in section, taken along lines 38—38 of FIG. 37.

FIG. 39 is an exploded perspective view of the transducer assembly

FIG. 40 is an enlarged view of a portion of the transducer assembly taken along circle 40 of FIG. 38.

FIG. 41 is an exploded view of a mesh cap assembly of the device shown in FIG. 28.

DETAILED DESCRIPTION OF THE INVENTION

Certain terminology is used in the following description for convenience only and is not limiting. As used herein, the term "distal" is meant to mean the discharge end of the inventive device and the term "proximal" is meant to mean the end of the inventive device held by user. The terminology includes the words above specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The present invention provides a novel device and method for ophthalmic drug delivery. In preferred embodiments, the present invention provides a small, hand-held, battery or AC powered device that nebulizes liquid eye medications into a fine mist. The mist from the device is directed at the eye to be treated and the drug is delivered via the mist.

A preferred means of forming the mist is by ultrasound energy generated by a piezoelectric transducer or other suitable piezo device. A small plume of nebulized solution is generated, consisting of particles measuring what is believed to be an average of about five microns in diameter. The volume of each emission is dependent on the rate of mist generation (typically measured in micro liters per second) as well as the duration of the operation of the device, which may be easily varied by using an electronic control circuit. The shape, dimensions and focus of the emitted mist are proportioned for delivery to the human eye. The momentum of the mist is subliminal to the ocular blink and lacrimation reflexes and may also create a soothing sensation in the eye. The device is equally efficient when used in any "attitude" from a natural, upright head posture to leaning forward or lying back. Application time is significantly abbreviated compared to eye drop usage, which typically requires several maneuvers and careful attention to detail to ensure proper administration.

One preferred embodiment of the invention is now described with reference to FIGS. 1 and 2, which show a hand held device 100 that directs a mist of drug to an eye for treatment. As will be described in more detail below, the device 100 includes a vial or reservoir 120 of the fluid to be delivered to the eye, such as a drug. The user holds the device 100 and, by operating an activation switch, causes the device 100 to generate a mist of the liquid, which is discharged from the head portion 110 of the device 100. The user simply aims the head of the device at the target eye to allow the mist to contact the eye.

Figure 1:
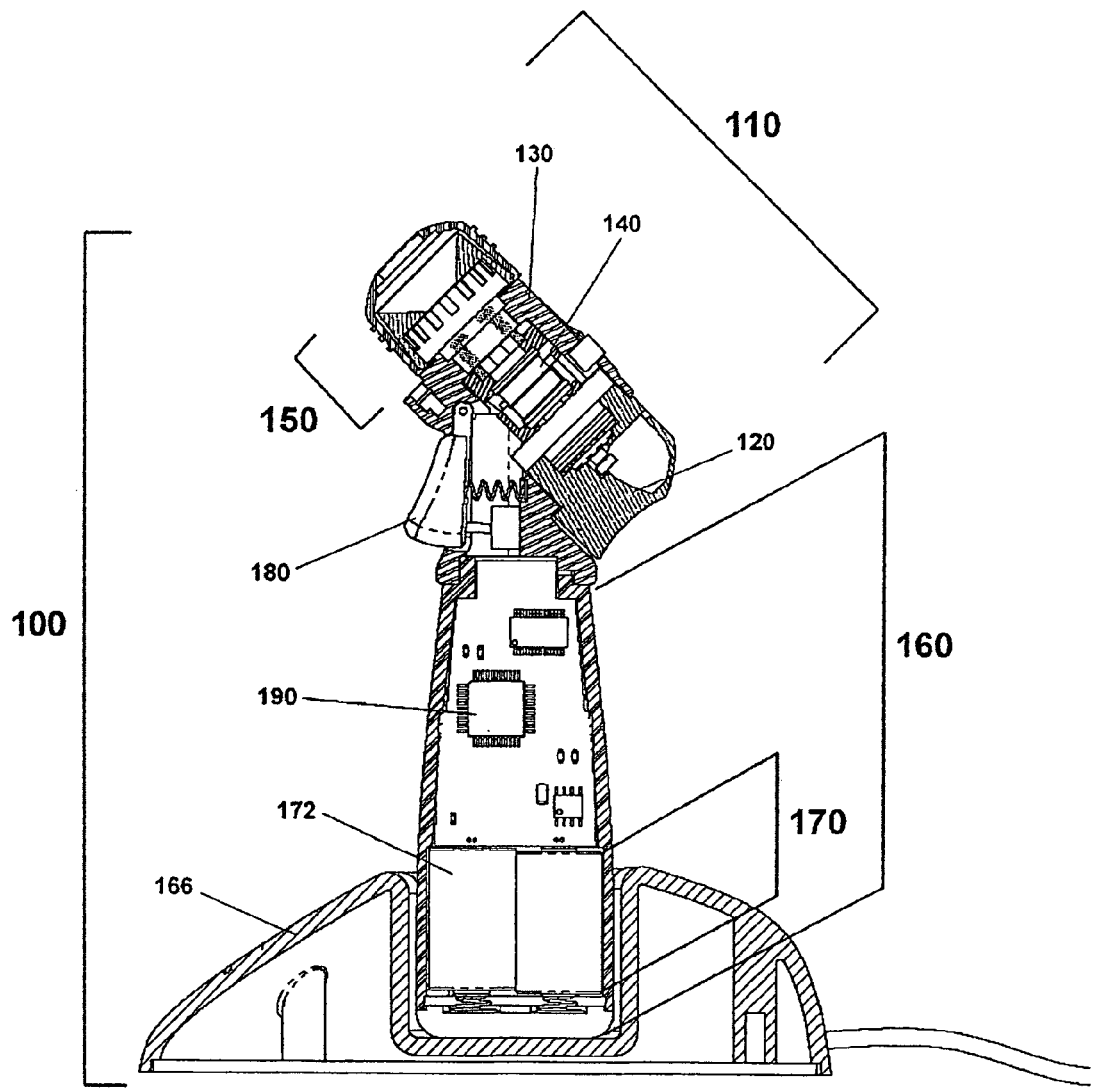
FIG. 1 is a side elevational view, partially broken away, of a mist spraying device according to a first embodiment of the present invention.
Figure 2:
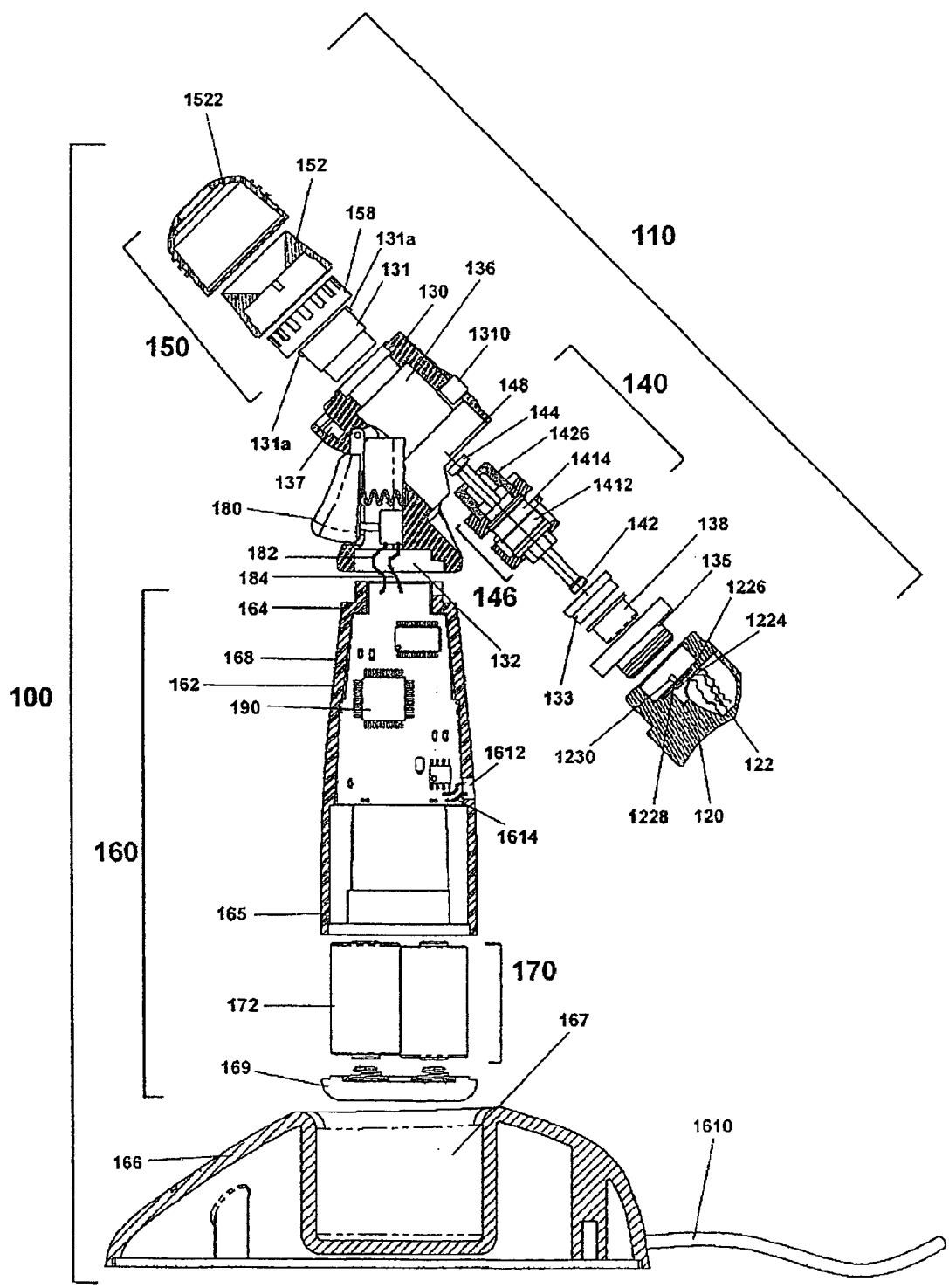
FIG. 2 is an exploded view of the device of FIG. 1.

Referring to FIGS. 1 and 2, the major components of the device 100 are shown. The components include a head portion 110 and a handle portion 160. The head portion 110 preferably contains, from a proximal to a distal direction, a fluid reservoir 120 to retain a fluid 122 to be administered, a body 130 that houses a prime mover 140 to draw the fluid from the reservoir 120 and propel the fluid 122 out the distal end of the device 100, and a nozzle assembly 150 which aerosolizes the fluid 122 and to form a mist pattern of the fluid 122 as the fluid 122 is directed toward its target. The handle portion 160 preferably contains the power source 170, such as a battery, an activation switch 180 to activate the device, and a system controller 190 that controls the various operational aspects of the device 100.

Head Portion

The head portion 110 includes the body 130 that connects the reservoir 120, the prime mover 140, and the nozzle assembly 150 together. The head portion 110 is connected to the handle portion 160 and provides a conduit for electrical leads (not shown) extending from the reservoir 120 and the prime mover 140 to the system controller 190.

Reservoir

Referring to FIG. 3, in which an enlarged view of a preferred embodiment of the reservoir 120 is shown, the fluid reservoir 120 may can be a vial pre-filled with the fluid 122 to be delivered to the eye. The reservoir 120 may incorporate a scale comprising a clear window 123 with volume graduation markings 124 to indicate fill level or doses of fluid 122 remaining in the reservoir 120. In the present embodiment, the scale is read with the device 100 standing on its base 166, as shown in FIG. 1.

Figure 4:
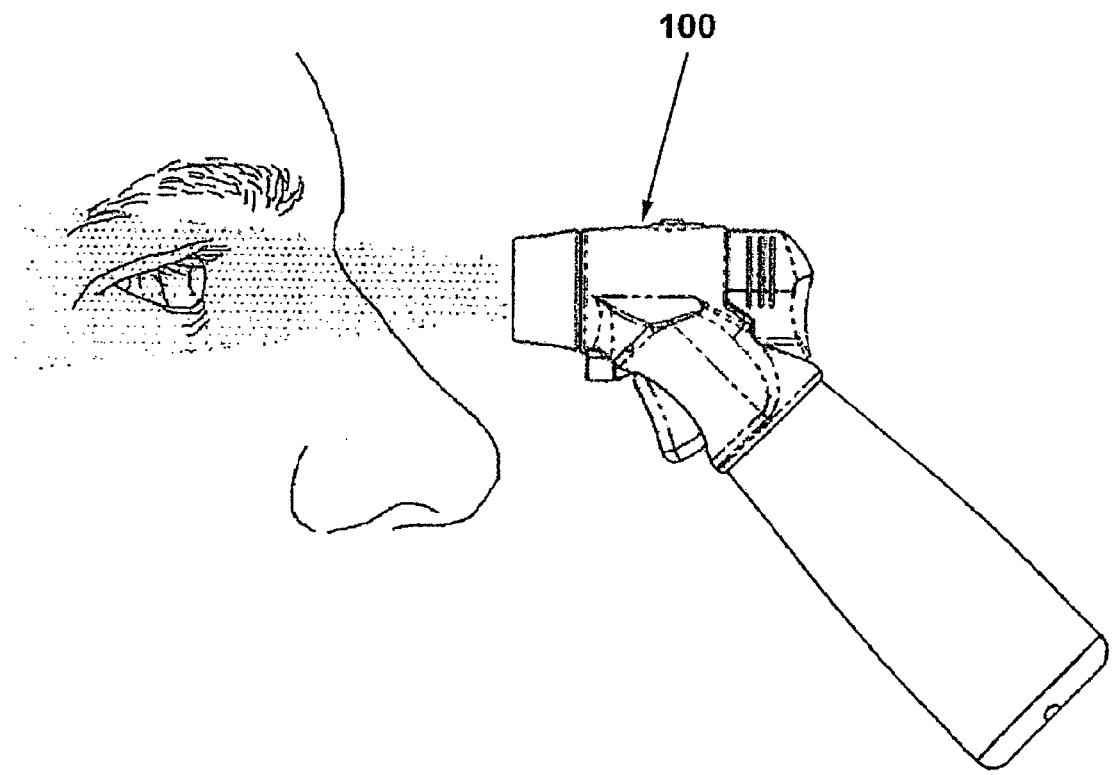
FIG. 4 is a side profile view showing the device being used to spray a mist into a patient's eye.

The reservoir 120 is preferably shaped to maintain contact with the prime mover 140 when the device 100 is held in a preferred operational orientation while spraying into an eye (as shown in FIG. 4), or is tilted in any direction within 45 degrees of horizontal. The reservoir 120 is preferably further shaped to maximize the percentage of the total fill volume that is actually dispensed.

Referring back to FIG. 3, the reservoir 120 houses the fluid 122 that is used to form the aerosolized mist when the device 100 is operated. The reservoir 120 is preferably a removable and replaceable cartridge 126 that is securably connectable to the body 130 so that the reservoir 120 does not accidentally readily separate from the body 120, yet is easily replaceable when the reservoir 120 is empty or when a reservoir 120 containing a different type of fluid is desired to be connected to the device 100.

Preferably, the reservoir 120 includes an engagement surface 128 disposed proximate to an upper and a lower side of the reservoir 120. The engagement surface 128 slides over a corresponding extension in the body 130, as shown in FIG. 3, so that the reservoir 120 is retained onto the body 130 with a frictional fit. Preferably, the extension includes a plurality of seals, such as O-rings 134, that provide a sealing engagement between the reservoir 120 and the body 130 and assists in frictionally retaining the body 120 to the reservoir 130. Alternatively, the reservoir 120 may connect with the body 130 by other means known to those skilled in the art, including, but not limited to, threaded connections, bayonet fittings, or other suitable means.

Figure 5:
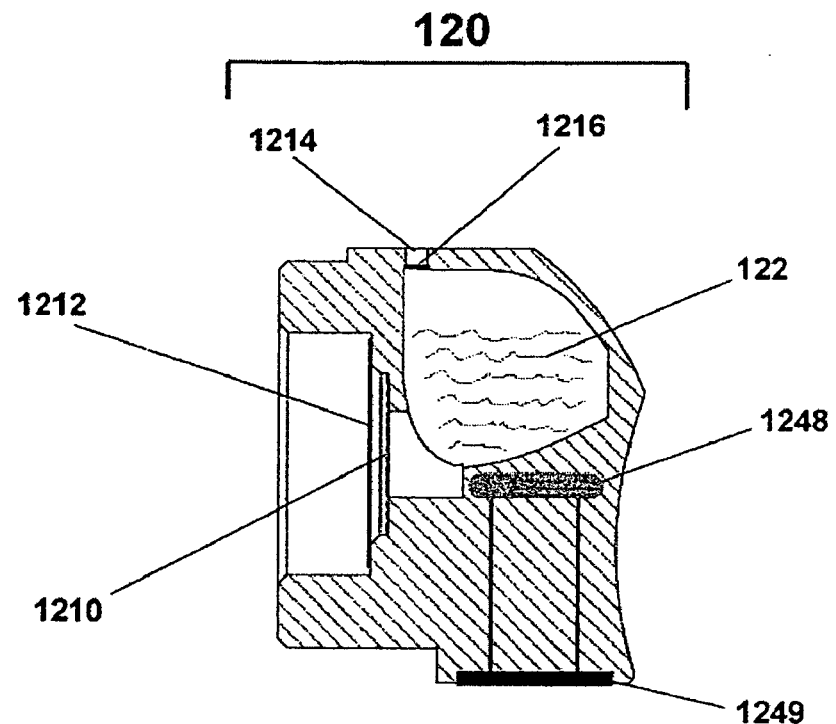
FIG. 5 is a side profile view of the first embodiment of the fluid reservoir shown in FIG. 3, having been removed from the device.

In the embodiment shown in FIG. 5, which shows the reservoir 120 removed from the remainder of the device 100, the reservoir 120 includes an open face 1210 that is covered by an air impermeable seal 1212. Initially, the open face 1210 allows the fluid 122 to be deposited into the reservoir 120, and then sealed with the seal 1212. Such a seal 1212 may be constructed from thin gauge aluminum, or some other suitable material, with a biocompatible coating disposed on both faces of the seal 1212. The seal 1212 is attached to the reservoir 120 with a biocompatible adhesive. The seal 1212 is designed to maintain sterility of the fluid 122 within the reservoir 120, yet be able to be easily punctured by the proximal end 142 of the prime mover 140 upon connecting the reservoir 120 to the body 130 so that the fluid 122 in the reservoir 120 is put into fluid communication with the proximal end 142 of the prime mover 140, as shown in FIG. 3.

For a reservoir 120 having a rigid form, such as the reservoir 120 shown in FIG. 5, a vent 1214 is formed in the wall of the reservoir 120, preferably proximate to the top of the reservoir 120, to allow air to be drawn into the reservoir 120 to compensate for the loss volume of fluid 122 as the fluid 122 is drawn out of the reservoir 120 due to operation of the device 100. A filter 1216 covers the vent 1214 to allow ambient air into the interior of the reservoir 120, but prevents fluid 122 in the reservoir 120 from leaking out of the vent 1214. While a presently preferred embodiment of the reservoir 120 envisions the fluid 122 to be prepackaged in the reservoir 120, those skilled in the art will recognize that the reservoir 120 may also be refillable, such as through the vent 1214.

Figure 6:
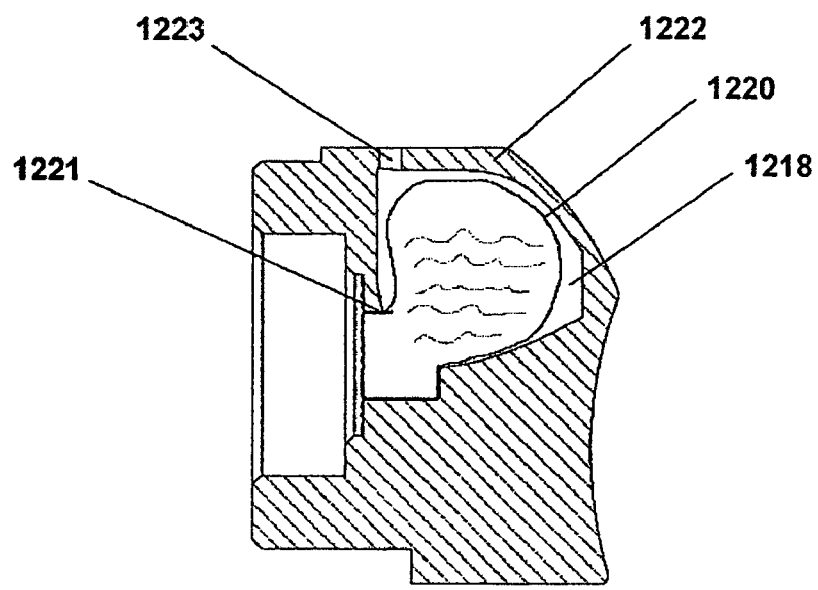
FIG. 6 is an enlarged side profile view of a second embodiment of a fluid reservoir.

Alternatively, as shown in FIG. 6, an alternate embodiment of a reservoir 1218 may have a collapsible bladder 1220 that collapses under vacuum as the fluid 122 is drawn out of the reservoir 1218 during operation of the device 100, without any air being able to enter the reservoir 122. The bladder 1220 is preferably supple, biocompatible, and bondable. In the presently preferred embodiment, the bladder 1220 is constructed of aluminum film coated on both sides with a polymer resin. In the presently preferred embodiment, the bladder 1220 is approximately 0.025 to 0.10 mm thick. The bladder 1220 is attached to a rigid bladder neck 1221. The neck 1221 prevents the bladder 1220 from contacting the proximal end 142 of the prime mover 140 as the bladder 120 collapses. Contact with the proximal end 142 would impede the function of the prime mover 140. The bladder neck 1221 may be injection molded or extruded from a material that is rigid, biocompatible, and bondable. A material which meets these criteria includes polyethylene, although those skilled in the art will recognize that other, suitable, biocompatible materials may be used. The bladder 1220 and bladder neck 1221 are housed in a rigid reservoir housing 1222. The housing 1222 is preferably injection molded from low cost polymer resins such as PVC, ABS, or polypropylene.

An air vent 1223 in the housing 1222 allows the collapsible bladder 1220 to collapse as the fluid 122 is withdrawn from the reservoir 1218, so that no adverse suction forces are generated during operation of the device 100. The air entering the vent 1223 does not need to be filtered, since the bladder 1220 isolates the fluid 122 from the air. In this embodiment, no make-up air is required to enter the bladder 1220.

Without limiting the type of fluids that could be contained in the reservoir 120, 1218 and dispensed by the present invention, diagnostic agents used by the medical professional that could be delivered with the present invention include mydriatics/cycloplegics, anesthetics, flourescein and flourescein/anesthetic combinations, and mydriatic reversal agents. Other agents which could be delivered with the present invention include over-the-counter agents, e.g., ophthalmic decongestants and lubricants, glaucoma medications (prestaglandins, beta blockers, alpha adrenergic agents, carbonic anhydrase inhibitors, miotics), and other ophthalmic medications. Optionally, several different therapeutic agents can be custom formulated in a single fluid to simplify adherence to multiple medication regimens.

Again, while an envisioned used for the device 100 of the present invention is directed toward ophthalmic use, those skilled in the art will recognize that the device 100 of the present invention may be used in other areas, such as respiratory treatment, and that other fluids, including respiratory medicaments, may be contained in the reservoir 120 instead.

Preferably, for photo-sensitive medicaments, the reservoir 120 may be tinted to prevent the transmission of certain deleterious wavelengths of light to the fluid 122 to prolong the useful life of the medicament in the reservoir 120. The tint may be a dark brownish tint that is presently used for such medicaments in bottle/eye dropper form.

Optionally, as shown in FIG. 2 the reservoir 120 may include a self-sealing valve 1224 in a distal wall 1226 of the reservoir 120. The self-sealing valve 1224 allows the reservoir 120 to be inserted into the body 130, and then removed from the body 130 without leaking fluid 122 from the reservoir 120.

The self-sealing valve 1224 is preferably biased toward a closed position, such as by a helical spring (not shown). A seal, such as an o-ring 1228, seals the valve 1224 against the wall 1226 of the reservoir 120 to eliminate fluid leakage from the reservoir 120 when the valve 1224 is in the closed position. A valve stem 1230 extends distally from the valve 1224. When the reservoir 120 is inserted into the body 130, the proximal end 142 of the prime mover 140 engages the valve stem 1230 and forces the valve stem 1230 into the reservoir 120, opening the reservoir 120 into fluid communication with the prime mover 140.

An alternative embodiment of a reservoir 1236 is shown in FIGS. 7 and 8. The reservoir 1236 is housed in a removable and replaceable cartridge 1237. The reservoir 1236 incorporates a generally coiled tube 1238 that is sized to partially surround the proximal end 142 of the prime mover 140. The tube 1238 may be constructed from polyethylene, although those skilled in the art will recognize that other suitable, biocompatible materials may be used. The tube 1238 preferably has a wall thickness in the range of approximately 0.1 to 0.3 mm thick, and an inside diameter in the range of approximately 1 to 5 mm. One end 1240 of the tube 1238 is fitted with a filter 1242 to allow makeup air to enter as the fluid 122 in the reservoir 1236 is drawn down. This filter 1242 is a biocompatible, gas-permeable membrane that is impermeable to liquid but permeable to air. One such material that may be used for the filter 1242 is Tyvek®. A distal end 1243 of the tube 1238 is sealed with a fluid impermeable seal 1244 that is broken by the distal end 142 of the prime mover 140 when the reservoir 1236 is connected to the device 100, as shown in FIG. 7.

As the device 100 is operated and medication is consumed, the fluid 122 is drawn along the tube 1238. The diameter of the tube 1238 is preferably specified in relation to the viscosity of the fluid 122 to insure that surface tension causes the fluid 122 to move in a column along the tube 1238, i.e., no air is drawn in by the prime mover 140 until the fluid 122 is consumed. This design has the advantage of using nearly 100% of the medication loaded into the tube 1238. This configuration has the further advantage of allowing the device 100 to operate in any orientation, even in zero gravity environments. Referring to FIG. 7, a clear window 1245 and a numerical scale 1246 on the side of the cartridge 1237 may indicate how many doses remain in the reservoir 1236. The scale 1246 may be read with the device 100 in any orientation.

While a design of a reservoir 120 with a collapsible bladder 1220 and a design of a reservoir 1236 with a coiled tube 1238 are shown, those skilled in the art will recognize that other designs of reservoirs may be used.

Optionally, as shown in FIG. 5, a heater 1248 may be incorporated into the reservoir 120 to heat the fluid 122. The heater 1248 is preferably either an inductance or a resistive heater that is electrically connected to a contact 1249 in the wall of the reservoir 120 that is electrically connectable to a contact (not shown) in the body 130 to provide electrical power to the heater 1248 to heat the fluid 122 in the reservoir 120. However, for many ophthalmic medicines, heating the medicine is not desired, and those skilled in the art will recognize that the heater 1248 may be omitted in its entirety.

Also optionally, a low level sensor 1250, shown in FIG. 3, may be incorporated into the reservoir 120 to indicate when the fluid 122 in the reservoir 120 is almost depleted. The sensor 1250 is electronically connected to the system controller 190 via electrical connection 1252 to provide an indication of fluid level in the reservoir 120. The sensor 1250 may be electronically connected to an alarm, such as an optical or aural indicator, such as a blinking light or an audible alarm.

Body

Referring back to FIG. 2, the body 130 houses the prime mover 140 and provides a connection for the fluid reservoir 120 and for the nozzle assembly 150 to engage the prime mover 140. The body 130 includes, at the distal end of the body 130, a bushing 131 that is securely bonded to the body 130, such as by an adhesive or a snap-fit. The bushing 131 includes at least one, and preferably, a plurality of bayonet clips 131*a* that are adapted to snap into the nozzle assembly 150 to retain the nozzle assembly 150 onto the body 130.

The body 130 preferably includes a connection device, such as an orifice 132, for attaching to the handle portion 160. However, those skilled in the art will recognize that other connection methods, such as snap fit, bayonet clips, or other suitable mechanisms known to those skilled in the art may be used. Preferably, the body 130 connects to the top 162 of the handle portion 160 in only a single orientation so that electrical contacts in each of the body 130 and the handle portion 160 properly engage each other when the head portion 110 is connected to the handle portion 160.

The body 130 also includes, at the proximal end of the body 130, a collar spacer 133 that is fixedly connected to the body 130 to provide optimum spacing of the proximal end 142 of the prime mover 140 within the reservoir 120 to optimize the ability of the prime mover 140 to withdraw the fluid 122 from the reservoir 120 during operation of the device 100.

The body 130 houses the prime mover 140, and provides connection means for the reservoir 120, the nozzle assembly 150, and the handle portion 160. The retainer 135 is fixedly connected to the body 130 and also releasably retains the reservoir 120 so that the reservoir 120 is removable from the remainder of the device 100. As described above, the retainer 135 may include an engagement surface, or alternatively, other connection means, such as threaded connections, or other means known to those skilled in the art.

The body 130 includes a generally tubular passage 136 that is sized to accept the proximal end 142 of the prime mover 140. A spacer recess 137 is disposed at the distal end of the body 130, preferably below the passage 136. The spacer recess 137 is used to releasably retain a targeting means, which will be described in detail later herein.

A seal 138 is disposed about the proximal end of the passage 136. The seal 138 prevents any fluid 122 from leaking out of the reservoir 120 when the reservoir 120 is attached to the body 130. In the present embodiment, the seal 138 is formed in the shape of a ring by injection molding or liquid injection molding using medical grade silicones or urethanes with durometers in the range of 5 to 30 Shore A.

Preferably, the body 130 includes an activation indicator 1310 that is disposed on the top of the body 130. The activation indicator 1310 may be a light, such as an LED, that provides constant illumination as long as the activation switch 180 is depressed; a light that provides blinking illumination; a sound that provides audible indication, either by constant or by periodic beeping; some combination of these listed indicators, or some other indication that would indicate to the user that the device is ready for operation. The activation indicator 1310 operates when the activation switch 180 is initially depressed by the user. The activation indicator 1310 alerts the user that the device 100 is "ON" and is about to spray the fluid 122 from the nozzle assembly 150. The activation indicator 1310 is electronically connected to the system controller 190 via electrical leads (not shown).

The body 130 may be machined from solid metal or plastic stock, or may be injection molded with polymer resins such as ABS, styrene, PVC, or other suitable material, as will be recognized by those skilled in the art. The body 130 may be injection molded or manufactured by other methods known by those skilled in the art. Preferably, the body 130 has a durometer within the range of approximately 90 to 100 Shore A.

Prime Mover

Figure 9:
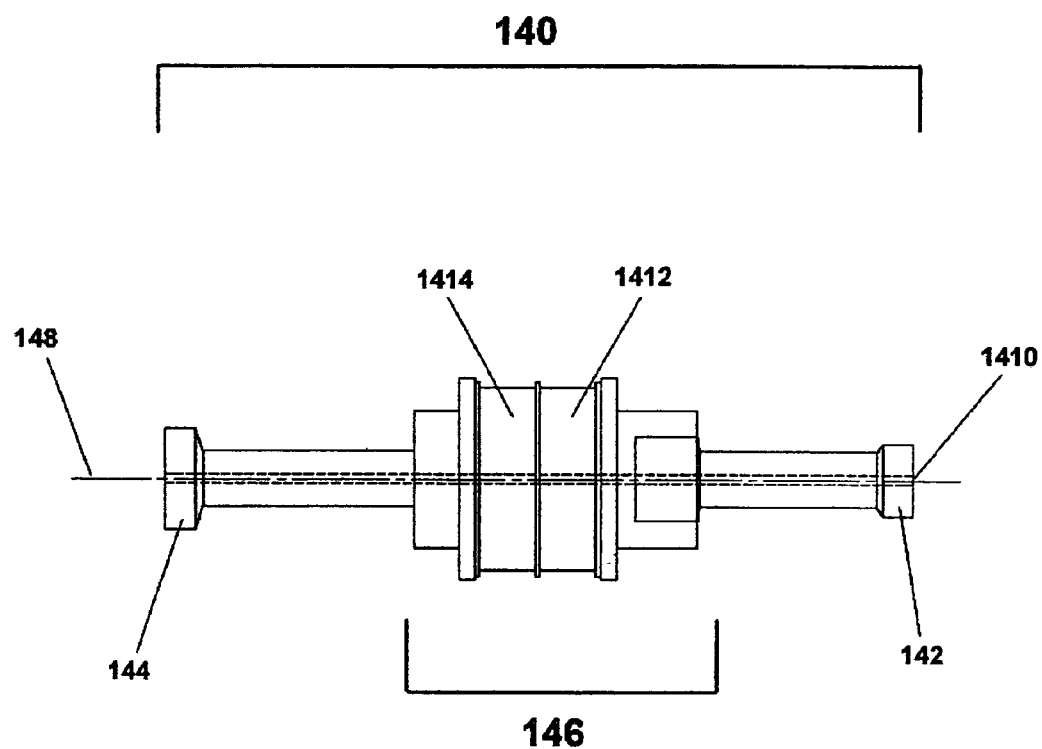
FIG. 9 is an enlarged side view, in section, of a prime mover inserted into the device.
Figure 10:
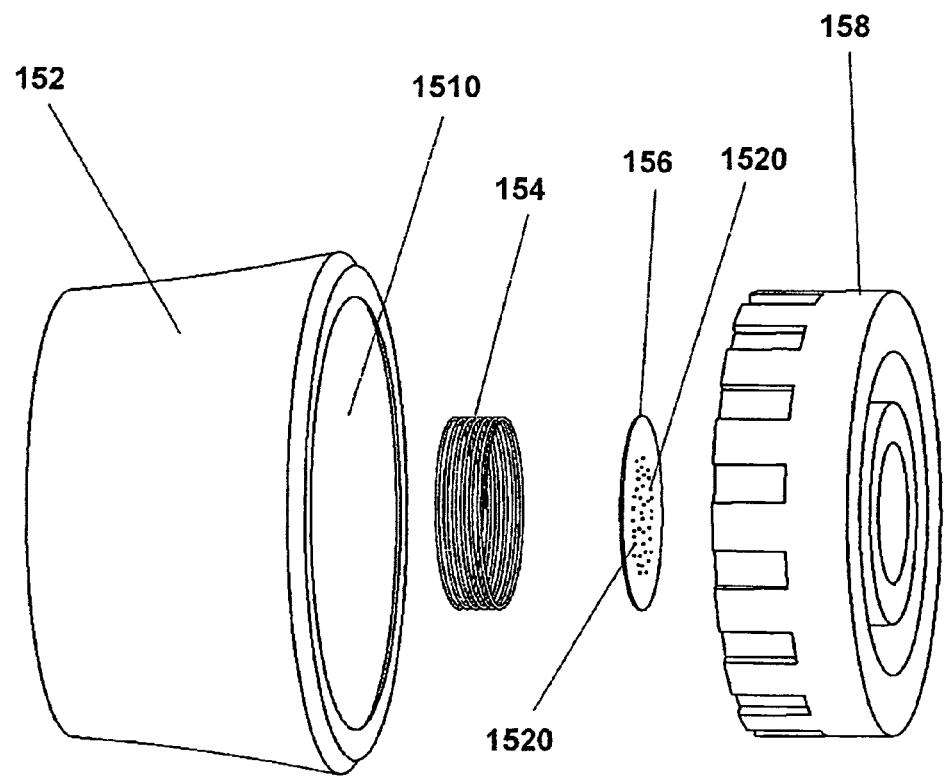
FIG. 10 is an enlarged exploded perspective view of a nozzle assembly of the device.
Figure 11:
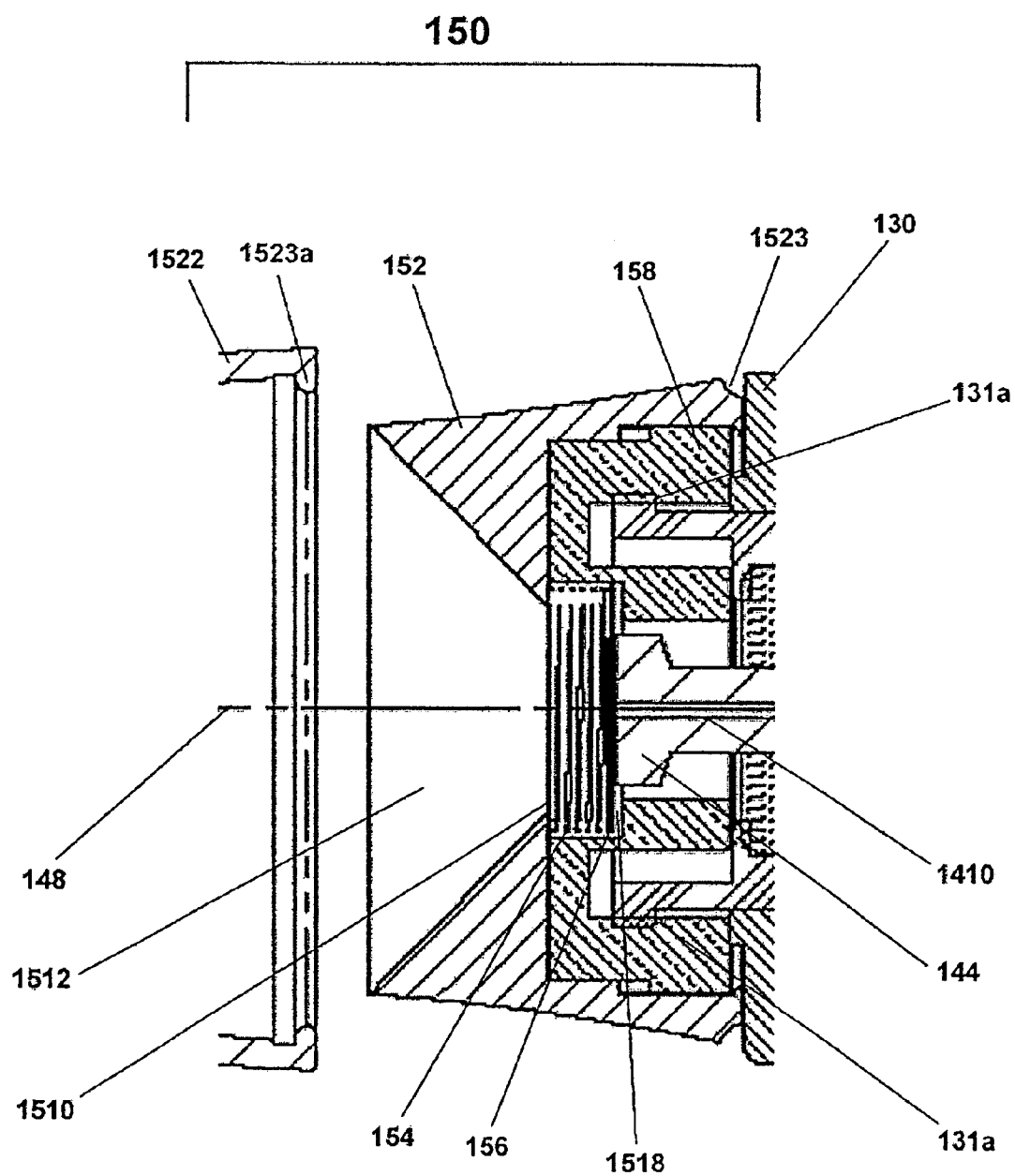
FIG. 11 is an enlarged side view, in section, of the nozzle assembly of the device.

Referring still to FIG. 2, as well as to FIG. 9, the prime mover 140 will now be described. The prime mover 140 is shown in FIG. 2 in relation to the nozzle assembly 150 and the reservoir 120. The prime mover 140 is preferably an ultrasonic oscillator formed by a piezoelectric assembly such as that found in the Omron Micro-Air model NE-U03. The NE-U03 is a commercially available nebulizer that is typically used in nebulizers for bronchial therapy. However, the inventors of the present invention have discovered that this particular nebulizer is also suited for delivery of ophthalmic medicine to satisfy the needs that the present invention is intended to satisfy. The preferred piezoelectric assembly is described in detail in U.S. Pat. No. 6,651,650, the disclosure of which is incorporated herein by reference. However, those skilled in the art will recognize that the NE-U03 may be substituted for other piezoelectric assemblies, such as those discussed in the article *Nebulizers that Use a Vibrating Mesh or Plate with Multiple Aperatures to Generate Aerosol*, by Rajiv Dhand MD, Respiratory Care, December 2002, Vol. 47, No. 12, which is also incorporated by reference herein. Alternatively, instead of using piezoelectric assemblies, those skilled in the art will recognize that other prime movers that are not piezoelectrically operated may be used. Examples of such other suitable prime movers include electric pumps, manual pumps, compressed gas, or other suitable prime movers, as will be recognized by those skilled in the art.

The prime mover 140 includes a proximal end 142, a distal end 144, and a central portion 146 disposed between the proximal end 142 and the distal end 144. A longitudinal axis 148 extends along a length of the prime mover 140 between the proximal end 142 and the distal end 144. A longitudinally extending lumen 1410 extends along the longitudinal axis 148 and extends the length of the prime mover 140. Preferably, a perpendicular cross section of the lumen 1410 is generally circular in shape and has a diameter of approximately between 0.25 and 1.0 mm. However, those skilled in the art will recognize that the lumen 1410 may have other cross sectional shapes, such as a generally oblong, oval, or elongated shape.

The central portion 146 includes at least two generally annular piezoelectric elements 1412, 1414 that surround the lumen 1410. The piezoelectric elements 1412, 1414 are electrically connected to the power source 170, which drives the piezoelectric elements 1412, 1414 during operation of the device 100.

Referring to FIG. 2, the prime mover 140 is retained within the body 130 by a distal seal 1426. The distal seal 1426 is generally annular in shape and taper from a wider diameter to a smaller diameter from the piezoelectric elements 1412, 1414 toward the proximal end 142 and the distal end 144, respectively. The distal seal 1426, along with the seal 138, restricts movement of the prime mover 140 within the body 130 and prevent fluid 122 that may leak through the device 100 from engaging the central portion 146 of the prime mover 140. Preferably, the seal 1426 is constructed from a biocompatible material, such as medical grade silicon or urethane, although those skilled in the art will recognize that other suitable material may be used.

Figure 12A:
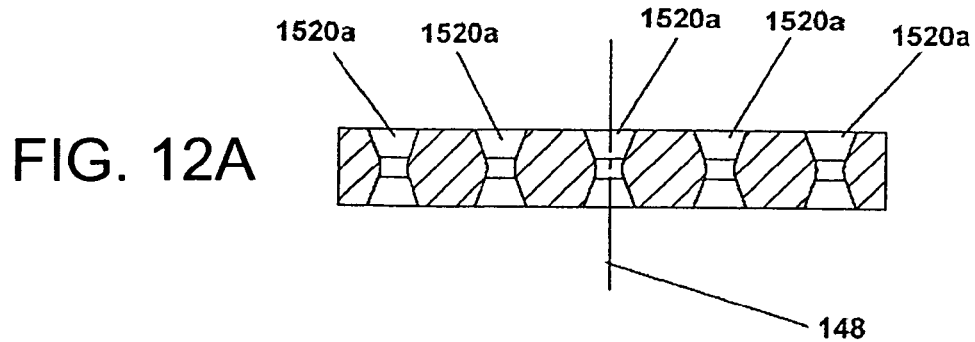
FIG. 12*a* is an enlarged partial sectional view of a first embodiment of the mesh plate of the nozzle assembly.
Figure 12B:
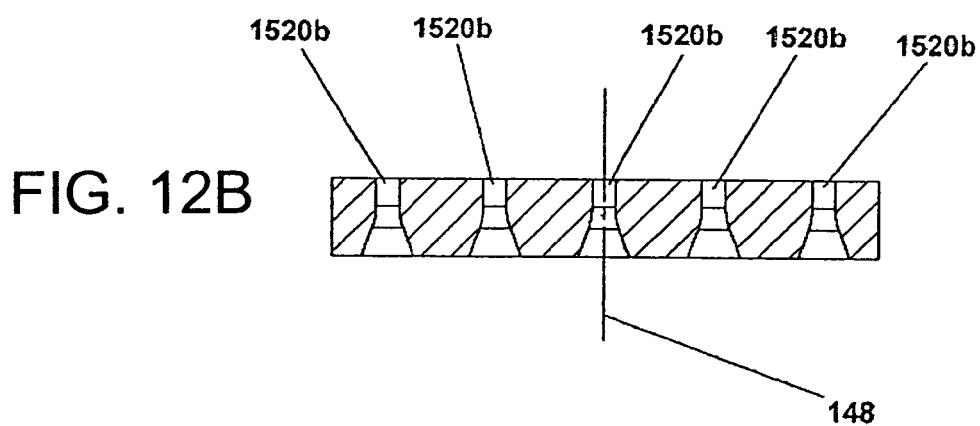
FIG. 12*b* is an enlarged partial sectional view of a second embodiment of the mesh plate of the nozzle assembly.
Figure 12C:
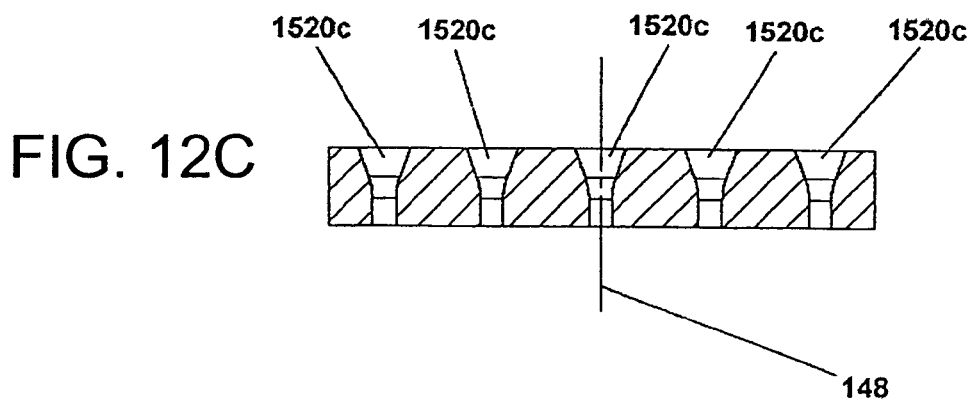
FIG. 12*c* is an enlarged partial sectional view of a third embodiment of the mesh plate of the nozzle assembly.
Figure 12D:
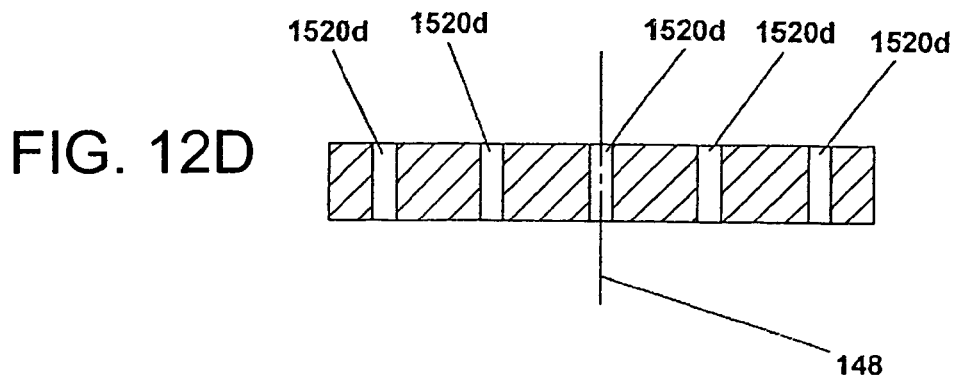
FIG. 12*d* is an enlarged partial sectional view of a fourth embodiment of the mesh plate of the nozzle assembly.
Figure 14:
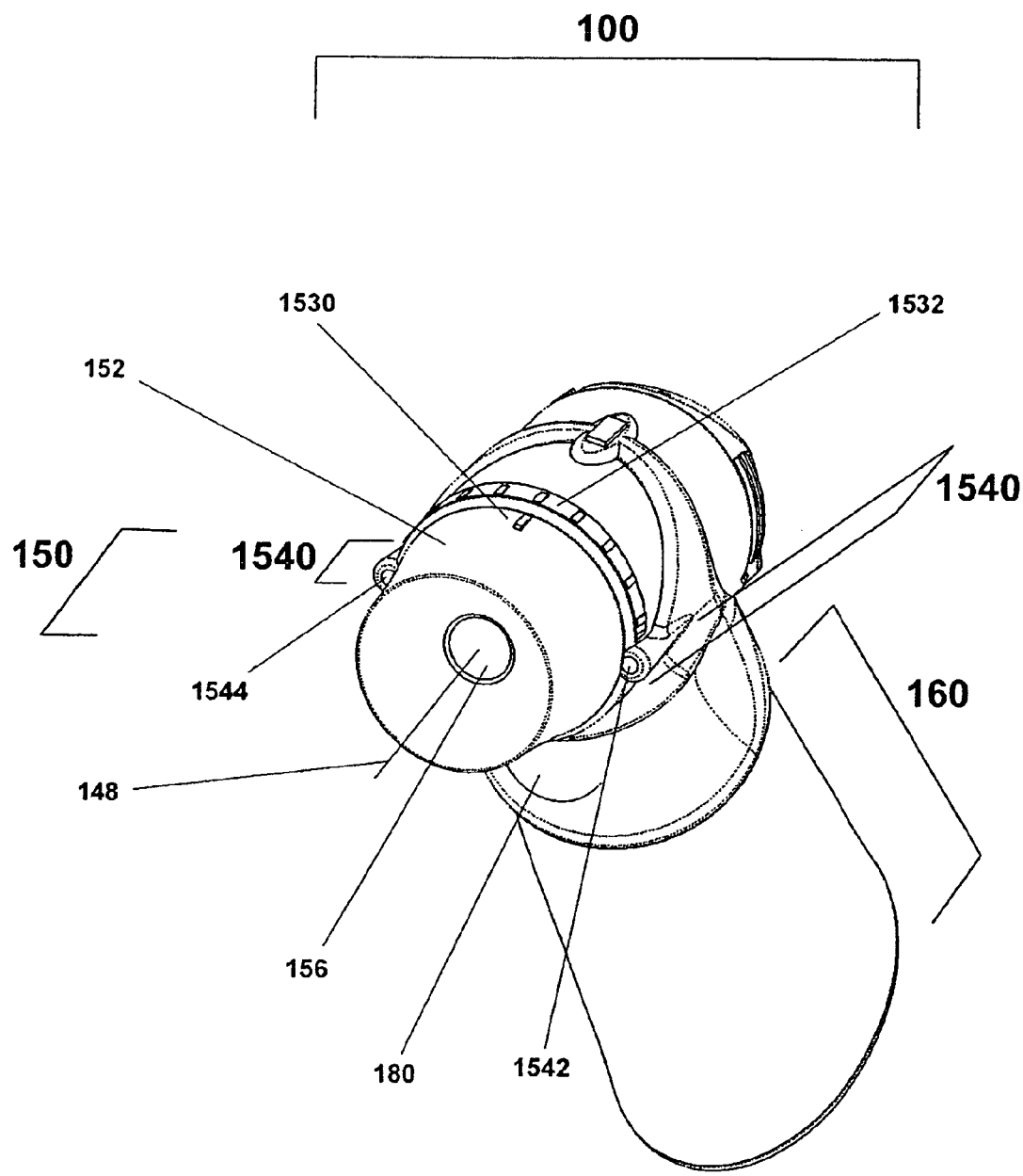
FIG. 14 is a perspective view of the device showing an optional dosage adjustment feature.

Referring back to FIG. 3, the proximal end 142 is immersed in the fluid 122 in the reservoir 120. When the piezoelectric elements 1412, 1414 are excited, such as during operation of the device 100, standing waves are formed which draw the fluid 122 into the proximal end 142 of the prime mover 140 and along the lumen 1410. The standing waves propel the fluid 122 along the lumen 1410 to the distal end 144 of the prime mover 140 and to the nozzle assembly 150, which is in mechanical contact with the distal end 144 of the prime mover 140. As the prime mover 140 vibrates at ultrasonic frequencies, the prime mover 140 transfers a portion of its vibrational power to a mesh plate 156 in the nozzle assembly 150, as will be described in more detail later herein. The fluid 122 that has been propelled along the lumen 1410 contacts the mesh plate 156. The vibration of the plate 156 aerosolizes the fluid 122 and accelerates the fluid 122 away from the device 100 and toward the patient.

Nozzle Assembly

The nozzle assembly 150 is shown in an exploded perspective view in FIG. 10, as well as in an elevated sectional view in FIG. 11. The nozzle assembly 150 forms the mist that is discharged from the device 100 during operation. The nozzle assembly 150 includes, from a distal to a proximal direction, a cap 152, a biasing member 154, a mesh plate 156, and a retainer 158.

The cap 152 is generally annular, with a central opening 1510 disposed along the longitudinal axis 148. Preferably, the body of the cap 152 extends in a distal direction and generally away from the longitudinal axis 148 to form a concave volume 1512 distal of the central opening 1510. The concave volume 1512 reduces the likelihood that a foreign object, such as a user's finger, will touch the mesh plate 156, potentially contaminating the plate 156.

The cap 152 preferably includes a releasable lock feature, such as a female threaded connection (not shown) that releasably threadingly engages the retainer 158, which has a mating twist lock feature, such as a mating male threaded connection (not shown). However, those skilled in the art will recognize that the cap 152 may engage with the retainer 158 by other means not shown, such as by snap engagement, bayonet means, or other suitable means known to those skilled in the art.

The mesh plate 156 is biased against the distal end 144 of the prime mover 140 by the biasing element 154, such as a helical spring, that is disposed between the cap 152 and the mesh plate 156. The biasing element 154 ensures that the mesh plate 156 is firmly engaged with the distal end 144 of the prime mover 140 to provide proper dispersion of the fluid 122 through the mesh plate 156 during operation of the device 100. While a helical spring is preferred as the biasing element 154 because a helical spring provides a generally uniform biasing force around its perimeter, those skilled in the art will recognize that other types of biasing elements, such a leaf springs, may be used instead. As shown in FIG. 11, a clearance space 1518 is formed between the proximal side of the mesh plate 156 and the retainer 158 to allow the mesh plate 156 to vibrate during operation.

The mesh plate 156 is formed of a rigid material that is biocompatible and non-oxidizing, such as alumina ceramics, titanium allows, or stainless steel alloys. As shown in FIG. 10, an array of openings 1520 is formed in the mesh plate 156. The number, density, size, and shape of the openings 1520 contribute to determining mist parameters such as volume, velocity, and droplet size distribution. The openings 1520 may be drilled by mechanical means, by fine jets of water, or by lasers. The preferred embodiment of the mesh plate 156 is constructed from a ceramic material and measures approximately 9 mm in diameter and 0.1 mm thick, having between 500 and 5000 openings 1520 drilled by laser. The openings 1520 preferably have diameters in the range of approximately 0.5 to 30 microns. A mask (not shown) may be used that enables many openings 1520 to be drilled simultaneously. After each group of openings 1520 is drilled, the mask or the mesh plate 156 is indexed to a new position and the next set of openings 1520 is drilled. This step-and-repeat process continues until all the openings 1520 are made.

Enlarged cross sections of several embodiments of openings 1520*a*, 1520*b*, 1520*c*, 1520*d*, and 1520*e* in mesh plates 156*a*, 156*b*, 156*c*, 156*d*, 156*e* are shown in FIGS. 12*a*, 12*b*, 12*c*, 12*d*, 12*e*. Referring to FIG. 12*a*, the mesh openings 1520*a* in the mesh plate 156*a* are preferably circular in cross section along a plane parallel to the longitudinal axis 148, with an approximate hourglass cross section along a plane perpendicular to the longitudinal axis 148. Referring to FIG. 12*b*, the mesh openings 1520*b* in the mesh plate 156*b* are wider at the proximal (bottom) end of the plate 156*b* and narrower at the distal (top) end of the plate 156*b*. Referring to FIG. 12*c*, the mesh openings 1520*c* in the mesh plate 156*c* are narrower at the proximal (bottom) end of the plate 156*c* and wider at the distal (top) end of the plate 156*c*. Referring to FIG. 12*d*, the mesh openings 1520*d* in the mesh plate 156*d* have a generally constant diameter between the proximal (bottom) end of the plate 156*d* and the distal (top) end of the plate 156*d*.

The mesh plate may 156 incorporate one of several designs of openings 1520 as shown in FIGS. 13*a* through 13*e*. In the top plan view of the design shown in FIG. 13*a*, a mesh plate

156*e* is generally planar, with a plurality of openings 1520 in a generally circular pattern, with a center of the generally circular pattern along the longitudinal axis 148. In the top plan view of the design shown in FIG. 12*b*, a mesh plate 156*f* is generally planar, with a plurality of openings 1520 in a generally elongated pattern, such as a rectangle or an oval. Alternatively, a mesh plate 156*g* may be generally convex, as shown in the side sectional view of the mesh plate 156*g* in FIG. 13*c*, to disperse the fluid 122 at a relatively wide angle to increase the field of dispersion of the fluid 122. In yet another alternative, a mesh plate 156*h* may be concave, as shown in the side sectional view in FIG. 13*d*, to disperse the fluid 122 in a relatively small area. For each of the mesh plates 156*g*, 156*h* in FIGS. 13*c* and 13*d*, the pattern of openings may be circular, as shown in FIG. 13*a*, or elongated, as shown in FIG. 13*b*. The pattern of openings 1520 is aligned with the central opening 1510 in the cap 152 so that the fluid 122 that is dispersed through the mesh plate 156 passes through the central opening 1510 and forms a mist for deposition into the eye of the patient.

In an alternate embodiment, shown in FIG. 13*e*, a mesh plate 156*i* includes a generally flat plate with openings 1520*i* that are angled toward the longitudinal axis 148. This design provides the benefits of an easy to produce mesh plate that directs the fluid to a focused point.

It is preferred that the openings 1520 in the mesh plate 156 generates mist particle sizes in the average range of between approximately 0.5 and 10 microns in diameter. It is also desired that the mist generated through the nozzle assembly 150 preferably extends about 7.5 to 10 cm in a mist plume diverging with a solid angle of approximately 10-20 degrees and traveling at a velocity of between approximately 4 and 30 cm per second, discharging approximately between 2 and 20 microliters per second, and preferably, between 7 and 10 microliters of fluid per second.

Referring back to FIG. 11, the retainer 158 preferably connects to the body 130 via the plurality of bayonet fittings 131*a* that snap into the retainer 158, although those skilled in the art will recognize that other means for connecting the retainer 158 to the body 130, such as by threaded connection, adhesive, or other suitable means, may be used.

The mesh plate 156 is removable from the remainder of the device 100 for cleaning, such as in an alcohol or other cleaning solution. To clean the mesh plate 156, the retainer 158 is removed from the body 130, releasing the cap 152, the biasing element 154, the mesh plate 156, and the retainer 158 from the remainder of the device 100. The biasing element 154 biases the mesh plate 154 against the retainer 158, keeping the nozzle assembly 150 intact. After cleaning, the nozzle assembly 150 is reconnected to the remainder of the device 150. The distal end 144 of the prime mover 140 engages the mesh plate 156, forcing the mesh plate 156 away from the retainer 158 so that the mesh plate 156 may be able to vibrate when excited by the prime mover 140.

Optionally, as shown in FIGS. 2 and 11, an overcap 1522 may be disposed over the distal end of the cap 152 to keep the mesh plate 156 clean between uses. The cap 152 may include a peripherally spaced groove 1523 that is engageable with a corresponding protuberance 1523*a* for a snap fit connection that securely retains the overcap 1522 onto the cap 152, yet allows the overcap 1522 to be removed from the cap 152 with a minimum of effort. Alternatively, the overcap 1522 may attach to the cap 152 with a snap action, a thread, a bayonet, or other simple fastening means. The overcap 1522 may be machined from solid metal or plastic stock, or may be injection molded with polymer resins such as ABS, styrene, or PVC. The overcap 1522 may optionally be tethered to the device 100 with a lanyard made of wire cable or plastic filament. Alternatively, the overcap 1522 may be attached to the nozzle assembly 150 with a hinge (not shown). The hinge may incorporate a spring or other biasing member that automatically retracts the overcap 1522 away from the distal end of the cap 152 when a latch is released.

Dosage Adjustment

Different medications and/or ophthalmic treatment regimens may require different amounts of a medication to be administered with each use of the device 100. Alternatively, a larger patient may need a larger dose of a medication than a smaller patient. Therefore, an ability to adjust dosage amount may be required. The device 100 may optionally be equipped with user-accessible adjustments for flow rate (mist volume) and total flow (dose). These adjustments may be electromechanical (knobs or wheels operating potentiometers), or electronic (buttons or keys providing digital data to the system controller 190).

In one embodiment of a dosage adjustment, a dosage adjuster 1530, 1530*a* may be disposed on the nozzle assembly 150, such as is shown in FIGS. 14 and 15*a*-15*b*. The dosage adjuster 1530 includes a potentiometer 1532 rotatably connected to the cap 152. The potentiometer 1532 may include an infinitely positionable pot that is movable across a resistive film 1536, as shown in FIG. 15*a*, or a discretely positionable pot that is movable across a resistive film 1538 as shown in FIG. 15*b*. For either film 1536, 1538, rotation of the potentiometer 1532 changes the resistance of the potentiometer circuit, as is well known to those skilled in the art. The change in resistance changes a dosage voltage signal that is transmitted to the system controller 190 via a circuit (not shown). The system controller 190 interprets the voltage signal received and in turn transmits an operation duration signal to the prime mover 140, which controls the amount of time that the prime mover 140 operates when the activation switch 180 is engaged, thereby controlling the amount of fluid 122 that is discharged from the device 100.

While the dosage adjuster 1530 may be disposed on the nozzle assembly 150 as shown, those skilled in the art will recognize that a dosage adjuster 1530*a* may be disposed on the handle portion 160, as is alternately shown in FIG. 15*c*. The dosage adjuster 1530*a* preferably operates similarly to the dosage adjuster 1530 described above. Preferably, the dosage adjuster 1530*a* is disposed in an inconvenient location, such as behind a panel (not shown). It is typically not desirable to be able to easily adjust the dosage adjuster 1530*a* so that the user does not accidentally adjust the dosage while picking up or holding the device 100. The flow rate of fluid 122 dispensed as a mist from the device 100 is preferably adjustable between about 10 to 100 microliters/sec.

In order to ensure that dosing is consistent, the location of the nozzle assembly 150 relative to the eye during dispensing of medication may also need to be controlled. Various targeting mechanisms have been developed for this purpose. Referring back to FIG. 14, a first embodiment of a targeting mechanism 1540 may be incorporated into the nozzle assembly 150. The targeting mechanism 1540 is used to provide the user with an optimum distance to space the nozzle assembly 150 from the patient's eye to maximize effectiveness of the device 100. The targeting mechanism 1540 includes two projection lenses 1542, 1544 that are disposed on the nozzle assembly 150, preferably spaced 180 degrees from each other on either side of the longitudinal axis 148. The lenses 1542, 1544 are angled toward the longitudinal axis 148 such that projections from the lenses 1542, 1544 intersect at the longitudinal axis 148 at an optimum distance for spacing the nozzle assembly 150 from the patient's eye, as shown in FIG. 16. A light source 1546, 1548 is disposed proximate to each lens 1542, 1544, respectively, with each light source 1546, 1548 being directed along the projection line of each respective lens 1542, 1544. The light sources 1546, 1548 may be LEDs, incandescent sources, lasers, or other suitable light source, as will be recognized by those skilled in the art. The light sources 1546, 1548 are electrically connected to the activation switch 180 so that the light sources 1546, 1548 activate upon initial engagement of the activation switch 180.

Figure 16:
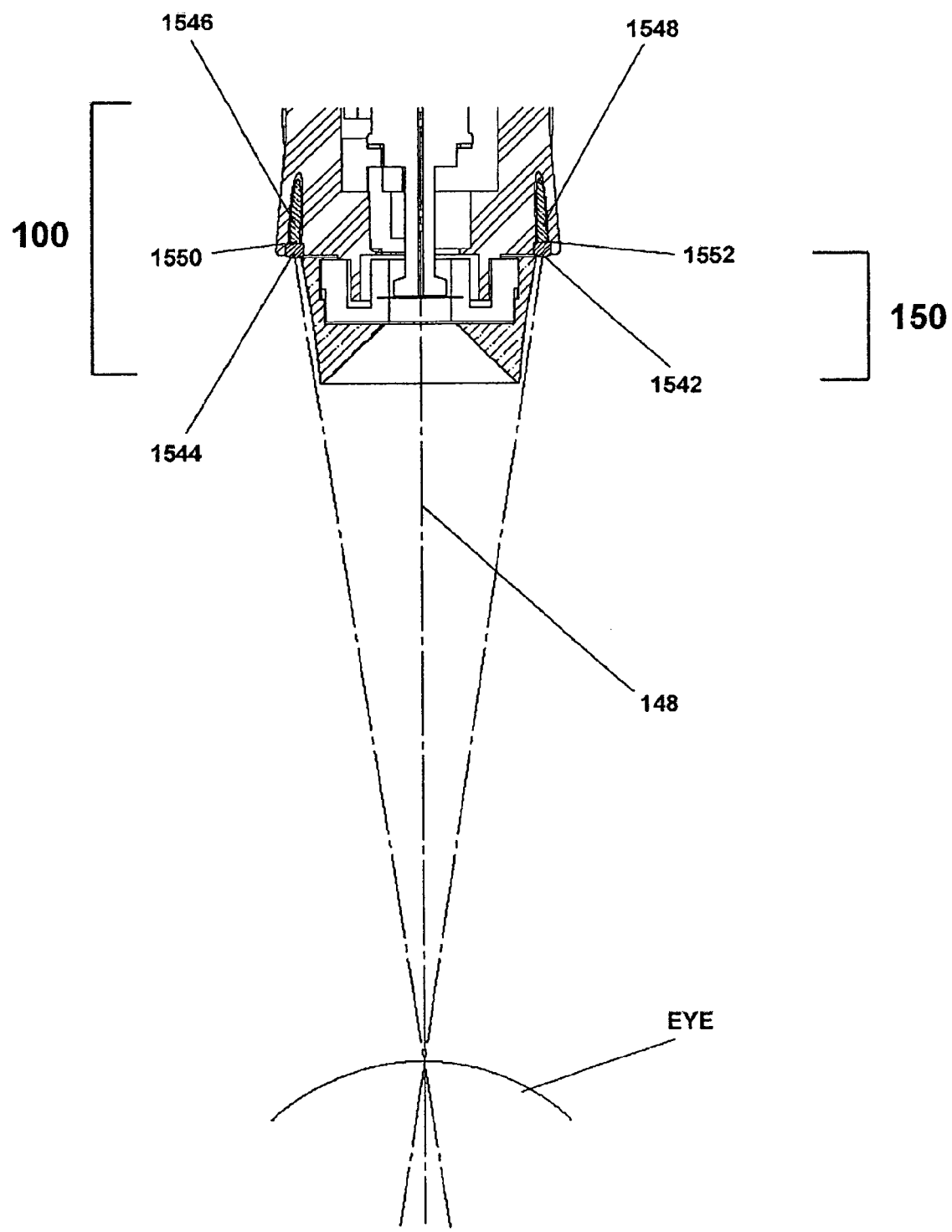
FIG. 16 is a top plan view showing the targeting device of FIG. 14.

Preferably, the light sources 1546, 1548 and the lenses 1542, 1544 form a pattern on the target eye when the device 100 is aimed at the eye and the activation switch 180 is depressed. The pattern may be formed by separate masks 1550, 1552 that are disposed between each light source 1546, 1548 and its respective lens 1542, 1544, as shown in FIG. 16, or, alternatively, the mask may be formed on each lens 1542, 544 (not shown). In either embodiment, the targeting mechanism 1540 forms one of three general patterns on the iris or the sclera of the eye. When the device 100 is too far from the eye, a pattern similar to a pattern formed in one of FIGS. 17a, 18a, 19a, 20a, 21a is formed. When the device 100 is a correct distance from the eye, a pattern similar to the pattern formed in one of FIGS. 17b, 18b, 19b, 20b, 21b is formed. When the device 100 is too close to the eye, a pattern similar to the pattern formed in one of FIGS. 17c, 18c, 19c, 20c, 21c is formed. Those skilled in the art will recognize that the patterns shown in FIGS. 17a-21c are exemplary only, and that numerous other patterns may be formed.

In addition to assisting in determining the optimum distance for spacing the device 100 from the eye, the targeting mechanism 1540 also aids in accurately aiming the device 100 at the eye, so that the mist generated by the device 100 is directed toward the middle of the eye, and not off to the side.

While the targeting mechanism 1540 described above is useful for a professional practitioner to use to aim the device 100 at a patient, those skilled in the art will recognize that an alternative embodiment of a targeting mechanism (not shown) may be used to by a patient on himself/herself by directing the targeting mechanism onto his/her retina.

Handle Portion

Figure 15A:
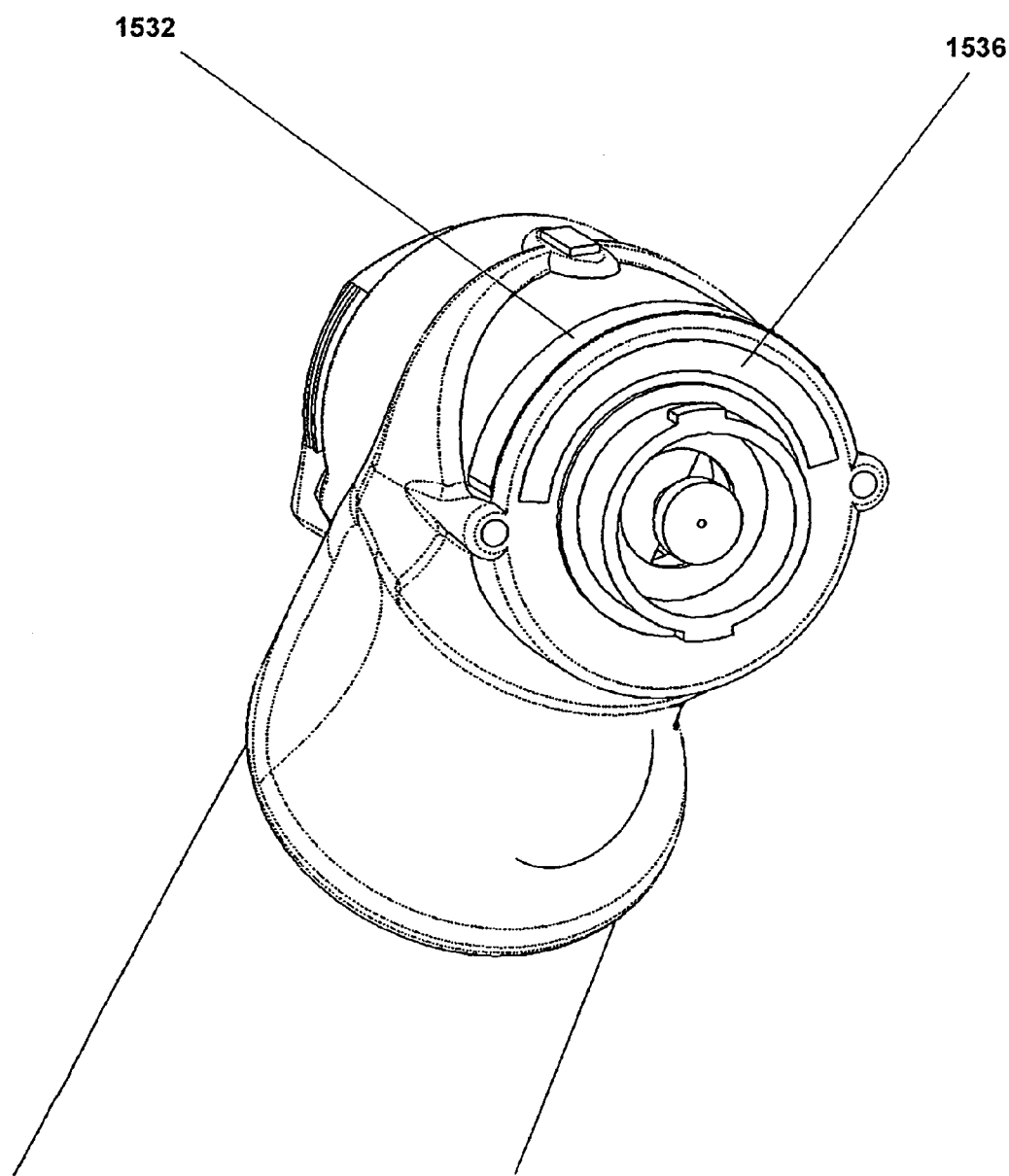
FIG. 15*a* is a perspective view of the device showing a first embodiment of the dosage adjustment feature.
Figure 15B:
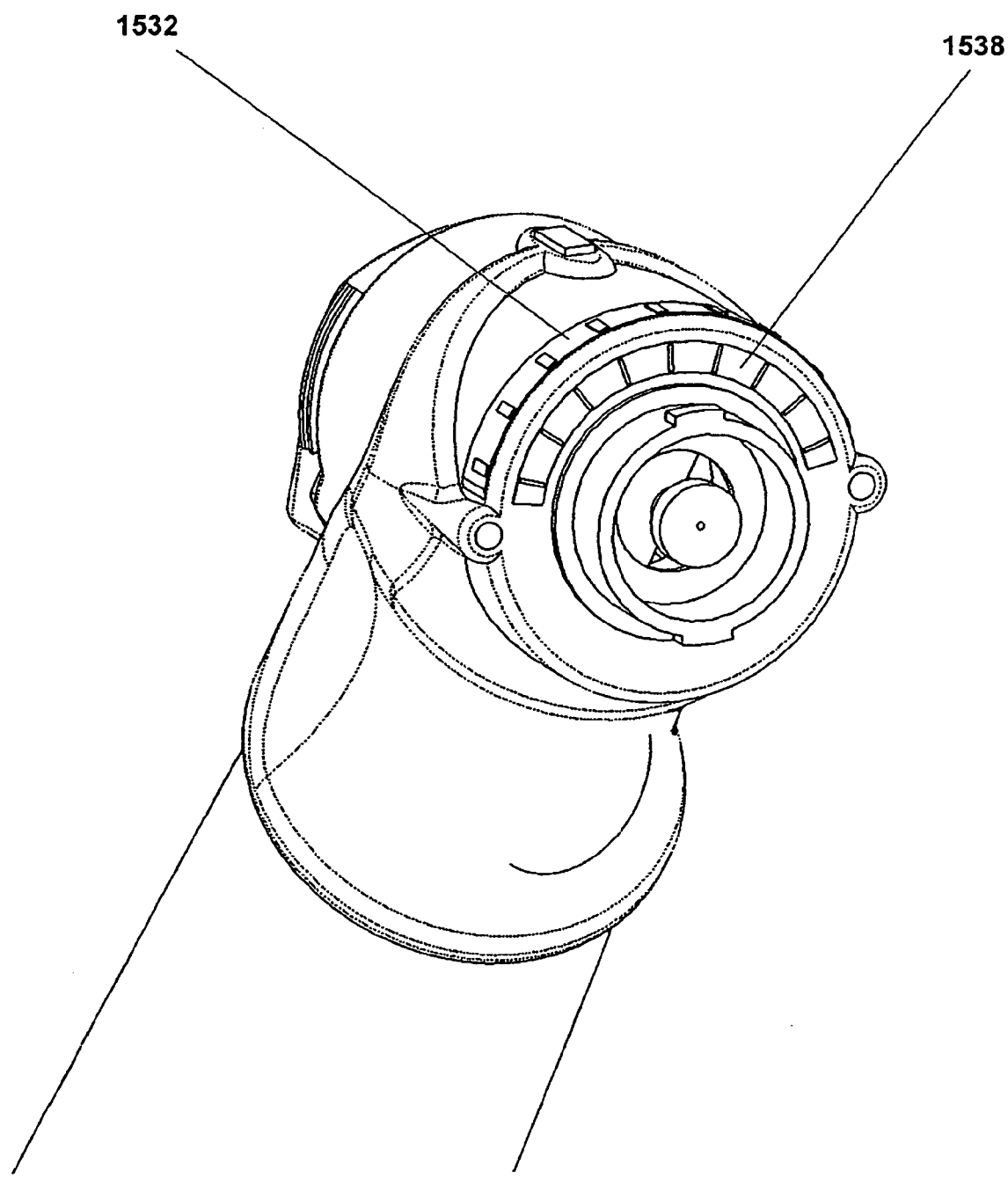
FIG. 15*b* is a perspective view of the device showing a second embodiment of the dosage adjustment feature.
Figure 15C:
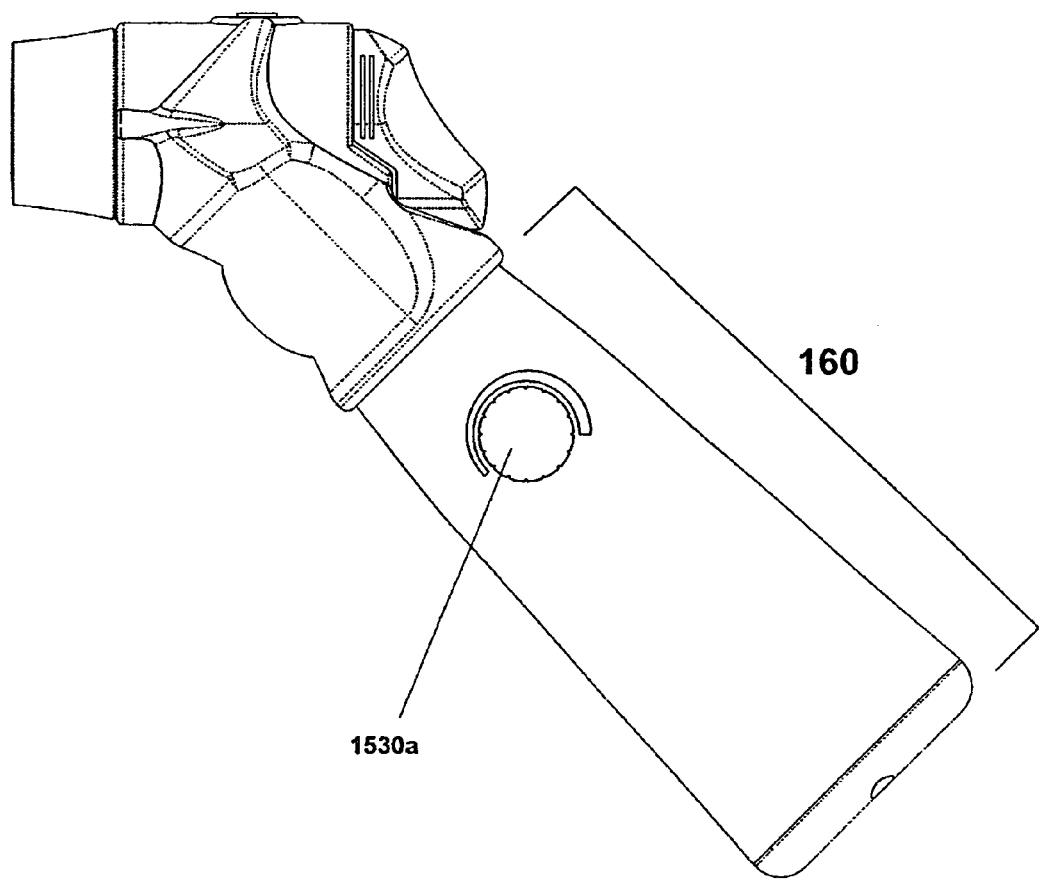
FIG. 15*c* is a perspective view of the device showing a third embodiment of the dosage adjustment feature.

Referring back to FIGS. 1 and 2, the handle portion 160 contains the bulk of the electronics, as well as the activation switch 180 and the power supply 170. As described previously above, the handle portion 160 may also include a dosage adjuster 1530a (shown in FIG. 15c) for adjusting the amount of fluid 122 that is discharged per use. The handle portion 160 includes an elongated body 162 having a top end 164, which is connected to the body portion 130, as well as a bottom end 165, which is configured for removable insertion into a base 166.

In a non-use operation, the device 100 is preferably disposed in the base 166, as shown in FIGS. 1 and 2. The base 166 typically rests on a desktop and holds the device 100 such that the device 100 can simply be lifted from the receiver for use. The base 166 includes a cavity 167 that is sized and shaped to securely receive the bottom end 165 of the handle portion 160. The base 166 may also be weighted to keep the device 100 from toppling over after the device 100 is inserted into the base 166. Alternately, the base 166 may include an adhesion device, such as a suction cup or an adhesive (not shown), to keep the device 100 from toppling over.

Preferably, the handle portion 160 and the base 166 may be separately machined from solid metal or plastic stock, or may be injection molded with impact resistant polymer resins, such as ABS, polycarbonate, PVC, or other suitable material, as will be recognized by those skilled in the art. The handle portion 160 may optionally include a rubberized grip 168, at least along a length of the handle portion 160 facing the distal end of the device 100. The rubberized grip 168 is softer for the user and helps prevent the user from accidentally dropping the device 100. The grip 168 may also include indentations for a user's fingers to enhance ergonomics. The grip 168 may be manufactured from a material having a hardness in the range of 10-50 Shore A that may be molded separately and bonded onto the handle portion 160.

Figure 22A:
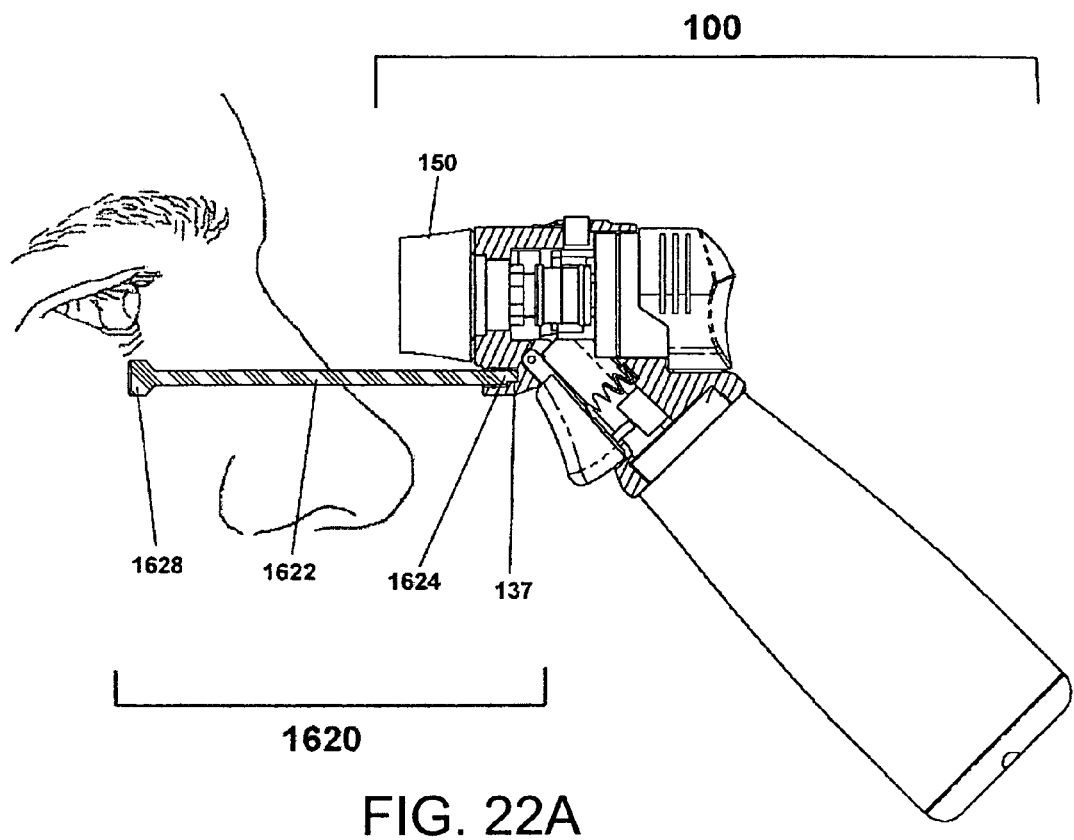
FIG. 22*a* is a side elevational view of a mechanical targeting device according to the present invention.
Figure 22B:
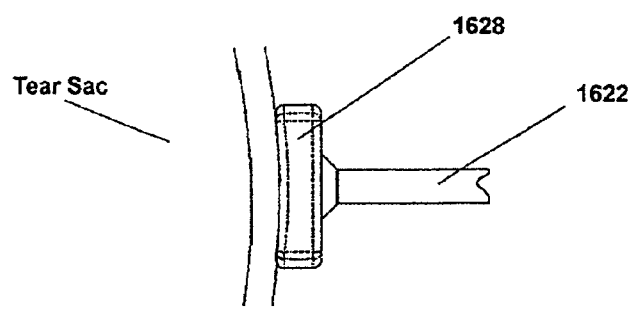
FIG. 22*b* is a top plan view of a proximal end of the mechanical targeting device shown in FIG. 22*a*, being used on a patient.

Referring now to FIGS. 22a and 22b, an optional mechanical targeting means 1620, for setting an optimum distance between the nozzle assembly 150 and the patient's eye, is shown. In lieu of the electronic targeting means 1540 shown and described with respect to FIGS. 14 and 17a-21c, the targeting means 1620 may be mechanically incorporated into the device 100.

The targeting means 1620 includes a generally elongated member 1622 that includes a connected end 1624 that is releasably inserted into the spacer recess 137, and a free end 1628 that is disposed away from the connected end 1624. As shown in FIG. 22b, the free end 1628 is generally "Tee-shaped" and is preferably formed in the shape of an eyelid depressor to depress the tear sac under the eye and to provide a larger ocular surface area for contact with the fluid 122 being dispensed from the device 100. Since the free end 1628 engages the patient and the patient's eye area, it is preferred that the targeting means 1620 is disposable between uses to avoid any contamination from one patient to the next.

Preferably, the elongated member 1622 is constructed from impact resistant polymer resins, such as ABS, polycarbonate, PVC, or some other suitable rigid material to minimize deflection of the elongated member 1622 during operation. Also preferably, the free end 1628 is either coated with or constructed from a soft material, such as rubber in order to reduce the likelihood of eye injury in the event that the free end 1628 accidentally engages the eye.

Power

A preferred power source 170 for the device 100 is battery power. As can be seen in FIGS. 1 and 2, a battery 172 is removably inserted into the bottom end 165 of the handle portion 160. A cover 169 retains the battery 172 in the handle portion 160. The cover 169 is removable so that the battery 172 may be easily replaced. The cover 169 may be releasably connected to the handle portion 160 by clips, threaded fasteners, or other means known to those skilled in the art.

The battery 172 may be a single-use lithium ion or alkaline type, or the battery 172 may be rechargeable lithium-ion, nickel-cadmium, nickel-metal-hydride, or other battery type. The battery 172 may be a single battery or a plurality of batteries electrically connected in series. For example, two lithium photo batteries NEDA/ANSI type CR2 (e.g. Duracell Ultra CR2 Li/MnO2) may be connected in series and used to power the device 100. The batteries 172 are preferably rated for 3V and approximately 2000 mAh. The batteries 172 are connected in series to provide a total capacity 200 mAh at 6V. The batteries 172 preferably have a peak current rating of at least 1.8 A.

If a rechargeable battery is used, a charger is required. Those skilled in the art will recognize that the charger may be integrated into the device 100 or enclosed in a separate enclosure, such as in the base 166. The base 166 includes a standard 110V electrical cable 1610 extending therefrom that is electrically connected to an AC/DC converter (not shown) in the base 166 that converts 110V AC supply to 6V DC. The base 166 also includes a pair of contacts (not shown) that engage recharger contacts (not shown) in the bottom end 165 of the handle portion 160 when the device 100 is inserted into the base 166.

Alternatively, the device 100 may be designed such that the battery 172 can be easily removed from the device 100 and charged in a separate charger (not shown). A further alternative is to replace the battery with an AC-to-DC converter, and power the device 100 through a line cord connected to an AC source.

Activation Switch

An activation switch 180 extends through the handle portion 160 to activate the device 100 upon a user engaging the activation switch 180. The activation switch 180 is preferably a button, as is shown in FIG. 2, or some other suitable device, such as a trigger, as will be recognized by those skilled in the art. Alternatively, the activation switch may be a foot switch (not shown) that is electronically connected to the system controller 190 to activate the device 100, such as by an electrical line.

The activation switch 180 is electronically connected to the system controller 190 via leads 182, 184. Preferably, the activation switch 180 is a three-position switch such that, when the activation switch 180 is depressed an initial amount from an open position to an initially closed position, the device 100 is activated. This activation illuminates the activation indicator 1310 to indicate that the device 100 is about to operate. When the activation switch 180 is completely depressed, the activation switch 180 transmits a signal, through the system controller 190, to operate the prime mover 140 for a period of time determined, through the system controller 190, by the settings on the dosage adjuster 1530. Preferably, the time period for operation extends between approximately 0.5 and 5 seconds. However, operation time of the prime mover 140 is not dependent on the duration of time that the activation switch 180 is depressed, but on the settings of the dosage adjuster 1530. However, it is preferred that, if the activation switch 180 is depressed for an extended period of time, such as greater than two seconds, the system controller 190 interprets the signal received from the activation switch 180 as a signal to run the device 100 continuously for a predetermined, extended period of time, such as thirty (30) seconds, such as to run a cleaning solution such as saline, through the device 100 to clean the device 100. Alternatively, if the activation switch 180 is depressed for longer than the predetermined period of time, the system controller 190 will provide power for the prime mover 140 to operate as long as the activation switch 180 is fully depressed.

Electronics

The primary function of the system controller 190 is to energize the prime mover 140, which is preferably a piezoelectric transducer assembly or other piezo device, as described above. When energized, the prime mover 140 generates a mist of fluid droplets from the fluid 122. The energizing signal for the prime mover 140 must excite the prime mover 140 at the proper resonant frequency, and must supply enough energy to the prime mover 140 to cause misting. A simple user interface, such as the activation switch 180, is required for operation and control of the prime mover 140. A microprocessor 192 will be used to provide intelligence for the interface between the activation switch 180 and the prime mover 140, and to supervise the circuits driving the prime mover 140, as well as all of the electronic features.

Figure 23:
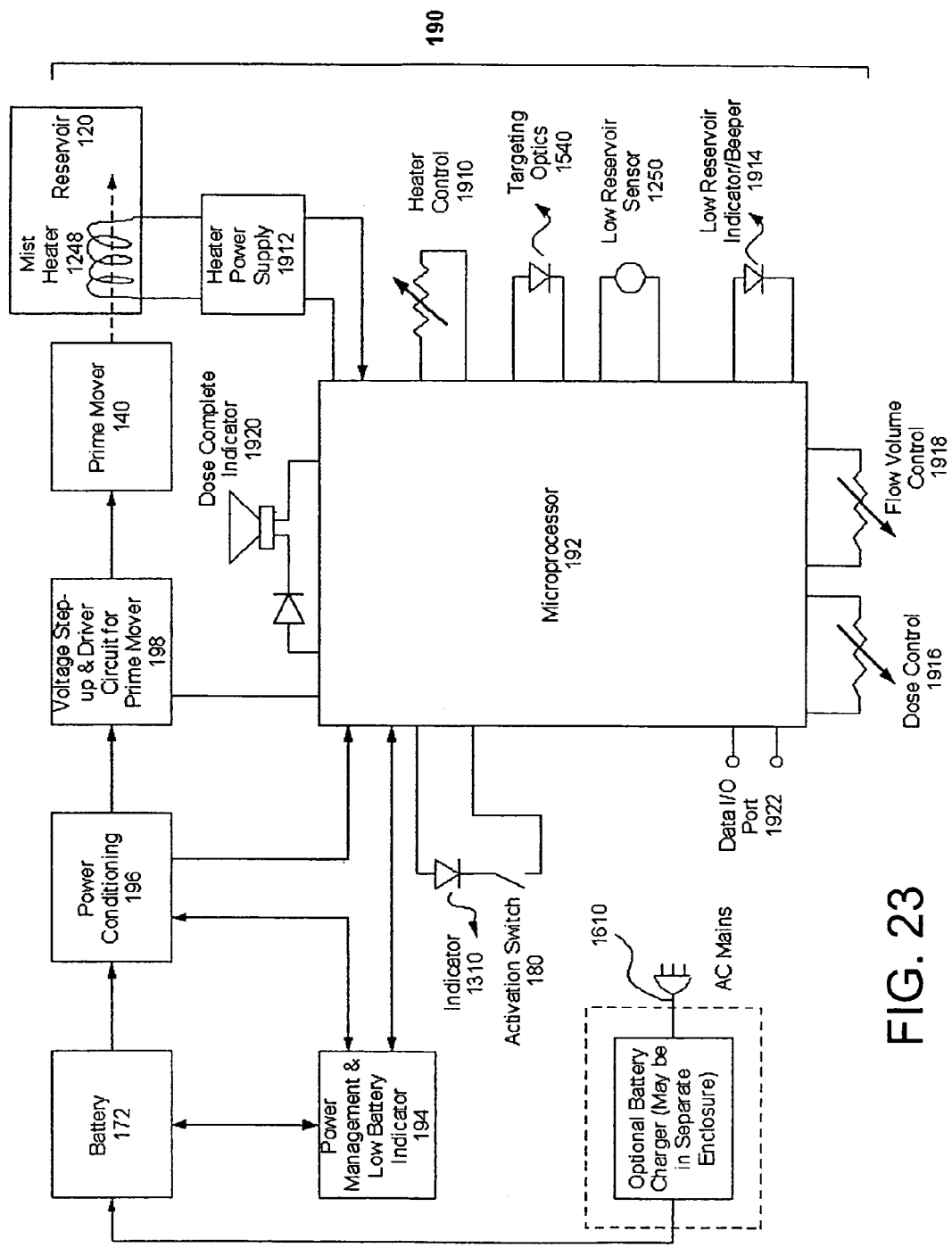
FIG. 23 is a schematic view of an electronic control system for the device.

The system controller 190 controls operation of the device 100 and includes a microprocessor 192, preferably in the form of a PCBA (Printed Circuit Board Assembly), to incorporate the electronics for operation of the device 100. FIG. 23 shows an electronic block diagram for a preferred embodiment of the system controller 190. The microprocessor 192 is housed in the system controller 190, through which a majority of the operation of the device 100 passes. The system controller 190 preferably also contains a non-volatile memory, input/output ("I/O") devices, digital-to-analog ("D/A") and analog-to-digital ("A/D") converters, driver circuits, firmware, and other electronic components, as will be described in detail herein. Alternatively, those skilled in the art will recognize that simple logic components may be used.

The activation switch 180 is part of a normally open ("NO") circuit that includes the activation indicator 1310. As described above, the activation switch 180 is a three-position switch, with the first position in the NO condition. The second position, when the activation switch 180 is depressed part way, powers the activation indicator 1310 to indicate to the user that the device 100 is on. The third position, when the activation switch 180 is fully depressed, activates the device 100 to operate the prime mover 140 to generate a mist from the nozzle assembly 150 for medication dispensing to the patient. To conserve power and lengthen operational battery life, all circuits are disconnected from power while the activation switch 180 is open.

A power management & low battery indicator 194 includes an electronic circuit that automatically measures the battery voltage and provides a visual or audible (beeping) indication if the voltage has dropped below a preset level. Power management chips (also known as "gas gages") are commercially available for various battery types, or such a circuit may be constructed from discrete components. Preferably, the circuit also provides "sleep" or "hibernate" modes, as are known to those skilled in the art, in which battery life is extended by reducing power consumption when the device 100 has been inactive for a preset amount of time.

An optional power conditioning circuit 196 provides a constant and regulated voltage to the rest of the system controller 190. Power conditioning chips are commercially available for various voltage and current requirements, or alternatively, such a circuit may be constructed from discrete components.

A voltage step-up & driver (VSD) circuit 198 powers the prime mover 140. For a prime mover 140 that includes the piezo device described above, the purpose of the VSD circuit 198 is to drive the piezoelectric crystal contained in the piezo device at a desired resonant frequency. Different crystals and piezoelectric assemblies have different resonant frequencies, as well as different Q-factors, so the VSD circuit 198 is preferably custom designed to match the operating characteristics of the particular piezo device. The VSD circuit 198 contains an oscillator formed of integrated and/or discrete components such as power transistors, power diodes, capacitors, and coils.

Preferably, the piezo device is driven by a square wave at its resonant frequency in the range of 50 KHz to 70 KHz. Since each piezo device has a slightly different resonant frequency, the circuit will use a Phase Lock Loop (PLL) or other feedback technique with a Voltage Controlled Oscillator (VCO) to lock on to the piezo resonant frequency and to automatically adjust the drive signal frequency as the resonant frequency varies. The piezo device is preferably driven by a peak-to-peak signal in the range of 200V, or as appropriate to provide sufficient misting. Using the preferred Omron piezoelectric device described above, the mist volume produced with this method is in the range of approximately 10 to 100 microliters/second.

The system controller 190 also optionally includes a heater control 1910 and that is electronically connected to the optional reservoir heater 1248 to heat the fluid 122 in the reservoir 120, as desired. The heater control 1910 includes a feedback loop to control the desired temperature of the fluid 122 in the reservoir 120. A heater power supply 1912 is also electronically connected to the system controller 190 to provide a power supply to the optional heater 1248.

Low Fluid Level

If the device 100 includes the low level sensor 1250 in the reservoir 120 as described above, the device 100 also includes a low fluid level alarm 1914 that is set to alarm when the fluid 122 in the reservoir 120 is depleted to a predetermined level. The low reservoir sensor 1250 is programmed to transmit a signal to the system controller 190 when the fluid level reaches the predetermined level. The system controller 190 in turn transmits a signal to the alarm 1914. The alarm 1914 may be a visual alarm, such as a blinking light, or the alarm 1914 may be an audible alarm, such as a beep.

Dosage Adjustment

A manual method and apparatus for adjusting dosage amount dispensed during operation of the device 100, using the dosage adjuster 1530, 1530a has been previously described. Adjustment of the dosage adjuster 1530, 1530a transmits a signal to a dose control circuit 1916 to determine the length of time that the prime mover 140 operates to dispense the fluid 122 from the reservoir 120 to the patient. The system controller 190 also includes a flow volume control circuit 1918 that determines the volume of the fluid 122 per unit time that is dispensed through the prime mover 140. The total amount of the fluid 122 dispensed is determined by the value of the flow rate as determined by the flow volume control circuit 1918 times the length of time of operation of the prime mover 140 as determined by the dose control circuit 1916. Preferably, the flow volume control circuit 1918 is preprogrammed into the system controller 190, while the dose control circuit 1916 may be manually adjusted based on the type of medication and the dosage that the prescribing physician determines is necessary based on the patient's condition.

Alternatively, instead of manually adjusting the dosage amount, the dosage amount may be adjusted electronically, such as by external calibration of the system controller 190 to adjust operational values of the dose control circuit 1916 and the flow volume control circuit 1918 based on need.

Dosage Complete Indicator

The system controller 190 also includes a "dosage complete" indicator 1920 that indicates when the device 100 has dispensed the prescribed amount of fluid 122 from the reservoir 120. The indicator 1920 may be may be a visual alarm, such as a blinking light, or the indicator 1920 may be an audible alarm, such as a beep. The indicator 1920 preferably is activated after a slight time delay, such as approximately 0.5 second, after the device 100 ceases to dispense the fluid 122 from the nozzle assembly 150. This delay ensures that the user does not remove the device 100 from in front of the patient's eye until all of the prescribed dose of medication has been dispensed from the device 100. Since the system controller 190 controls operation of the prime move 140, the system controller 190 is able to calculate the desired delay time between stopping operation of the prime mover 140 and sending the signal to the indicator 1920 to indicate that the dosage is complete.

Targeting Optics

If the optional electronic targeting mechanism 1540 is used, depressing the activation switch 180 to the first position transmits a signal to the system controller 190 to activate the targeting mechanism 1540, illuminating the light sources 1546, 1548 to project images on the patient's eye. The targeting mechanism 1540 remains activated when the activation switch 180 is depressed to the second position. When the activation switch 180 is released, signal to the system controller 190 ceases, and the targeting mechanism 1540 is deactivated by the system controller 190.

Outside Communications

Optionally, the device 100 may include an input/output (I/O) device 1922 for transmitting information between the device 100 and an outside device, such as a personal computer, PDA, or other such electronic device that is capable of displaying information transmitted from the device 100. Information that may be transmitted from the device 100 includes, but is not limited to, usage information, such as the number of times the device 100 was used, and at what times; dosage amount per application; and current and voltage draw of the device 100 during use, as well as other operational information about the device 100. Further, information may be transmitted from the outside device to the device 100. Such information may include, but is not limited to, clearance information to clear the system controller 190 memory of previous information that has already been downloaded to the outside device; operational information that allows the device 100 to be used with particular medicament reservoirs; temperature settings for the heater control 1910; and operational duration information to adjust the dose control circuit 1916 and the flow volume control circuit 1918 to adjust dosage amounts, as well as other information that may be transmitted to the system controller 190.

As shown in FIG. 2, the I/O device 1922 may include a port 1612 on the handle portion 160 for physically connecting the device 190 to the outside device, such as by a cable. The port 1612 may be a standard Universal Serial Bus (USB) port, or some other suitable port as will be recognized by those skilled in the art. The port 1612 is electronically connected to the system controller 190 by a port cable 1614 that transmits information between the port 1612 and the system controller 190. Alternatively, the I/O device 1922 may include an infrared transmitter/receiver (not shown) that allows the device 100 to be placed near, but not physically connected to, the outside device to exchange information such as the information described above.

Figure 24:
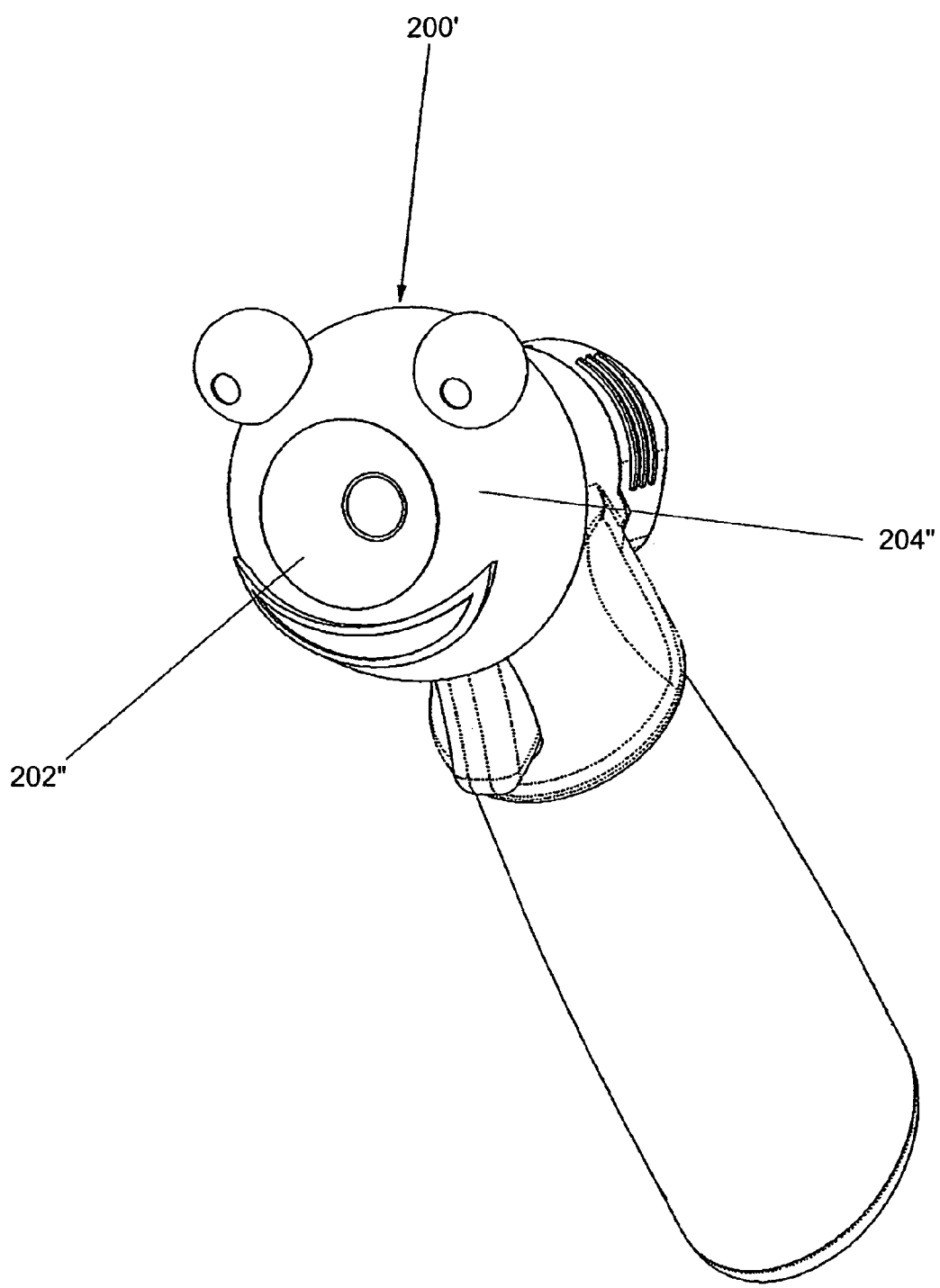
FIG. 24 is a perspective view of an alternative embodiment of the device according to the present invention.

A pediatric version of a device 200' according to an alternate embodiment of the present invention, shown in FIG. 24, may include a façade 204" at the distal end 202" of the device 200' that encourages younger patients to look in the direction of the device 200'. For example, for ophthalmic delivery, the façade 204" may include a clown face or an animal face that catches the attention of the patient and distracts the patient from the fluid that is being dispensed from the device 200'. In the embodiment shown in FIG. 24, the nose of the façade is the mesh plate 156. Alternatively, the façade 204" may include moving parts to distract the patient during operation of the device 200'.

Figure 25:
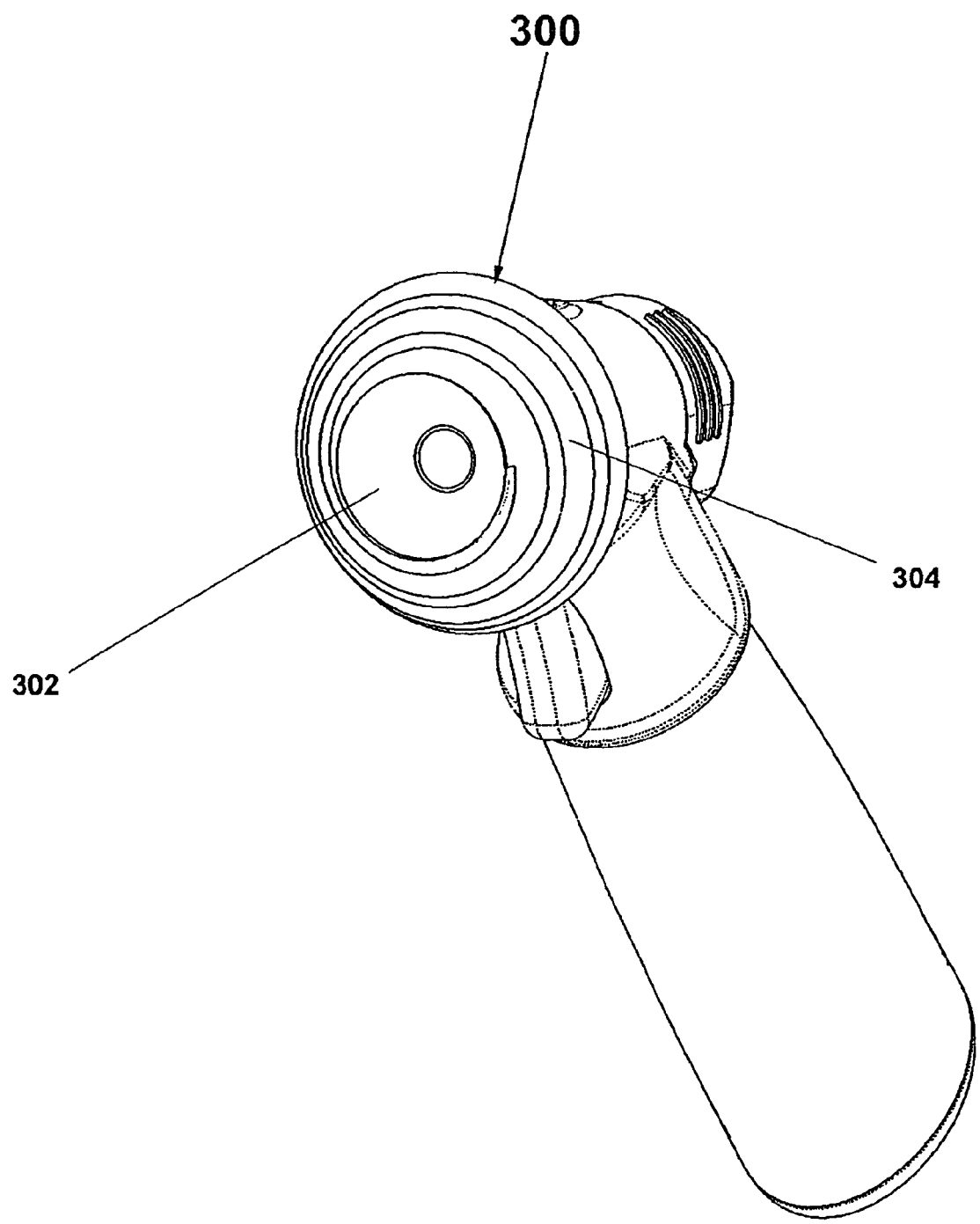
FIG. 25 is a perspective view of another alternative embodiment of the device according to the present invention.

Alternatively, a veterinary version of a device 300 according to yet another alternate embodiment of the present invention, shown in FIG. 25, may include a façade 304 at the distal end 302 of the device 300 that distracts the animal that is being medicated. The façade 304 may include a moving element for the animal to focus upon during administration of the fluid.

The embodiments shown and described above may be offered in a reusable configuration. In this event, the parts may be injection molding from clear polymer resins that withstand repeated sterilization by steam autoclave, such as autoclavable versions of acrylics, styrenes, and polycarbonates.

Alternatively, the embodiments shown may be offered as a sterile disposable. In this case it may be injection molded from a wide variety of clear polymer resins, including acrylics, styrenes, urethanes, PMMA, and polycarbonates. These resins are generally compatible with industrial sterilization by e-beam, gamma, and EtO.

Use

Between uses, the device 110 is typically stored in the base 166, with the bottom end 165 of the handle portion 160 inserted into the cavity 167 in the base 166. The electrical cable 1610 is connected to an external power supply to provide electrical power to the batteries 172 to charge/recharge the batteries 172. The heater 1248, if used, heats the fluid 122 in the reservoir. The temperature of the fluid 122 is controlled by the heater controller 1910 to maintain the fluid 122 at a desired temperature.

The device 100 is designed so that it can be used by one person to self administer medicament, such as a patient in his/her home, or, the device 100 can be used by one person to administer medicament to a second person, such as a medical professional treating a patient in a medical office or a hospital setting.

Figure 26:
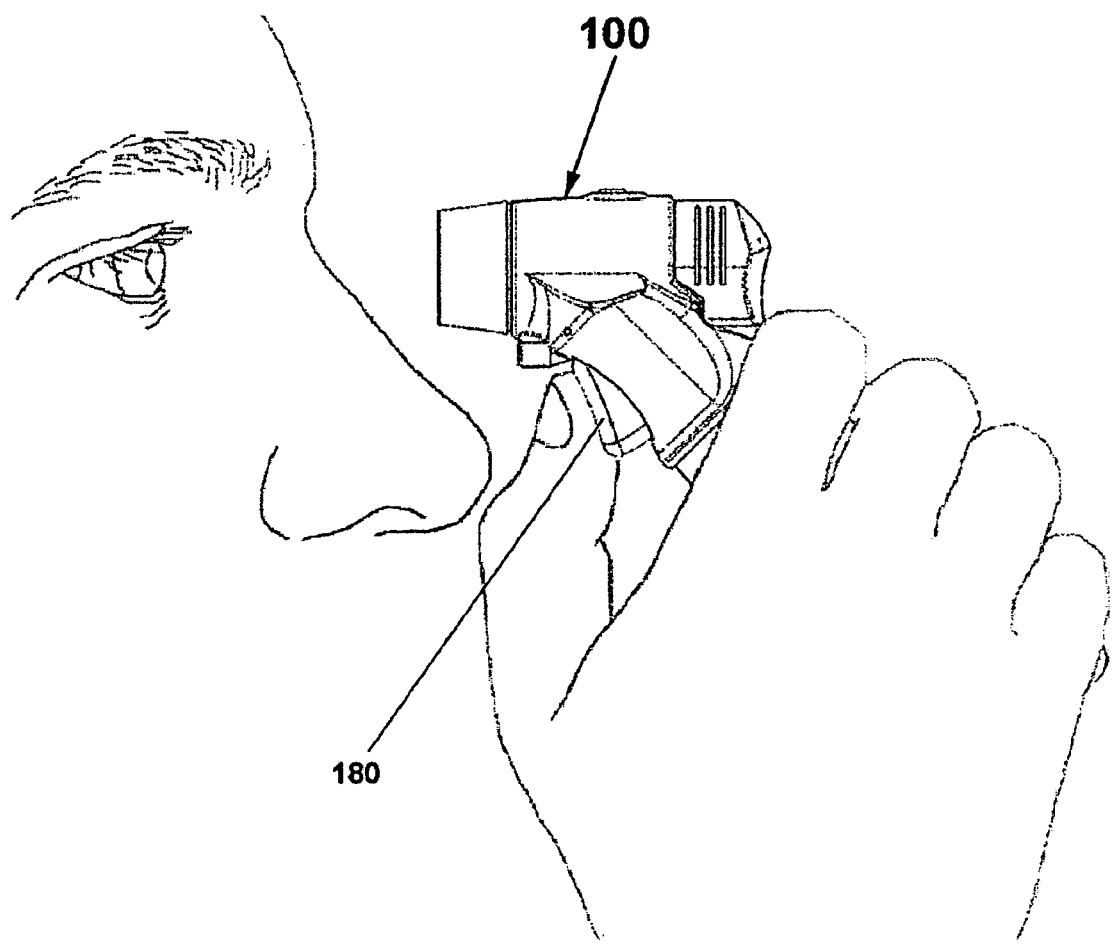
FIG. 26 is a perspective view showing self-administration of medication using the device.

For self use, the user removes the device 100 from the base 160 and aims the discharge end of the nozzle assembly 150 toward the eye into which the user intends to insert the eye medication. If the optional mechanical targeting means 1620 is connected to the device 100, the user inserts the connected end 1624 into the spacer recess 137. The user then uses the free end 1628 of the targeting means 1620 to depress the eyelid. When the device 100 is in the desired position, the user then uses his/her thumb, as shown in FIG. 26, to depress the activation switch 180. By pressing the activation switch 180 to the first position, the activation indicator 1310 is illuminated, indicating that the device 100 is ready for operation.

Figure 27:
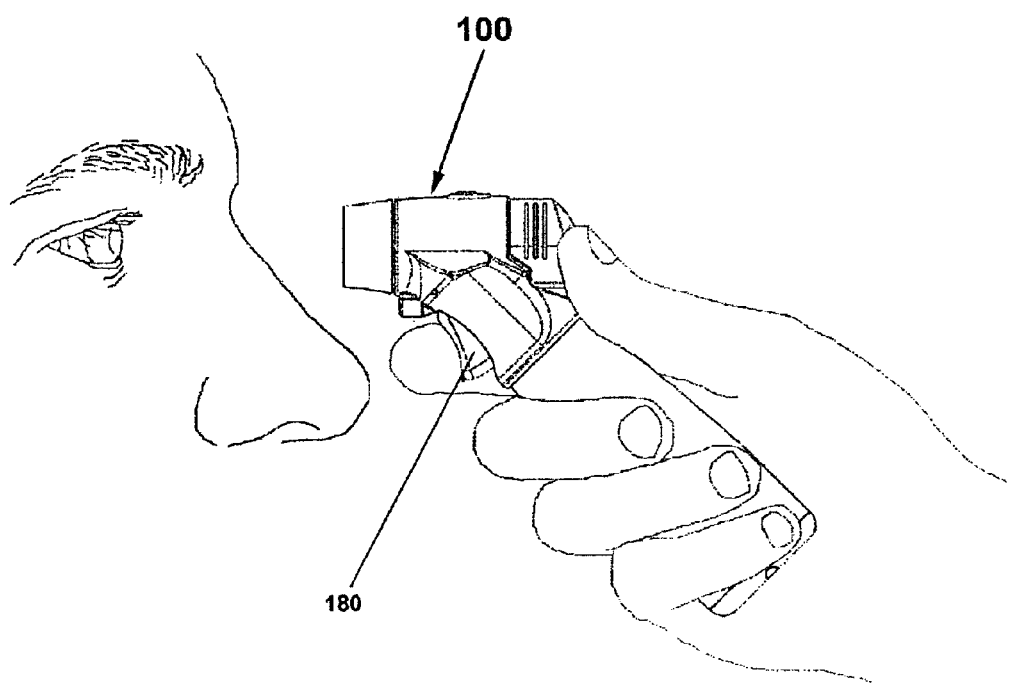
FIG. 27 is a perspective view showing administration of medication by one person to another using the device.

For professional use on a patient, the user, such as an optometrist or an ophthalmologist, removes the device 100 from the base 160 and aims the discharge end of the nozzle assembly 150 toward the eye into which the user intends to insert the eye medication. If the optional mechanical targeting means 1620 is connected to the device 100, the user inserts the connected end 1624 into the spacer recess 137. The user then uses the free end 1628 of the targeting means 1620 to depress the eyelid. When the device 100 is in the desired position, the user then uses his/her index finger, as shown in FIG. 27 to depress the activation switch 180. By pressing the activation switch 180 to the first position, the activation indicator 1310 is illuminated, indicating that the device 100 is ready for operation.

If the optical targeting mechanism 1540 is used, the user aims the device 100 generally toward the patient's eye and, using his/her forefinger, as shown in FIG. 27, depresses the activation switch 180 to the first position. The activation indicator 1310 is illuminated, indicating that the device 100 is ready for operation. Also, the light sources 1546, 1548 on the targeting mechanism 1540 are illuminated, projecting images onto the patient's eye. Preferably, the images are any of the images shown in FIGS. 17a-21c. The user can adjust the distance and aim of the device 100 relative to the patient's eye based on the images projected onto the patient's eye.

The remainder of the description of the operation of the device 100 is the same whether the device 100 is being used for self-administration of medication or whether the device 100 is being used by a professional to administer medication to a patient.

The user presses the activation switch 180 to the second position and then releases the activation switch 180, transmitting a signal to the system controller 190 to operate the prime mover 140. An electronic operational signal is transmitted through the power management circuit 194 and the VSD circuit 198 to the prime mover 140 which, in the case of the piezoelectric device described above, causes the piezoelectric device to vibrate, preferably at an ultrasonic frequency, along its longitudinal axis 148. The prime mover 140 is operated for a predetermined amount of time, preferably between approximately 0.5 and 2 seconds, as programmed into the system controller 190 prior to use. The prime mover 140 operates for the predetermined amount of time, regardless of how long the activation switch 180 is depressed, unless the activation switch 180 is depressed in excess of a predetermined period of time, such as 5 seconds, as will be described in more detail later herein.

The vibration of the prime mover 140 draws fluid 122 from the reservoir 120 and through the lumen 1410. The fluid 122 exits the distal end 144 of the prime mover 140 and passes through the openings 1520 in the mesh plate 156, where the fluid 122 is broken into micron-sized particles, which are directed toward the patient's eye. After the prime mover 140 has operated for the predetermined period of time, the system controller 190 ceases to transmit the operational signal and the prime mover 140 stops. At this time, the system controller 190 transmits a signal to the dose complete indicator 1920 to indicate to the user that the dosage is complete.

If the user is using the mechanical targeting means 1620, the user preferably removes the connected end 1624 from the spacer recess 137 and discards the elongated member 1622 to ensure that any bacteria from the patient's eye is not transmitted to the targeting means 1620 and then retransmitted to the next patient.

If the level of the fluid 122 in the reservoir 120 drops below a predetermined level, the low reservoir sensor 1250 transmits a signal to the system controller 190, which in turn transmits a signal to the low reservoir indicator 1914, informing the user that the reservoir 120 must be removed and a new reservoir must be inserted into the body 130.

If the low battery indicator 194 indicates that the power source 170 is at lower power, the user may insert the device 100 into the base 166 to charge the power source 170, or alternatively, replace the power source 170.

In the event that the user desires to change medication in the reservoir 120, it is recommended that the device 100 be "flushed" after removing the original medication but before using the new medication, so as not to contaminate the new medication with the old medication. In such an instance, the user inserts a reservoir containing a cleaning fluid, such as a saline solution into the body 130, and depresses the activation switch 180 in excess of a predetermined period of time, such as 5 seconds. The system controller 190 recognizes the extended depression of the activation switch 180 as the start of a cleaning cycle and operates the prime mover 140 for an extended period of time, such as for 30 seconds, or some other predetermined time, as desired. At the end of the cleaning cycle, the dose complete indicator 1920 may activate, alerting the user that the device 100 is clean, and that a new medication may now be used in the device 100.

Referring generally to FIGS. 28-54, an alternative exemplary embodiment of a misting device 200 according to the present invention is shown. Misting device 200 is similar to other embodiments of a misting device in that it facilitates a controlled and metered flow of a predetermined dosage of an atomized mist of an ophthalmic fluid to an ocular region of a patient. The ocular region, or ocular adnexa, includes the eye, eyelids, eyelashes, eyebrows, and lacrimal apparatus.

Referring generally to FIGS. 28-54, the ophthalmic fluid delivery device 200 is adapted to deliver an ophthalmic fluid in the form of a mist to the ocular region of a patient and has a nozzle 2402 operable between open and closed positions. More specifically, the ophthalmic fluid delivery device 200 includes a nozzle 2402 defining an aperture 2411 through which the ophthalmic fluid can flow. At least one shutter 2428 is positioned proximate to the aperture 2411 of the nozzle 2402, and the shutter 2428 is mounted for movement with respect to the aperture 2411 of the nozzle 2402 between an open position permitting flow of the ophthalmic fluid through the aperture 2411 of the nozzle 2402 and a closed position at least partially covering the aperture 2411 of the nozzle 2402. A shutter actuator 2440 is positioned proximate the shutter 2428, and the shutter actuator 2440 is mounted for movement with respect to the nozzle 2402. The shuttle actuator 2440 is coupled to the shutter 2428 such that the movement of the shutter actuator 2440 moves the shutter 2428 between the open position and the closed position.

According to this exemplary embodiment, the shutter 2428 is mounted for movement with respect to the aperture 2411 of the nozzle 2402 between the open position and a closed position that substantially completely covers the aperture 2411 of the nozzle 2402. Also, plural shutters 2428 are positioned proximate to the aperture 2411 of the nozzle 2402 according to this exemplary embodiment, at least one of the shutters 2428 being mounted for movement with respect to the aperture 2411 of the nozzle 2402 between the open position and the closed position. Where plural shutters 2428 are used, each of the shutters 2428 is mounted for movement with respect to the aperture 2411 of the nozzle 2402 according to this embodiment, and the shutters 2428 in the closed position cooperate to at least partially impede the flow of the ophthalmic fluid through the aperture 2411 of the nozzle 2402. The aperture 2411 of the nozzle 2402 is oriented along a nozzle, or discharge, axis 2412, and the shutter actuator 2440 is mounted for rotational movement about the nozzle axis 2412 such that rotation of the shutter actuator 2440 moves the shutter 2428 between the open position and the closed position.

The ophthalmic fluid delivery device 200 also has a body configuration with a nozzle axis 2412 oriented at an angle with respect to an axis 2508 of the handle 2502 of the device 200. More specifically, the nozzle assembly 240 is configured to deliver the ophthalmic fluid to the ocular region of the patient generally along a nozzle axis 2412. A handle assembly 250 of the device 200 is coupled to the nozzle assembly 240 and is configured to be gripped by a hand of the patient or another user of the ophthalmic fluid delivery device 200. The handle assembly 250 is oriented generally along a handle axis 2508. The nozzle axis 2412 and the handle axis 2508 together define an angle greater than 90 degrees such that the ophthalmic fluid is delivered to the ocular region of the patient along a nozzle axis 2412 that is obtuse with respect to the handle axis 2508. More preferably, the nozzle axis 2412 and the handle axis 2508 together define an angle from about 105 degrees to about 125 degrees. Even more preferably, the nozzle axis 2412 and the handle axis 2508 together define an angle from about 110 degrees to about 120 degrees.

The ophthalmic fluid delivery device 200 also has an aperture 2719 on its body to enable a label 2260 on a reservoir 220 mounted therein to be read. More specifically, the ophthalmic fluid delivery device 200 is adapted to deliver an ophthalmic fluid or other such fluid, such as a cleaning fluid, from a reservoir 220 containing the fluid. It should be noted that the cleaning fluid is compatible with a device used to dispense fluid toward the ocular region. The ophthalmic fluid delivery device 200 has a housing 270 defining a cavity 2606 sized to accommodate the reservoir 220. The nozzle assembly 240 of the device 200 is coupled to the housing 270 proximate to the cavity 2606, and the nozzle assembly 240 is configured to deliver the ophthalmic fluid from the reservoir 220 and to the ocular region of the patient. An aperture 2719 is defined by the housing 270 adjacent the cavity 2606 defined by the housing 270, and the aperture 2719 is positioned to permit visualization of the reservoir 220 from outside the housing 270 when the reservoir 220 is positioned within the cavity 2606 of the housing 270.

Preferably, the housing 270 is provided with a door 2702 that is movable to an open position to facilitate access to the cavity 2606. The door 2702 can be slidably movable with respect to the cavity 2606, and the door 2702 is optionally removable from the body 260. The aperture 2719 is optionally defined by the door 2702, and the aperture 2719 optionally includes a substantially translucent window 2720.

The ophthalmic fluid delivery device 200 also includes a reservoir alignment feature. The reservoir 220 defines a reservoir surface contour 2244, 2246 that may be unique to the particular ophthalmic fluid that it contains. The body 260 of the ophthalmic fluid delivery device 200 has a keyed surface contour 2608 positioned adjacent the cavity 2606. The keyed surface contour 2608 is oriented to permit insertion of the reservoir 220 into the cavity 2606 in a predetermined alignment and to prevent insertion of the reservoir 220 into the cavity 2606 in an alignment other than the predetermined alignment.

The keyed surface contour 2608 is optionally concave and extends toward a central region of the cavity 2606. For an ophthalmic fluid delivery device 200 adapted to deliver the ophthalmic fluid along a delivery axis 2412, the keyed surface contour 2608 is optionally oriented to permit insertion of the reservoir 220 into the cavity 2606 in a predetermined alignment substantially parallel to the delivery axis 2412. The cavity 2606 defined by said housing can be substantially cylindrical, and the keyed surface contour 2608 can extend along a length of the cavity 2606.

The ophthalmic fluid delivery device 200 also has a venturi vent 2422 in the nozzle 2402 in order to improve the delivery of ophthalmic fluid in the form of a mist in a controlled plume. More specifically, the nozzle 2402 of the device 200 defines an aperture 2411 positioned along the nozzle axis 2412 through which the ophthalmic fluid can flow. The nozzle 2402 further defines at least one venturi opening 2422 separate from the aperture 2411 and oriented to introduce air into the nozzle 2402 at an angle to the nozzle axis 2412. The ophthalmic fluid delivery device 200 optionally includes a mesh 2320 positioned along the nozzle axis 2412, and the venturi opening 2422 is optionally positioned proximate to the mesh 2320. The nozzle 2402 can define plural venturi openings 2422 separate from the aperture 2411 and oriented to introduce air into the nozzle 2402 at an angle of between about 30 degrees and about 90 degrees relative to the nozzle axis 2412.

The ophthalmic fluid delivery device 200 also has a transducer 2104 configured to advance the ophthalmic fluid toward the ocular region of the patient. Transducer 2104 defines a lumen 2112 for the flow of the ophthalmic fluid having an aspect ratio of between about 22 and about 26.

The reservoir assembly 220 used with the device 200 has a number of beneficial features that facilitate the insertion and removal of a supply or dosage or regimen of ophthalmic fluid into the delivery device 200. It is contemplated that some or all of these features are optionally incorporated into the design of reservoir assembly 220.

According to one exemplary embodiment, the reservoir assembly 220 includes a seal, such as a gasket 2252 that is closed when not in contact with other components of the delivery device 200 and open when in contact with such device components. More specifically, a reservoir assembly 220 is provided for use in an ophthalmic fluid delivery device

200 having a lumen-defining component (hereinafter referred to as "lumen") 2112 configured to deliver an ophthalmic fluid from the reservoir assembly 220. The reservoir assembly 220 includes a reservoir defining an aperture 2250 and a cavity 2234 in fluid flow communication with the aperture 2250. The reservoir assembly 220 also includes an ophthalmic fluid contained in the cavity 2234 of the reservoir 220. Gasket 2252 is provided to traverse the aperture 2250 of the reservoir 220, and the gasket 2252 defines a passage configured to receive a portion of the lumen 2112 and to permit the flow of the ophthalmic fluid from the cavity 2234 and through the aperture 2250 of the reservoir 220 when the portion of the lumen 2112 is inserted through the passage. The gasket 2252 is also configured to substantially prevent the flow of the ophthalmic fluid from the cavity 2234 and through the aperture 2250 of the reservoir 220 and the passage of the gasket 2252 when the portion of the lumen 2112 is not inserted through the passage.

As will be described later in greater detail, the lumen 2112 can be defined by a transducer 2104. Also, the gasket 2252 can be positioned within the aperture 2250 of the reservoir 220, and the passage defined by the gasket 2252 is optionally expandable to accommodate the lumen 2112.

The reservoir 220 is also provided with an alignment feature on its body. More specifically, when configured to be positioned within a body 260 of an ophthalmic fluid delivery device 200 having a keyed surface contour 2608 positioned adjacent a cavity 2606 in the body 260, the reservoir assembly 220 is optionally provided with a reservoir having a wall 2226 at least partially defining a cavity 2234, an ophthalmic fluid contained in the cavity 2234 of the reservoir 220, and a reservoir wall 2226 having a reservoir surface contour 2244, 2246 oriented to permit insertion of the reservoir assembly 220 into the cavity 2606 of the body 260 of the ophthalmic fluid delivery device 200 in a predetermined alignment and to prevent insertion of the reservoir assembly 220 into the cavity 2606 of the body 260 in an alignment other than the predetermined alignment.

The reservoir 220 optionally defines an aperture 2250 in fluid flow communication with the cavity 2234, where the cavity 2234 is oriented along a cavity axis 2258 and the aperture 2250 is oriented along an aperture axis 2256 substantially parallel to the cavity axis 2258 and the aperture axis 2256 is offset from the cavity axis 2258. In this way, the aperture 2250 is optionally positioned proximate the wall 2226 of the reservoir 220 and facilitates flow of the ophthalmic fluid from the cavity 2234 when the aperture axis 2256 is substantially horizontal.

The reservoir surface contour can be oriented to permit insertion of the reservoir assembly 220 into the cavity 2606 of the body 260 of the ophthalmic fluid delivery device 200 in a predetermined alignment substantially parallel to the cavity axis 2258. Also, the wall 2226 of the reservoir 220 is optionally substantially cylindrical, with the reservoir surface contour extending along a length of the wall 2226 substantially parallel to the aperture axis 2256.

The reservoir assembly 220 optionally provides a ratio of total volume to application volume. More specifically, reservoir assembly 220 optionally contains about 1 ml of an ophthalmic fluid. In an exemplary embodiment, with each operation of device 200 being an "application", each application consumes about 5 microliters of the ophthalmic fluid. The volume of the ophthalmic fluid corresponds to at least between about 150 applications and about 250 applications. In other words, the ratio of the total contained volume to the volume of each application is at least about 150:1 to about 250:1, more preferably at least about 175:1 to about 225:1, and most preferably at least about 200:1.

According to the illustrated embodiment, the reservoir 220 also includes an integral vent feature 2240. More specifically, the reservoir assembly 220 includes a reservoir defining a cavity 2234, an aperture 2250 in fluid flow communication with the cavity 2234 and oriented along an aperture axis 2256, and a vent opening 2240 in fluid flow communication with the cavity 2234 and oriented at an angle with respect to the aperture axis 2256. A gasket 2252 traverses the aperture 2250 of the reservoir 220, substantially preventing the flow of ophthalmic fluid from the cavity 2234 and through the aperture 2250 of the reservoir 220. A filter 2242 traverses the vent opening 2240 of the reservoir 220, and the filter 2242 is configured to allow air to enter cavity 2234 through the vent opening 2240 and to substantially prevent the ophthalmic fluid from escaping from the cavity 2234 through the vent opening 2240.

The filter 2242 optionally comprises expanded PTFE and is optionally hydrophobic. The filter 2242 is also optionally configured to substantially prevent microbes from entering the cavity 2234 through the vent opening 2240. According to the illustrated embodiment, the aperture 2250 is positioned at a distal end of the reservoir 220, the vent opening 2240 is positioned toward the proximal end of the reservoir 220, and the vent opening 2240 is positioned to substantially prevent contact between the ophthalmic fluid and the filter 2242 as the ophthalmic fluid is withdrawn from the cavity 2234. The vent opening 2240 is optionally positioned at an elevation above a level of the ophthalmic fluid as the ophthalmic fluid is withdrawn from the cavity 2234.

According to the illustrated embodiment, the reservoir assembly 220 also includes an inner body portion 2210 having an open distal end and a vented proximal end and an outer body portion 2202 having an open proximal end and an apertured distal end. The open distal end of the inner body portion 2210 is disposed within the open proximal end of the outer body portion 2202, forming cavity 2234 to contain the ophthalmic fluid.

The vent 2242 of the vented proximal end of the inner body portion 2210 fluidly communicates with aperture 2250 through the cavity 2234. At least one of the inner body portion 2210 and the outer body portion 2202 comprises a surface contour 2246, 2244, respectively, oriented to permit insertion of reservoir assembly 220 into cavity 2606 of the ophthalmic fluid delivery device 200 in a predetermined alignment and to prevent insertion of reservoir assembly 200 into the cavity 2606 in an alignment other than the predetermined alignment. Surface contours 2244, 2246 are disposed away from the vent 2242. A cap 2262 is releasably coupled to the apertured distal end.

Referring now to FIGS. 28-52, exemplary features of the illustrated embodiment of the device 200 will now be described. The device 200 includes a body or housing that contains or supports subassemblies of components that together provide a controlled and metered mist of ophthalmic fluid.

Figure 28:
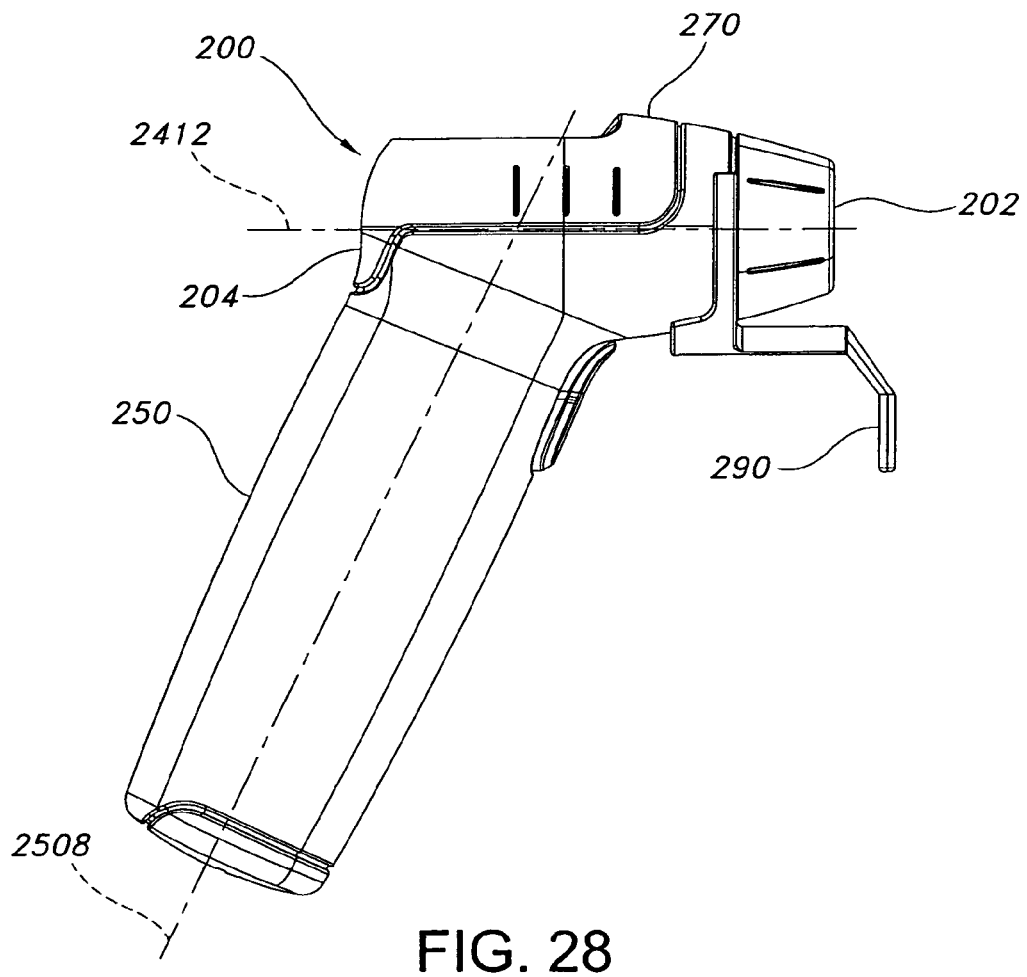
Figure 29:
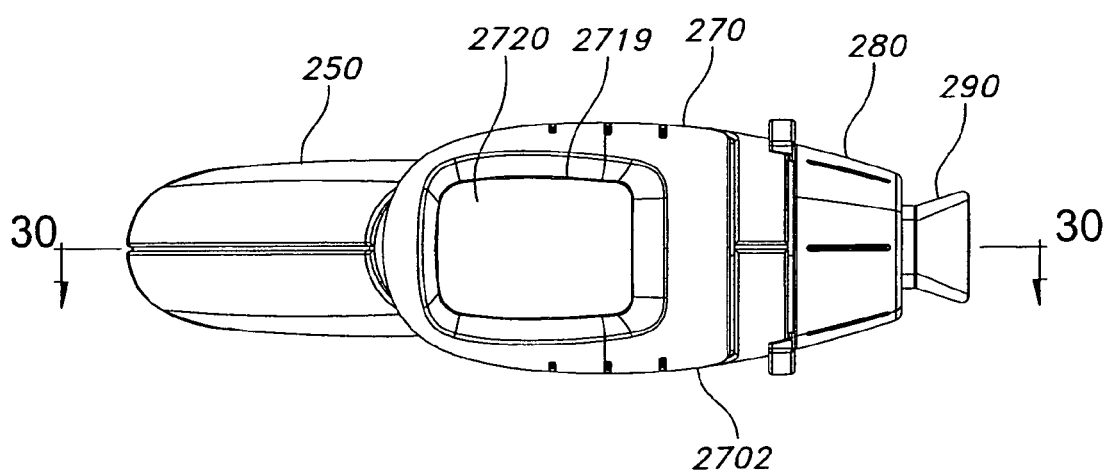
Figure 30:
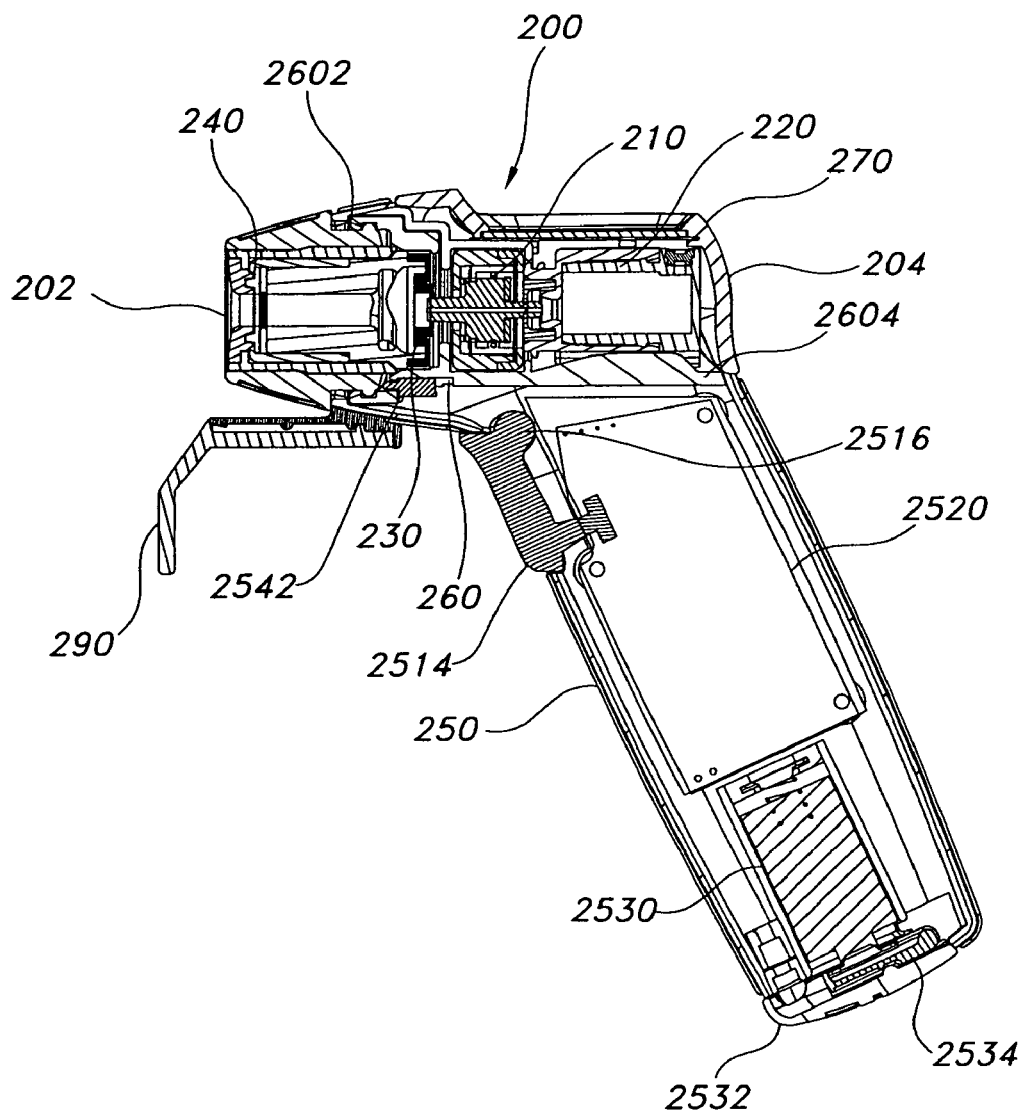

Referring specifically to FIGS. 28 and 30, device 200 is generally "gun-shaped" with a handle assembly 250 that is gripped by the user (which may be a patient, a medical professional or other user) and a body 260 mounted on handle assembly 250. Device 200 has a distal end 202 that is pointed toward patient when device 200 is in use and a proximal end 204 that is pointed toward a user, such as when a physician or other person is using device 200 to administer the ophthalmic fluid to the patient.

The overall shape, contours, and three-dimensional configuration of device 200 are selected to provide device 200 with a pleasing ornamental appearance. Alternative ornamental designs can be selected while maintaining the performance of device 200.

Figure 31:
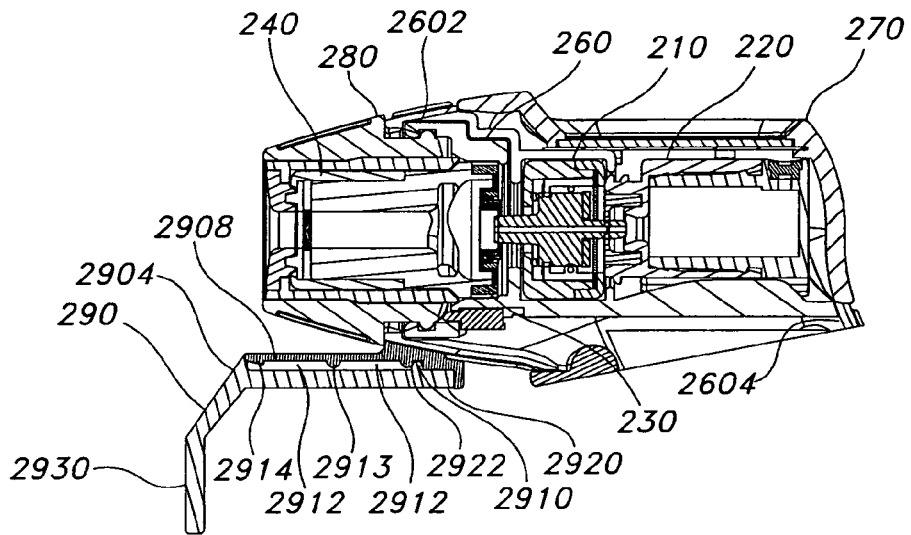
Figure 32:
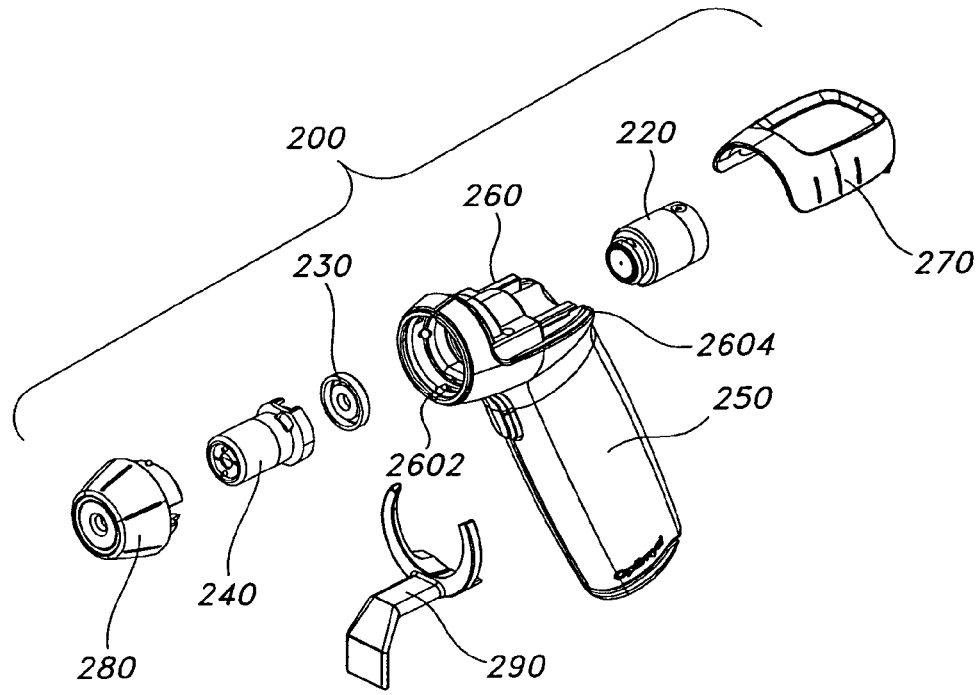

Referring specifically to FIGS. 31 and 32, misting device 200 includes an ultrasonic transducer assembly 210 that generates a mist of either an FDA-approved or a non-FDA approved ophthalmic fluid for treatment of an eye. A reservoir assembly 220 that includes the ophthalmic fluid is releasably insertable into misting device 200 for dispensing the fluid from misting device 200 through a mesh assembly 230. A nozzle assembly 240 dispenses the ophthalmic fluid from transducer assembly 210. Referring specifically to FIG. 32, a top housing assembly 270 covers reservoir assembly 220 within device 200. A rotatable nosecone assembly 280 arms/disarms device 200, opens an aperture of the ophthalmic fluid delivery device 200 to permit flow of ophthalmic fluid therethrough, opens a venturi passage defined by the ophthalmic fluid delivery device 200 to permit flow of air through the aperture with the ophthalmic fluid, and activates an indicator to indicate that the ophthalmic fluid delivery device 200 is ready to deliver the ophthalmic fluid. A spacer assembly 290 spaces distal end 204 of device 200 a predetermined distance or a selection of optional distances from a patient during operation of device 200. Electronics and power (not shown in FIG. 32) to operate device 200 are housed within handle assembly 250.

Figure 33:
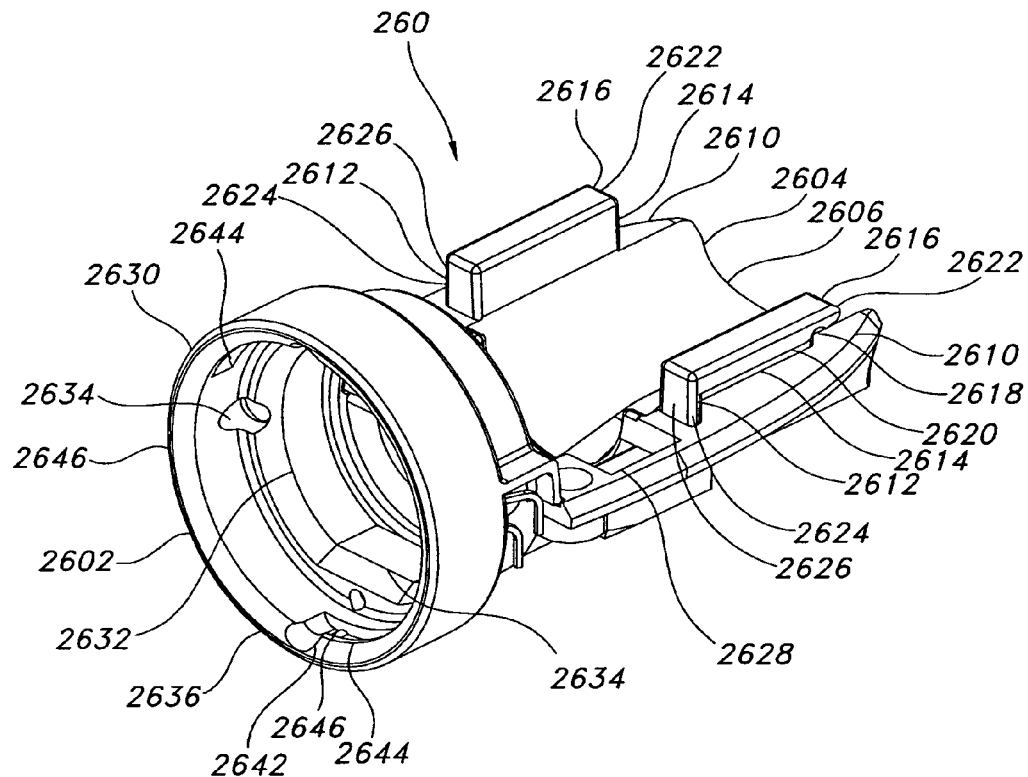
Figure 34:
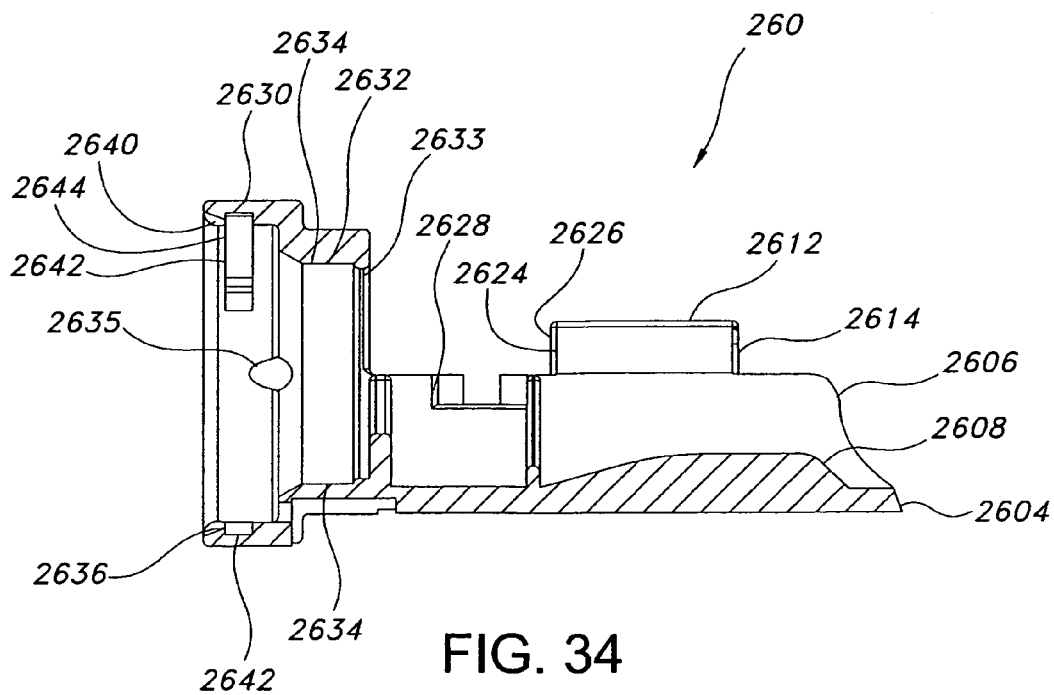
Figure 35:
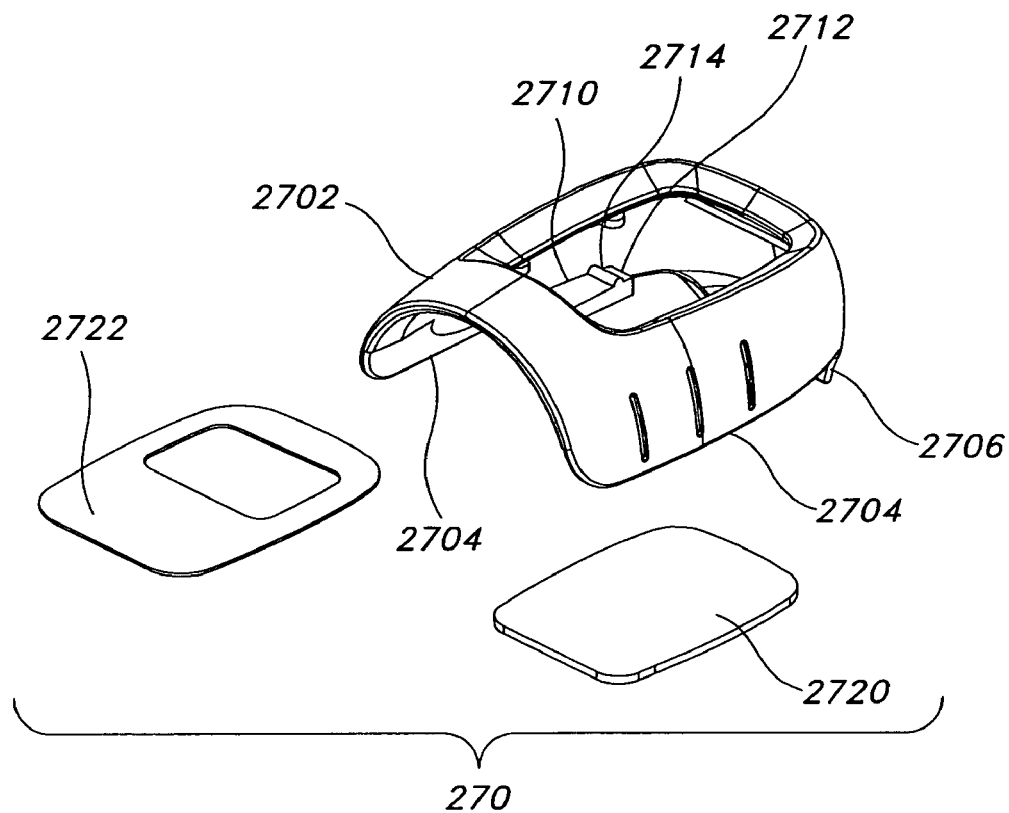
Figure 36:
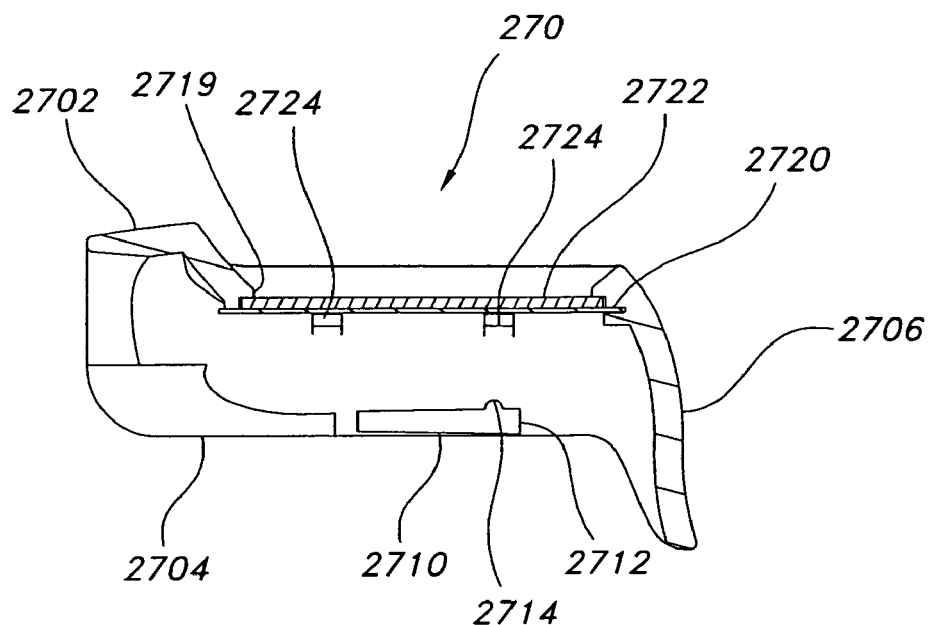
Figure 37:
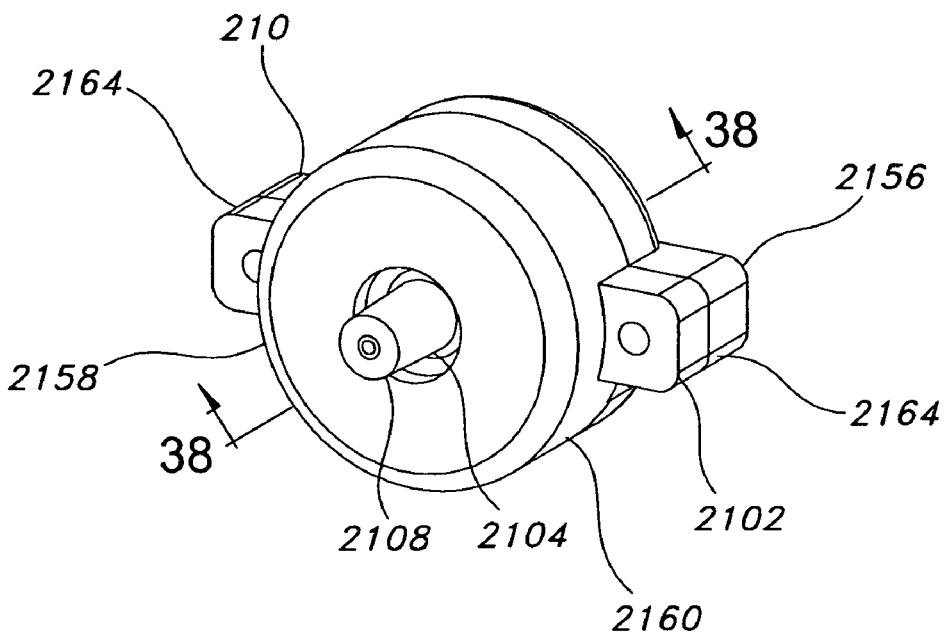
Figure 38:
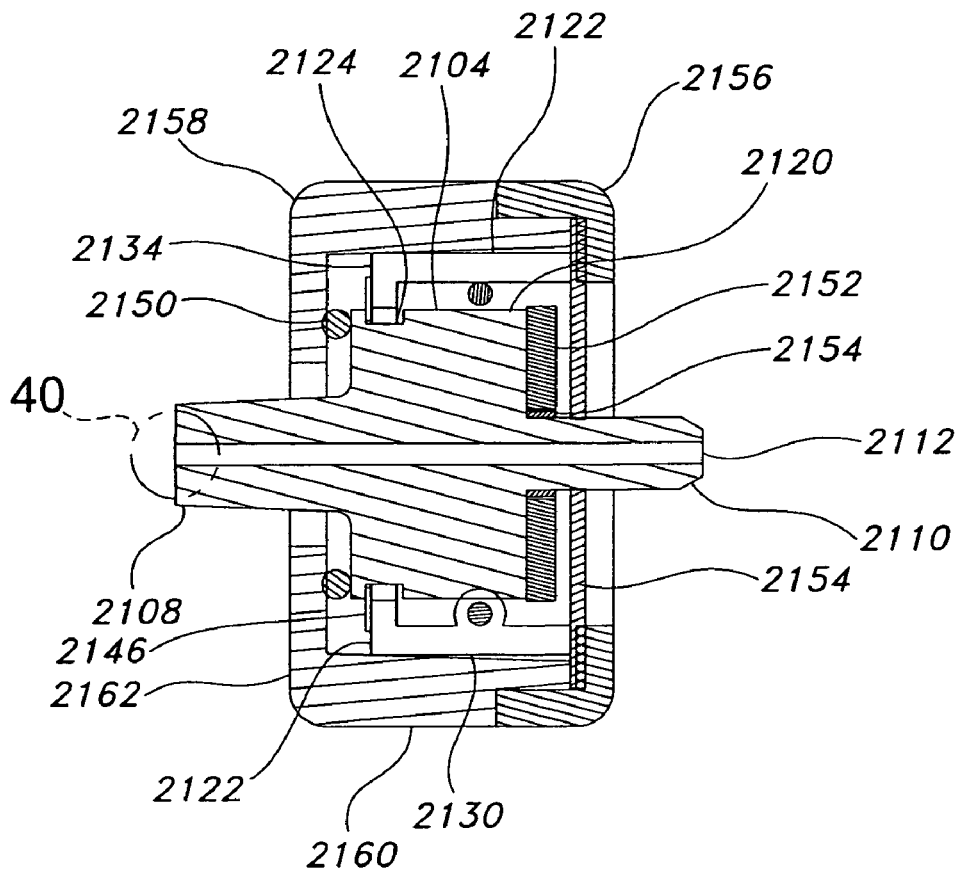

Referring to FIGS. 33 and 34, body 260 is fixedly retained onto handle assembly 250. Proximal end 2604 of body 260 is adapted to releasably receive fluid reservoir or reservoir assembly 220. Top housing assembly 270, shown in detail in FIGS. 35 and 36, is removably attached to body 260 to cover fluid reservoir 220 after fluid reservoir 220 is inserted into body 206. Referring to FIGS. 31 and 32, nozzle assembly 240 is releasably coupled near distal end 2602 of body 260. Transducer assembly 210 is coupled to body 260 between proximal end 2604 and distal end 2602 of body 260. Body 260 supports, from proximal end 2604 to distal end 2602: cover assembly 270, reservoir 220, transducer assembly 210, mesh cap assembly 230, nozzle assembly 240 and nosecone assembly 280.

Referring back to FIGS. 33 and 34, proximal end 2604 of body 260 includes a generally concave cradle 2606 into which reservoir 220 is inserted. Cradle 2606 defines a cavity and includes a keyed surface contour 2608 that mates with a corresponding contour in reservoir assembly 220 to reduce the likelihood that reservoir assembly 220 is incorrectly inserted into cradle 2606, and also may reduce the likelihood that a reservoir assembly 220 having improper ophthalmic fluid disposed therein is inserted into device 220. In other words, reservoir assembly 220 is optionally provided with a contour that is specific to a selected ophthalmic fluid. In order to customize the device 200 for use with a particular ophthalmic fluid, the device is optionally provided with a keyed surface contour 2608 that matches or otherwise accommodates the contour on the reservoir. Thus, the keyed surface contour 2608 can help ensure that the reservoir is properly oriented within the body of the device, that the correct reservoir assembly 220 (and therefore the correct fluid) is installed in the corresponding device, or both.

Body 260 includes a pair of flanges 2610 that extend laterally from cradle 2606. Each flange 2610 supports a base rail 2612 that extends away from its respective flange 2610. Each base rail 2612 includes a riser 2614 extending perpendicularly from flange 2610 and a tang 2616 that extends from riser 2614 parallel to flange 2610. Each tang 2616 includes a generally curved notch 2618 on a bottom face 2620 of tang 2616 toward proximal end 2622 of tang 2616 (only one notch 2618 and bottom face 2620 shown in FIG. 33). A stop 2624 is disposed at a distal end 2626 of each base rail 2612.

Base rails 2612 are used to releasably retain top housing assembly 270 that is slid over proximal end 2602 of body 260 and reservoir 220, after reservoir 220 is inserted into cradle 2606. Flanges 2610 each include a notch 2628 disposed distally of base rails 2612 for receiving transducer assembly 210.

Body 260 further includes a generally annular insert portion 2630 that is disposed at a distal end 2602 of body 260. Insert portion 2630 receives and/or retains mesh assembly 230, nozzle assembly 240, and nosecone assembly 280 on body 270. Insert portion 2630 includes a generally annular mesh/nozzle ring 2632 that is sized to accept and releasably retain mesh assembly 230 and nozzle assembly 240. A generally annular stop 2633 stops proximal movement of mesh assembly 230 during insertion into mesh/nozzle ring 2632. Mesh/nozzle ring 2632 includes diametrically opposed nozzle ring flats 2634 that receive corresponding flats on nozzle assembly 240. Nozzle ring flats 2634 prevent nozzle assembly 240 from rotating within respect to insert portion 2630 after assembly. Mesh/nozzle ring 2632 also includes a pair of diametrically spaced openings 2635 (only one opening 2635 shown in FIG. 33) therethrough that each house a light emitting diode (LED) 2637, shown in FIG. 48. LED's 2637 are used to light nosecone assembly 280, as will be described in detail later herein.

Referring back to FIGS. 33 and 34, distal end 2636 of insert portion 2630 includes a nosecone ring 2640 that is located distally of mesh/nozzle ring 2632. Nosecone ring 2640 receives nosecone assembly 280 and allows nosecone assembly 280 to rotate relative to insert portion 2630. Nosecone ring 2640 includes a pair of diametrically opposed grooves 2642 that extend longitudinally in a proximal direction from distal end 2636 of insert portion 2630. Each groove 2642 extends radially from a proximal end for approximately 60 degrees around nosecone ring 2640. Grooves 2642 accept and retain corresponding nubs on nosecone assembly 280 and act as guides for nosecone assembly 280.

A radial 2644 portion of each groove 2642 includes a slight ridge 2646 (only one ridge 2646 shown in FIG. 33) protruding from nosecone ring 2640 into groove 2642. Ridges 2646 retain nubs within radial portion 2644 of grooves 2642 so that nosecone assembly 280 is releasable from insert portion 2630 only with sufficient force to force nubs over ridges 2646.

Body 250 may be constructed from Acrylonitrile Butadiene Styrene (ABS) or other suitable material. It is optionally molded such as by injection molding techniques or is otherwise formed using known manufacturing processes.

Referring now to FIGS. 35 and 36, top housing assembly 270 includes a generally curved body 2702 with longitudinal sides 2704. A proximal portion 2706 connects longitudinal sides 2704 at a proximal end of top housing assembly 270. Proximal portion 2704 covers distal end of reservoir 220 when reservoir 220 is inserted into device 200. Body 2702 may be constructed from ABS or any other suitable material or materials.

A locking rail 2710 extends inwardly from each of longitudinal sides 2704. Each locking rail 2710 is configured to mate with a respective base rail 2612. A proximal end of 2712 of each locking rail 2710 includes a nub 2714 configured to fit into notch 2618 in the respective base rail 2612 to releasably engage top housing assembly 270 onto body 260. Locking rails 2710 are aligned under each respective base rail 2612 and top housing assembly 270 may be slid distally until locking rails 2710 engage stops 2624. Each nub 2714 seats in its respective notch 2618, with an audible and palpable snap-click, releasably retaining top housing assembly 270 onto body 260.

Top housing assembly 270 also includes a generally rectangular or otherwise shaped aperture 2719 for a window 2720 that allows a user to view a label on reservoir assembly 220 when reservoir assembly 220 is inserted into device 200. Window 2720 may be constructed from plexiglass, styrene, or other translucent or transparent material. Optionally, a top housing label 2722 may be affixed to window 2720. Top housing label 2722 may include indicia such as a company name, logo, color coding for easy identification, or other information. Window 2720 may be affixed to top housing assembly 270 by an adhesive, ultrasonic welding, or other suitable connection method. Retaining clips 2724 retain top housing label 2722 onto top housing assembly 270.

While the exemplary embodiment shown includes top housing assembly 270 being slidably couplable and removable from body 260, other configurations, such as a hinged top housing assembly (not shown), are also contemplated by the present invention. When reservoir 220 is inserted into cradle 2606, information about the fluid in reservoir 220 is readable through aperture 2719. Such information may include the proprietary name of the fluid; the established name of the fluid if such established name exists; an identifying lot or control number; a name of a patient for which a medication may be prescribed; the name of the manufacturer, packer, or distributor of the fluid; or other information useful to identify the patient, the medication, the dosage regimen, or the use of the device. For example, the reservoir may be provided with a label that includes information that would be beneficially visualized by a user of the device after the reservoir is installed. The window or other aperture permits such visualization.

Figure 39:
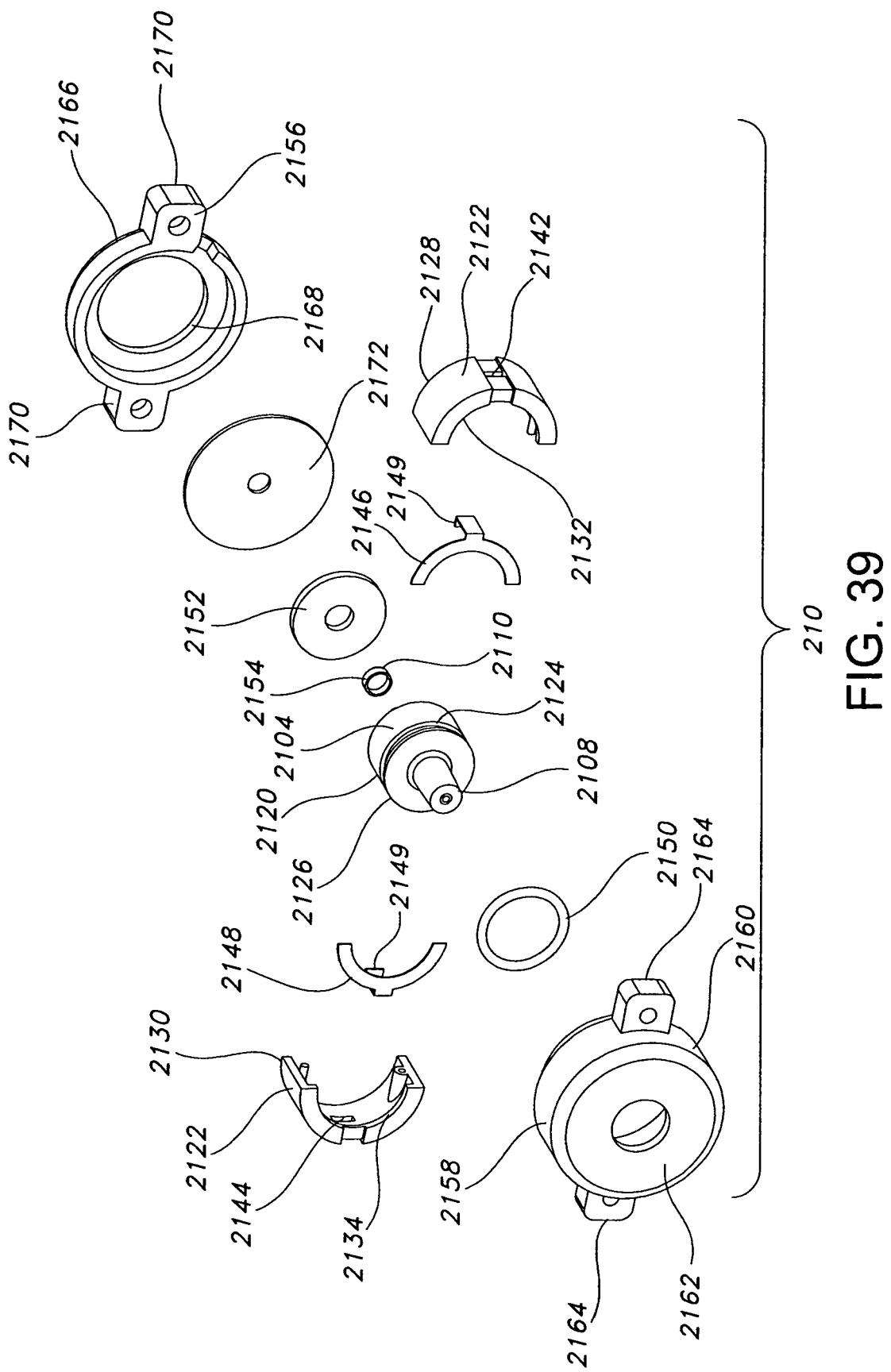

Referring to FIGS. 37-40, transducer assembly 210 includes a transducer shroud 2102 that is inserted into body 260. Remaining portions of transducer assembly 210 are retained within shroud 2102. An exploded view of transducer assembly 210 is shown in FIG. 39. Transducer assembly 210 includes an ultrasonic transducer 2104 having a longitudinally elongated portion 2106 extending from a distal transducer end 2108 to a proximal transducer end 2110.

A lumen 2112 extends axially through transducer 2104 between distal transducer end 2108 and proximal transducer end 2110. Lumen 2112, according to one exemplary embodiment, extends for a length of approximately 18 millimeters (though could be longer or shorter), and has an internal diameter of between approximately 0.70 and approximately 0.80 millimeters (though could be wider or narrower). These dimensions provide an aspect ratio (length of lumen divided by lumen diameter) of between about 22 and about 26. It has been discovered that this aspect ratio for a lumen 2112 of this length generates a desired capillary rise of fluid within lumen 2112 to prime lumen 2112 for advancing the ophthalmic fluid toward the ocular region of the patient. It has been determined that various parameters, including, but not limited to, fluid viscosity, fluid surface energy, surface energy of material defining lumen 2112, and the ability of capillary action of fluid to overcome gravity, may determine a suitable range of aspect ratios for lumen 2112, which may or may not be inside or outside the preferred range of between about 22 and about 26.

Interior of lumen 2112 may be coated with an anti-microbial coating, such as silver, in order to reduce or eliminate microbial growth in lumen 2112 between uses. Anti-microbial coating may be applied to interior of lumen 2112 by a dipping process. In an exemplary embodiment, a distance between distal end 2108 of transducer 2104 and distal end 202 of device 200 is between about 30 mm and about 70 mm. Such distance may be referred to as "nozzle length."

Figure 40:
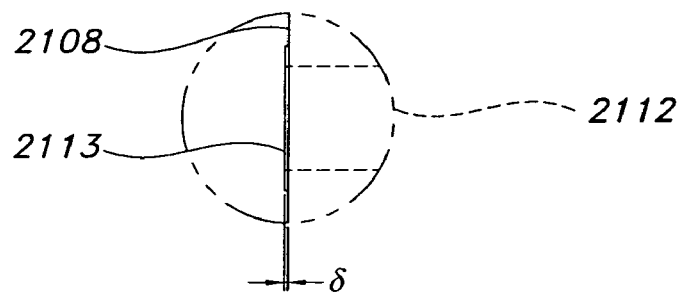

Proximal transducer end 2110 may be chamfered, while distal transducer end 2112 may be generally flat. As shown in FIG. 40, distal transducer end 2112 includes an annular ridge 2113 that extends slightly from the face of distal transducer end 2112. Ridge 2113 extends a distance δ of approximately 0.025 mm from the face of distal transducer end 2112. Without limitation to any particular theory of operation, it is believed that ridge 2113 generates a wicking feature to distribute fluid more evenly next to mesh assembly 230. Transducer 2104 may be constructed from stainless steel or some other, suitable biocompatible material.

A mid-portion 2120 of transducer 2104 is radially larger than distal transducer end 2112 and proximal transducer end 2110. Mid-portion 2120 of transducer 2104 is secured to body by a transducer housing 2122. A housing groove 2124 extends around a periphery of mid-portion 2120 toward a distal end 2126 of mid-portion 2120. Transducer housing 2122 includes a left portion 2128 and a right portion 2130, each of which may be constructed from ABS. Each of left portion 2128 and right portion 2130 are generally semi-circular shells that mate to form an annular housing over a portion of transducer 2104. Each of left and right portions 2128, 2130 includes a lip 2132, 2134, respectively, that extends radially inwardly from a distal end of respective left and right portion 2128, 2130. Lips 2132, 2134 engage housing groove 2124 to retain housing 2122 in an axial position relative to transducer 2104. Each of left and right portion 2128, 2130 of housing 2122 includes a respective slot 2142, 2144 for retaining an electrical contact 2146, 2148, respectively, thereon.

Electrical contacts 2146, 2148 are each arcuate in shape and include a tang 2149 extending therefrom for insertion into its respective slot 2142, 2144. Electrical contacts 2146, 2148 are disposed against distal end 2126 of mid-portion 2120 and extend into housing groove 2124. Electrical contacts 2146, 2148 are in physical contact with transducer 2104 and provide a first electrical connection point for operation of transducer 2104. Electrical contacts 2146, 2148 may be constructed from spring steel or other suitable material.

An o-ring 2150 is disposed around transducer 2104 distally of mid-portion 2120 and seals any space between mid-portion 2120 of transducer 2104 and shroud 2102 to minimize leakage of fluid through shroud 2102. O-ring 2150 may be constructed from silicone or some other suitable material.

An annular piezoelectric device 2152, constructed from piezo ceramic or similar material, is disposed around proximal transducer end 2110 and is bonded to mid-portion 2120 of transducer 2104. Piezoelectric device 2152 provides a second electrical connection point for operation of transducer 2104. An annular insulating sleeve 2154 is disposed against proximal transducer end 2110 and insulates piezoelectric device 2152 from proximal transducer end 2110. Insulating sleeve 2154 may be constructed from a fluorothermoplastic, such as FEP, or some other suitable material.

Shroud 2102 is formed by a proximal shroud portion 2156 and a distal shroud portion 2158 and may be constructed from ABS or another suitable material. Distal shroud portion 2158 includes a generally cylindrical body 2160 having a distal lip 2162. Diametrically opposed flanges 2164 extend from body 2160. Proximal shroud portion 2156 includes a generally cylindrical body 2166 having a proximal lip 2168. Diametrically opposed flanges 2170 extend from body 2160. Each flange 2164 engages a respective flange 2170 to enable a threaded connector (not shown) to releasably couple proximal shroud portion 2156 and distal shroud portion 2158. An annular transducer shroud gasket 2172 is inserted against proximal lip 2168 and seals proximal transducer end 2110 against proximal shroud portion 2156. Gasket 2172 may be constructed from silicone or other suitable material.

Figure 41:
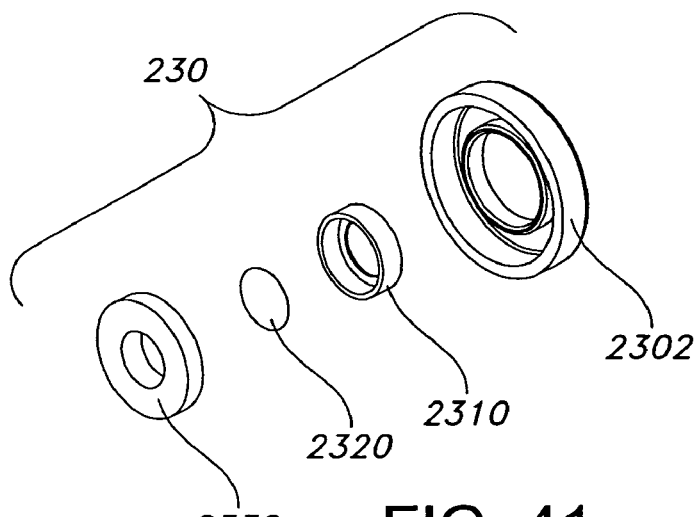
Figure 42:
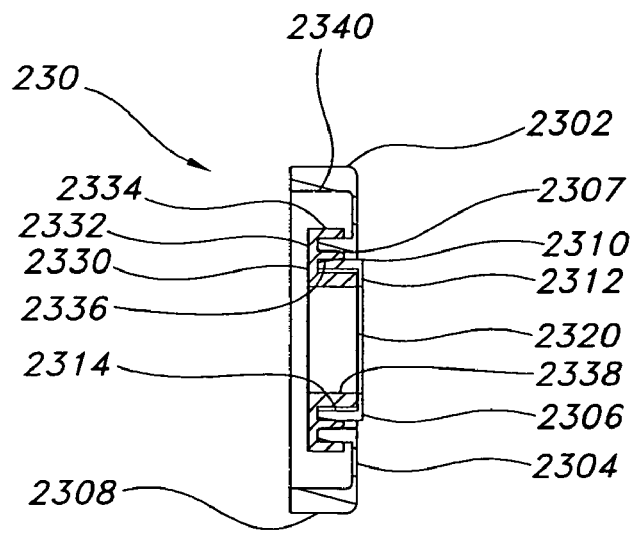
FIG. 42 is a side elevational view, in section, of the mesh cap assembly of FIG. 41.
Figure 43:
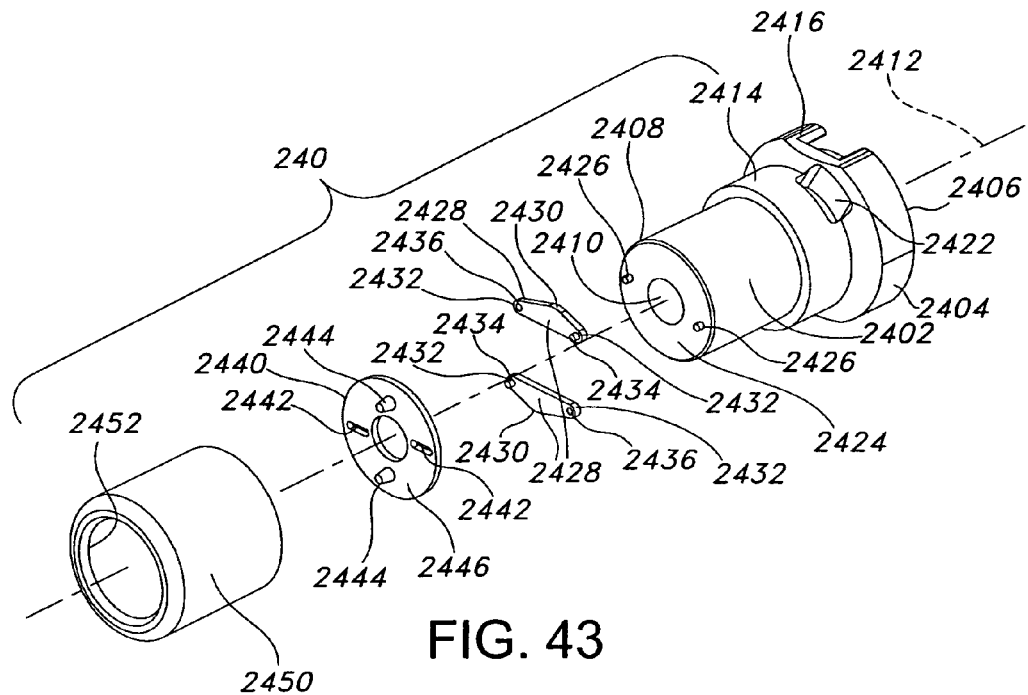
FIG. 43 is an exploded view of a nozzle assembly of the device shown in FIG. 28.
Figure 44:
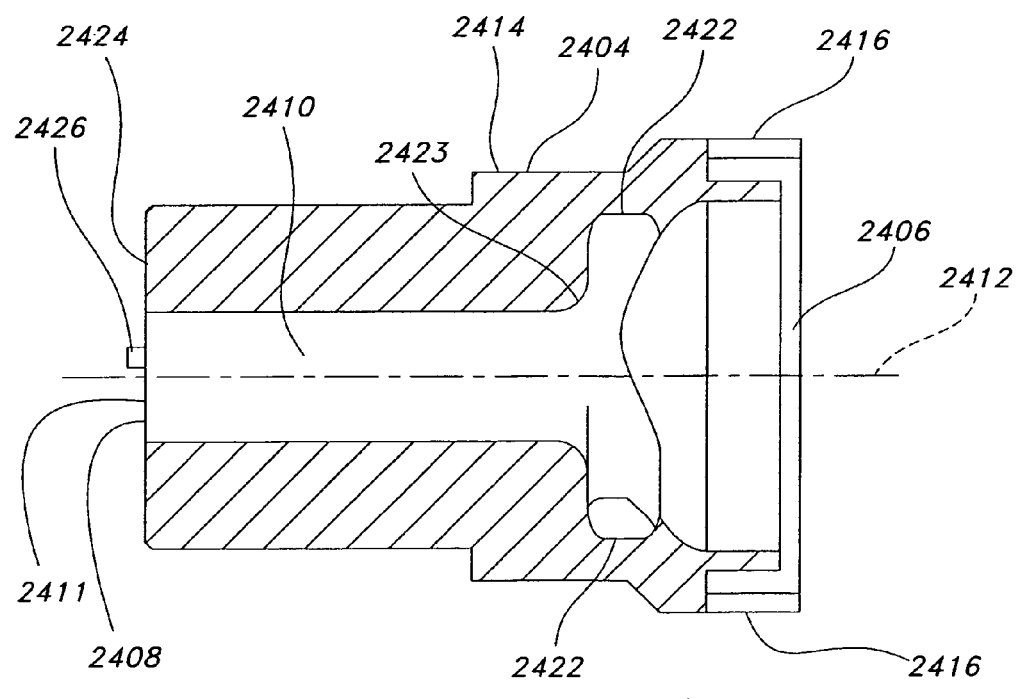
FIG. 44 is a side elevational view, in section, of the nozzle assembly of FIG. 43.

Referring now to FIGS. 41 and 42, mesh cap assembly 230 comprises a generally annular mesh spring 2302, a generally annular mesh carrier plug back 2310, a mesh plate 2320, and a mesh carrier plug 2330. Each of these components will be described in the following paragraphs.

Mesh spring 2302 includes an annular body 2304 having an inner lip 2306 circumscribing an opening 2307 and an outer lip 2308. Both inner lip 2306 and outer lip 2308 extend distally from body 2304. Mesh spring 2302 may be constructed from silicone or some other suitable, biocompatible material.

Mesh carrier plug back 2310 includes an annular body 2312 and a lip 2314 that extends distally from body 2312. Body 2312 has a diameter smaller than that of annular opening in mesh spring 2302 such that mesh carrier plug back 2310 is disposed generally within opening 2307.

Mesh plate 2320 is a thin, flat, circular plate having a thickness of approximately 28 microns and may have a configuration according to any configuration shown in any of FIGS. 12a-12d or 13a-13e. Mesh plate 2320 has a large plurality of openings having diameters of between approximately 3.5 microns and approximately 4 microns.

Mesh 2320 may be constructed from silver plated nickel cobalt. Mesh 2320 may also be coated with Teflon®, tantalum, or some other suitable hydrophobic material to reduce build-up of fluid on mesh plate 2320.

Mesh plug 2330 includes an annular body 2332 having first and second lips 2334, 2336, respectively, that extend proximally and engage inner lip 2306 of mesh spring 2302 therebetween. First lip 2334 and outer lip 2308 form a groove 2340 therebetween. Mesh plug 2330 also includes a mesh lip 2338 that biases mesh plate 2320 against mesh carrier plug back 2310.

Mesh assembly 230 allows mesh plate 2320 to oscillate in response to oscillations of transducer 2104 during operation of device 200. While mesh cap assembly 230 is desired to be used within device 200 to assist in the formation of a mist, those skilled in the art will recognize that it may be possible to omit mesh cap assembly 230 from device 200. Such omission may require additional energy to be transmitted from transducer assembly 210 to the fluid in order to break up fluid particles, forming the desired mist.

Referring to FIGS. 43 and 44, nozzle assembly 240 includes a nozzle 2402 with a body 2404 having an open proximal end 2406, a closeable distal end 2408, and a passage 2410 extending along a longitudinal axis 2412 between proximal end 2406 and distal end 2408. Distal end 2408 of passage 2410 ends in an aperture 2411. Longitudinal axis 2412 is coaxial with axes (not shown) of transducer assembly 210, mesh assembly 230, and nosecone assembly 280. Body 2404 is generally tubular in shape with two distinct step-downs in diameter from proximal end 2406 toward distal end 2408 so that proximal end 2406 has a larger diameter than a central portion 2414 and central portion 2414 has a larger diameter than distal end 2408.

Proximal end 2406 of body 2404 includes a pair of flats 2416 which correspond to nozzle ring flats 2634 and cooperate with nozzle ring flats 2414 to prevent nozzle assembly 240 from rotating with respect to body assembly 260. Proximal end 2406 of body 2404 also includes a circular ridge 2418 that is inserted into groove 2340 formed between mesh spring 2302 and mesh plug 2330 to retain mesh cap assembly 230 in contact with nozzle assembly 240.

A pair of diametrically opposed venturi openings 2422 extend through body 2404 at an interface between proximal end 2406 and central portion 2414. Venturi openings 2422 fluidly communicate with passage 2410 to entrain air in mist when device 200 is operated and to develop flow through nozzle 2402. Venturi openings 2422 communicate with passage 2410 at an angle relative to nozzle axis 2412. The angle selected for the orientation of venturi openings 2422 is optionally between about 30 degrees and about 150 degrees with respect to the nozzle axis 2412. More preferably, the angle between the axis of a venturi opening 2422 and nozzle axis 2412 is from about 30 degrees to about 90 degrees, the angle being defined by the vectors of the flow of air through venturi opening 2422 and the fluid in nozzle passage 2410 downstream of venturi openings 2422 and the point at which the flows meet. For example, an angle of 30 degrees provides the venturi openings 2422 with a significant vector component in the downstream direction of fluid flow.

As shown in FIG. 44, a transition portion 2423 between venturi openings 2422 and passage 2410 is curved, with a radius between about 1 mm and about 2 mm, and with an exemplary radius of curvature of about 1.3 mm. This radius helps to establish a laminar flow pattern.

Nozzle 2402 collimates the mist generated by transmission of the fluid through mesh cap assembly 230. Without limitation to any particular theory of operation, it is believed that air drawn into passage 2410 through venturi openings 2422 follows the curvature of transition portion 2423 and hugs the wall of passage 2410, forcing the misted fluid toward longitudinal axis 2412, thus forming a collimated plume of mist. This helps to maintain the integrity of the mist plume as it travels to the ocular region. In this manner, a narrow, yet controlled column of mist is applied to the target area of the ocular region, thus reducing waste of fluid, assuring adequate dosage, and delivering a controlled application of fluid.

Distal end 2408 of nozzle 2402 includes an annular face 2424. A pair of diametrically opposed mounting posts 2426 extend longitudinally and distally from annular face 2424. A pair of shutters 2428 are pivotally mounted on mounting posts 2426, with one shutter 2428 mounted on each mounting post 2426 such that shutters 2428 are proximate aperture 2411. Each shutter 2428 is generally triangularly shaped with an obtuse angle 2430 and two acute angles 2432. Each corner is generally rounded. For each shutter 2428, a shutter pin 2434 extends longitudinally distally from a corner having an acute angle 2432. A pivot opening 2436 is formed in the corner having the remaining acute angle 2432. The shutters 2428 are juxtaposed from each other such that the longer sides of each shutter 2428 are facing each other, with each pivot opening 2436 disposed over a respective mounting post 2426.

A shutter actuator 2440 opens and closes shutters 2428 as shutter actuator 2440 rotates relative to nozzle 2402. Shutter actuator 2440 is an annular ring having a pair of parallel slots 2442 formed therein. Slots 2442 are slightly offset on either side of longitudinal axis 2412. A pair of diametrically opposed actuator knobs 2444 extend longitudinally and distally from shutter actuator 2440.

Each shutter pin 2434 is inserted into one of slots 2442 in shutter actuator 2440. Shutter actuator 2440 is rotatable about longitudinal axis 2412 such that shutter pins 2434 slide along their respective slot 2442, pivoting each shutter 2428 about its respective pivot opening 2436, rotating longer sides of each shutter 2428 toward or away from each other, depending on the direction of rotation of shutter actuator 2440 relative to nozzle 2402, closing or opening passage 2410.

A nozzle capture cap 2450 is disposed over distal end 2408 of nozzle 2402. Nozzle capture cap 2450 is generally tubular, with a lip 2452 that extends inwardly toward longitudinal axis 2412 and engages shutter actuator 2440 to retain shutter actuator 2440 against nozzle 2402. All of the components of nozzle assembly 240 may be constructed from acetyl or some other suitable material.

Figure 45:
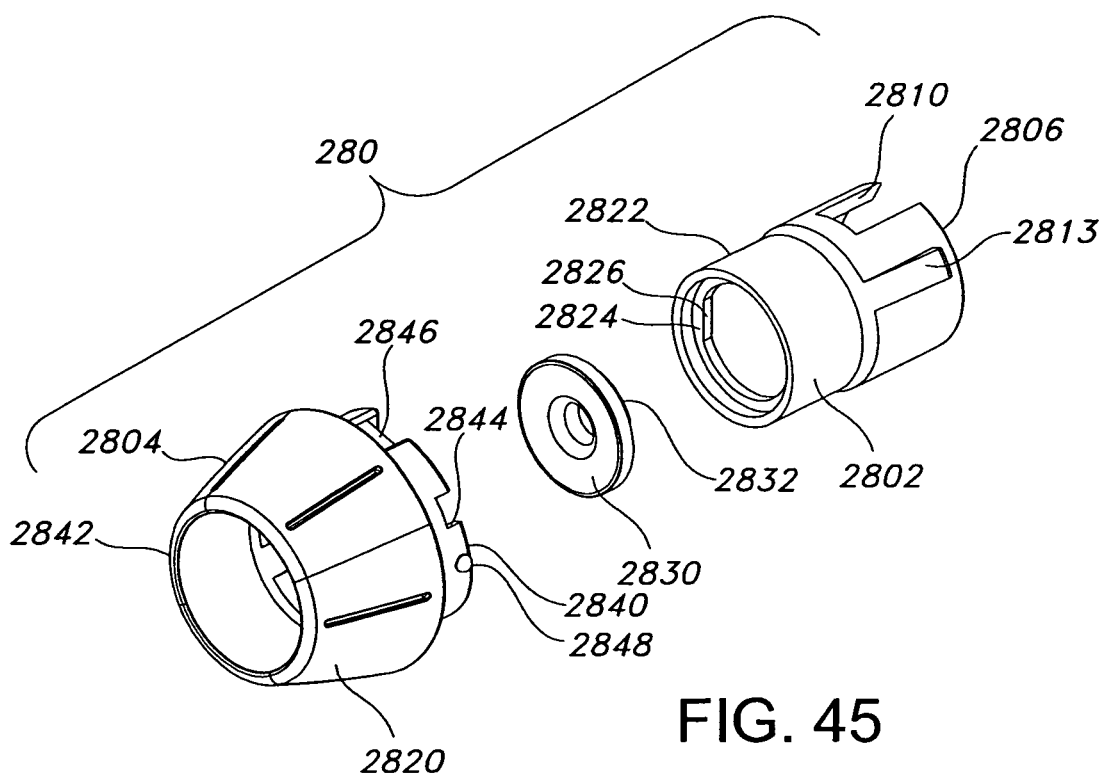
FIG. 45 is an exploded view of a nosecone assembly of the device shown in FIG. 28.
Figure 46:
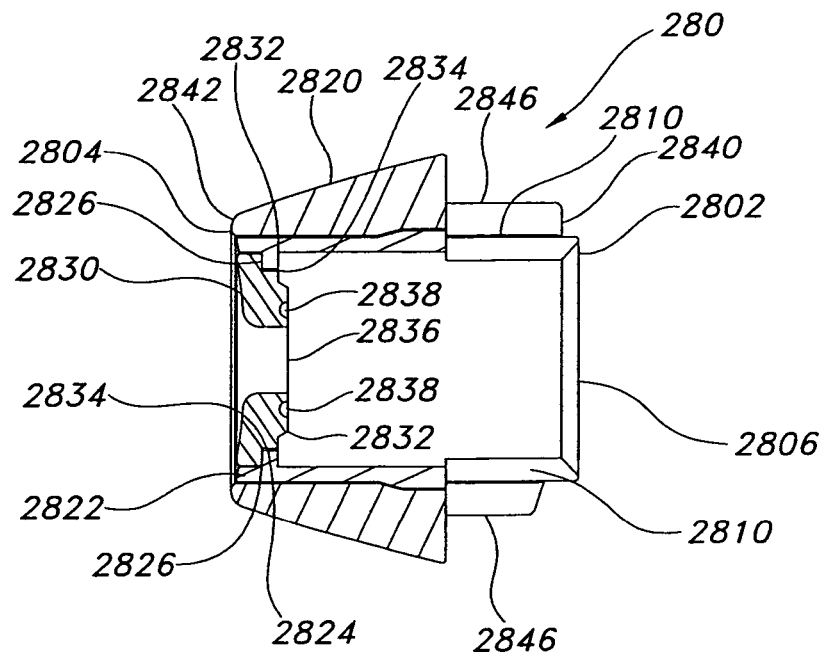
FIG. 46 is a side elevational view, in section, of the nosecone assembly of FIG. 45.

Referring now to FIGS. 45 and 46, nosecone assembly 280 is disposed over nozzle assembly 240 and rotatably coupled to insert portion 2430. Nosecone assembly 280 includes a generally tubular nosecone lens 2802 that may be constructed from transparent or translucent material, such as styrene. Nosecone lens 2802 is used as a light pipe to transmit light from LED's to distal end 2804 of nosecone assembly 280. Nosecone lens 2802 includes a proximal portion 2806 having a pair of diametrically opposed cutouts 2810. Cutouts 2810 provide an air path through nosecone assembly 280 to allow air to flow through venturi openings 2422 during operation of device 200.

Proximal portion 2806 of nosecone lens 2802 also includes a pair of diametrically opposed wedges 2413 (only one wedge 2413 shown in FIG. 45) that are disengaged from an arming switch 2542 in handle assembly 250 when nosecone assembly 280 is rotated to the "OFF" or closed position and engage arming switch 2542 when nosecone assembly 280 is rotated to the "ON" or open position.

A distal portion 2822 of nosecone lens 2802 includes a circumferential lip 2824 that extends inwardly from nosecone lens 2802. Lip 2824 includes a pair of diametrically opposed flats 2826 that receive and retain a nosecone lens cover 2830.

Nosecone lens cover 2830 is a generally annular plate that is inserted into distal portion 2822 of nosecone lens 2802. Nosecone lens cover 2830 includes a recessed portion 2832 that is inserted into lip 2824. Recessed portion 2832 includes mating flats 2834 that mate with flats 2826 in lip 2824. A proximal face 2836 of recessed portion 2832 includes a pair of diametrically opposed indents 2838. Indents 2838 accept and retain actuator knobs 2444 on shutter actuator 2440 such that rotation of nosecone assembly 280 rotates shutter actuator 2440, opening and closing shutters 2428.

Nosecone 2820 is generally frusto-conically shaped, but may have a wide variety of shapes or configurations, having a proximal end 2840 and a distal end 2842. Proximal end 2840 includes a pair of diametrically spaced cutouts 2844 (only one cutout shown in FIG. 45) that align with LED's 2637 when nosecone assembly 280 is rotated to an open position.

Proximal end 2840 also includes a pair of diametrically opposed venturi cutouts 2846 that fluidly communicate with venturi openings 2422 when nosecone assembly 280 is rotated relative to nozzle assembly 240 to open shutters 2428. Proximal end 2840 also includes a pair of nubs 2848 (only one nub 2848 shown in FIG. 45) that are inserted into grooves 2642 in nosecone ring 2640. Nosecone 2820 and nosecone lens cover 2830 may be constructed from ABS or some other suitable material.

Figure 47:
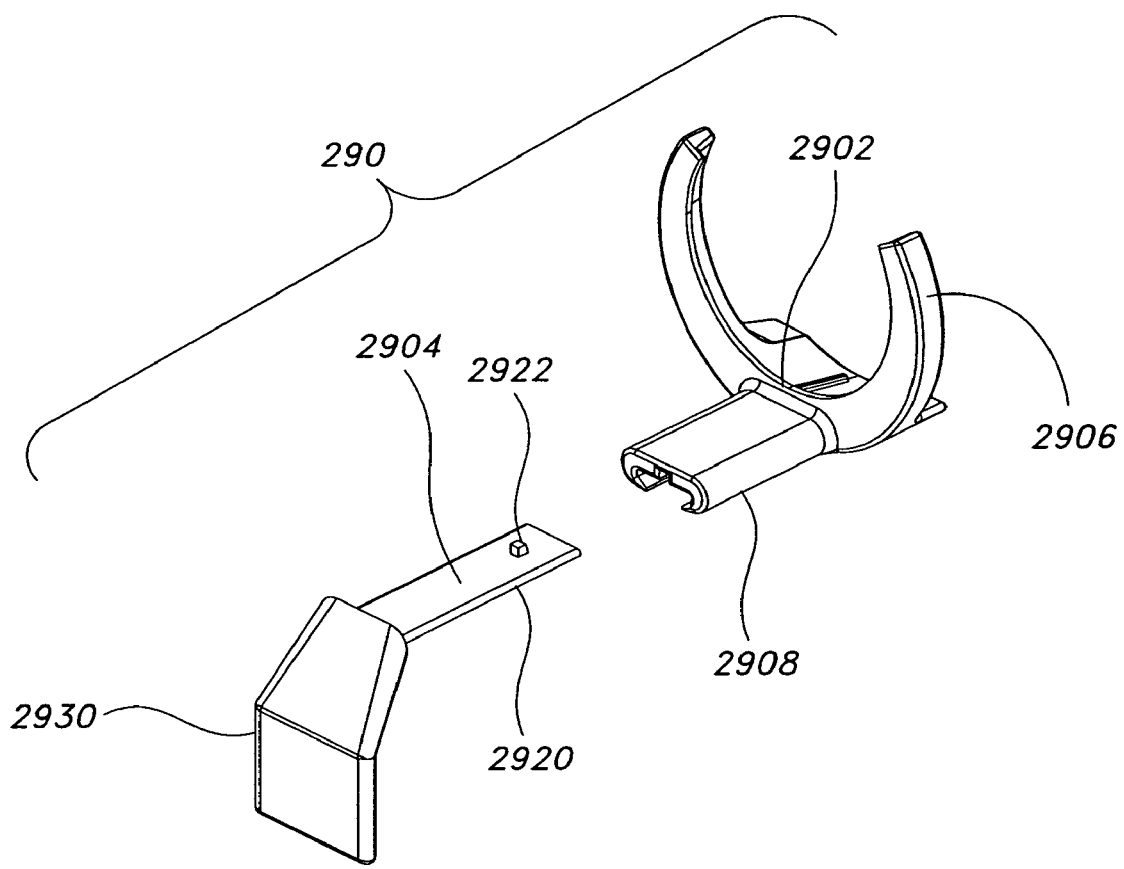
FIG. 47 is an exploded view of a spacer assembly of the device shown in FIG. 28.

A spacer assembly 290 is shown in FIGS. 31 and 47. Spacer assembly 290 is used to space device 200 a predetermined distance from a patient's eye prior to operating device 200 to transmit a mist of fluid from device 200 toward a patient's eye. Spacer assembly 290 may be constructed from nylon or some other suitable material, and includes a clip 2902 and an extension 2904 that is extendably coupled to clip 2902.

Clip 2902 includes an arcuate portion 2906 that traces an arc of greater than 180 degrees. Clip 2902 releasably snaps onto proximal end 2840 of nosecone 2820. An extension slider 2908 extends distally from clip 2902. Referring to FIG. 31, extension slider 2908 includes a proximal detent 2910 that releasably retains extension 2904 in a compressed position. Extension slider 2908 also includes a pair of elongated slots 2912 that allow extension of extension 2904 relative to extension slider 2908. A nub 2913 is disposed between slots 2912 to stop extension of extension 2904 after approximately half travel along extension slider 2908. A tang 2914 is disposed at distal end of extension slider 2908 to restrict movement of extension 2904 out of extension slider 2908.

Extension 2904 includes a proximate slide 2920 having a nub 2922 that fits within proximal detent 2910 when extension 2904 is in compressed position. Nub 2922 also fits within slots 2912 and allows extension of extension 2904 relative to extension slider 2908.

Extension 2904 includes a distal face piece 2930 that is intended to engage the inferior orbital rim (not shown) on a patient during use of device 200. Spacer assembly 290 is adjustable over a range of between approximately 10 and approximately 30 millimeters to adjust for different size patients with which device 200 is intended to be used. For example, the spacer assembly 290 can provide a selection of predetermined distances that may be selected depending on the orbital anatomy of the individual to whom the ophthalmic fluid is being delivered, the velocity or other characteristic of the plume of mist, or other factors. Spacer assembly 290 may be removed from nosecone 2820, such as after use on a patient, and a replacement spacer assembly 290 or the cleaned spacer assembly 290 may be clipped to nosecone 2820 prior to use on the next patient.

Figure 48:
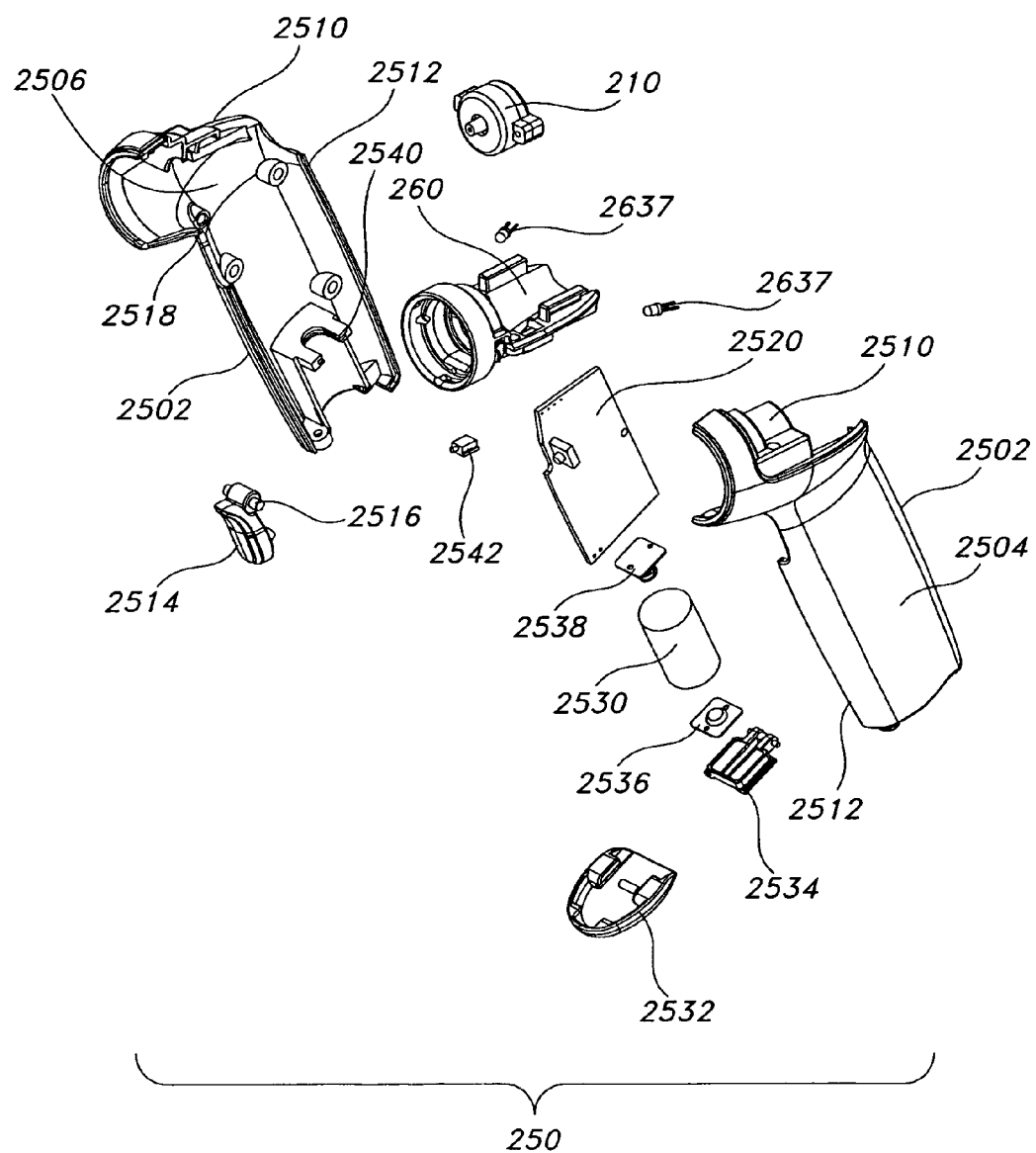
FIG. 48 is an exploded view of a handle assembly of the device shown in FIG. 28.

Referring to FIGS. 30 and 48, handle assembly 250 is coupled to body 260. Handle assembly 250 includes a handle 2502 that is constructed from a left hand portion 2504 and a right hand portion 2506. As shown in FIG. 28, handle assembly 250 has a longitudinal axis 2508 that extends at an angle of more than 90 degrees, preferably between about 105 degrees and about 125 degrees, from longitudinal axis 2412, with an exemplary angle of about 115 degrees. This range of angles provides ergonomic comfort for a person using device 200. Device 200 may be used by a professional or an assistant on a separate patient, or alternatively, device 200 may be used by an individual for self-administration.

Referring back to FIG. 48, handle 2502 includes an upper portion 2510 that receives and retains body 260. A lower grip portion 2512 houses electrical and electronic components to operate device 200. Handle assembly 250 and body 260 can be provided with a wide variety of ornamental configurations to render the device 200 aesthetically pleasing.

Lower grip portion 2512 includes an activation switch 2514 that is pivotally coupled to handle 2502 about a pivot 2516, which is inserted into a pivot receiver 2518 in each of left hand portion 2504 and right hand portion 2506 (only pivot receiver 2518 in right hand portion 2506 is shown in FIG. 48.) Operation of activation switch 2514 initiates operation of device 200 to generate a mist of ophthalmic fluid from device 200. Handle 2502 and activation switch 2514 may be constructed from ABS or some other suitable material.

A printed circuit board (PCB) 2520 is disposed within lower grip portion 2512. PCB 2520 contains all electronic and logic circuits used to operate device 200. A battery 2530 is also disposed within lower grip portion 2512. Battery 2530 may be a CR2 lithium battery or other suitable power supply. Battery 2530 may be rechargeable or replaceable. To facilitate replacement of battery 2530, an outer battery door 2532 is releasably coupled to bottom of lower grip portion 2512.

An inner battery door 2534 is pivotally coupled to lower grip portion 2512, just above outer battery door 2532. Inner battery door 2534 and outer battery door 2532 may be constructed from ABS. Inner battery door 2534 retains positive battery contact 2536, which engages negative terminal of battery 2530 when inner battery door 2534 and outer battery door 2532 are in closed positions.

A negative battery contact 2538 is inserted into a contact slot 2540 in right hand portion 2506 of handle 2502. Negative battery contact 2538 engages positive terminal of battery 2530 and electrically couples battery 2530 to PCB 2520.

Arming switch 2542 is disposed within handle assembly 260 proximate to nosecone assembly 280 such that rotation of nosecone assembly 280 from a closed position to an open position engages arming switch 2542, arming device 200. Arming switch 2542 is electrically coupled to PCB 2520 such that, when arming switch 2542 is armed, activation of activation switch 2514 results in operation of transducer 2104, but when arming switch 2542 is not armed, activation of activation switch 2514 will not result in operation of transducer 2104.

Figure 49:
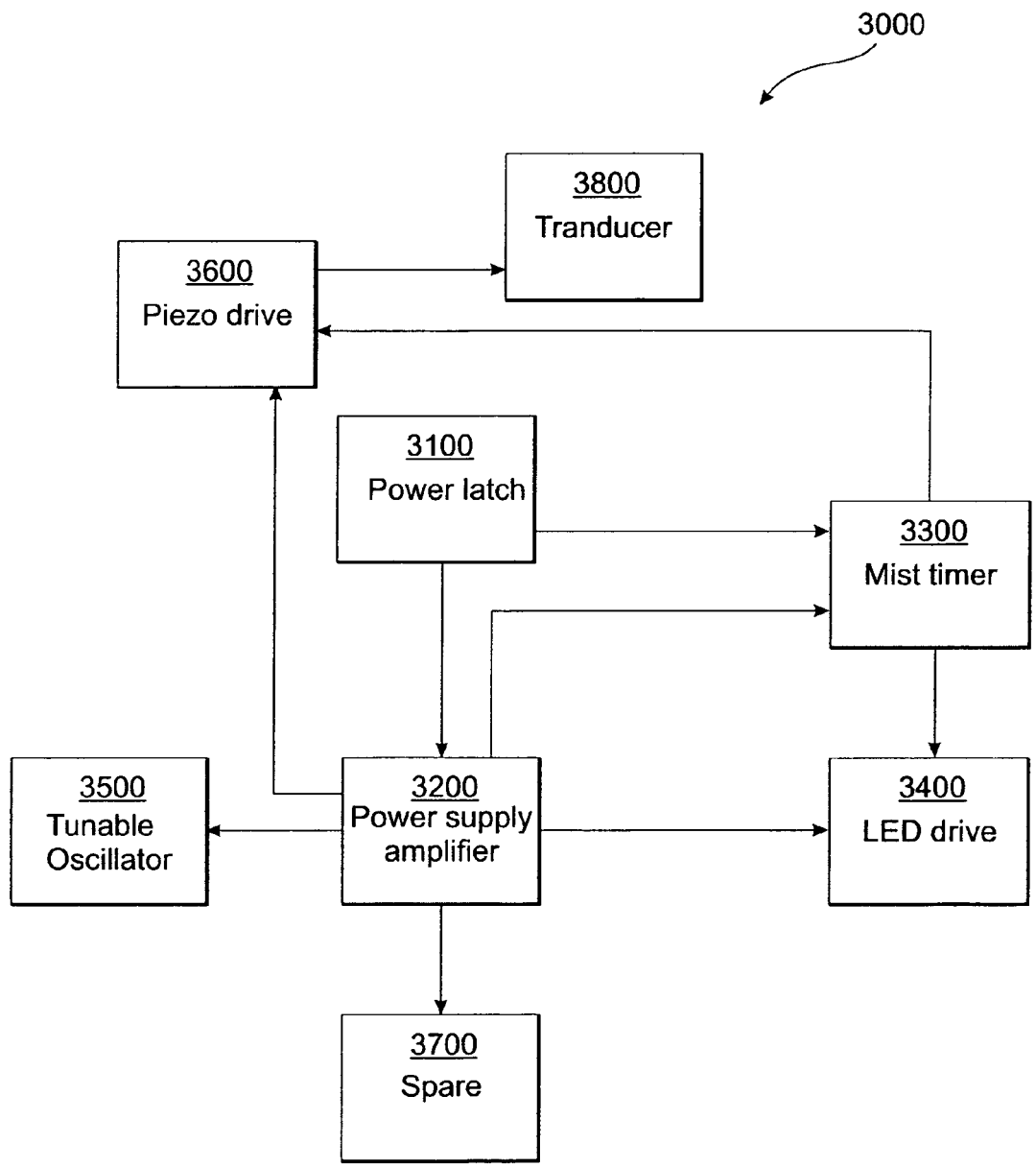
FIG. 49 is a schematic block diagram of a control system of the device shown in FIG. 28.

FIG. 49 illustrates an electronic block diagram of components on the PCB 2520 according to an exemplary embodiment of the present invention. PCB 2520 includes a power latch circuit 3100 that activates the misting operation of device 200. In an exemplary embodiment, when activation switch 2514 of the device 200 is pressed (such as in direction towards handle assembly 250), power latch circuit 3100 is activated and completes the electric circuit of PCB 2520. In an exemplary embodiment of power latch circuit 3100 illustrated in FIG. 50A, power latch circuit 3100 draws power from battery 2530 that is electrically coupled to power latch circuit 3100 to activate the misting operation of device 200.

When device 200 is activated, power from power latch circuit 3100 is sent to power supply amplifier circuit 3200. Power supply amplifier circuit 3200 steps up the voltage from battery 2530 and sends power to the circuit components on PCB 2520. In an exemplary embodiment of power supply amplifier circuit 3200 shown in FIG. 50B, power supply amplifier circuit 3200 includes a voltage step-up integrated circuit that amplifies the voltage from power latch circuit 3100.

Figure 50A:
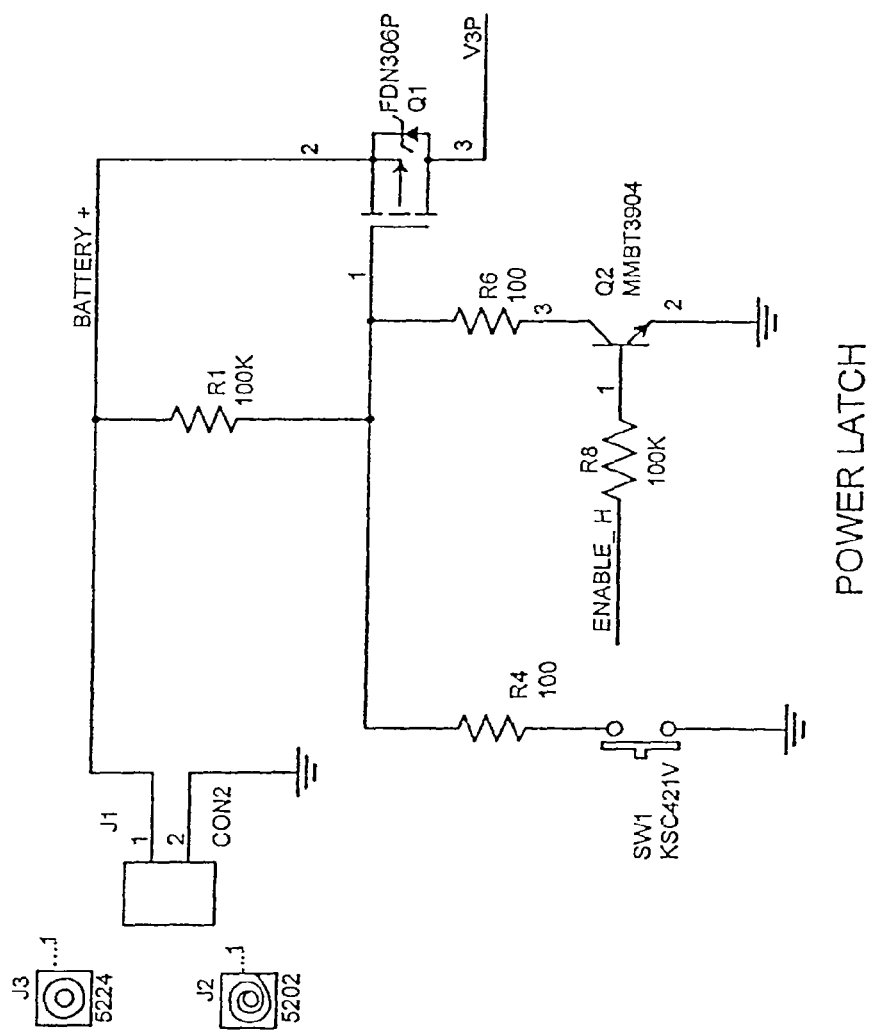
FIG. 50A is an exemplary schematic diagram of the power latch shown in FIG. 49.
Figure 50B:
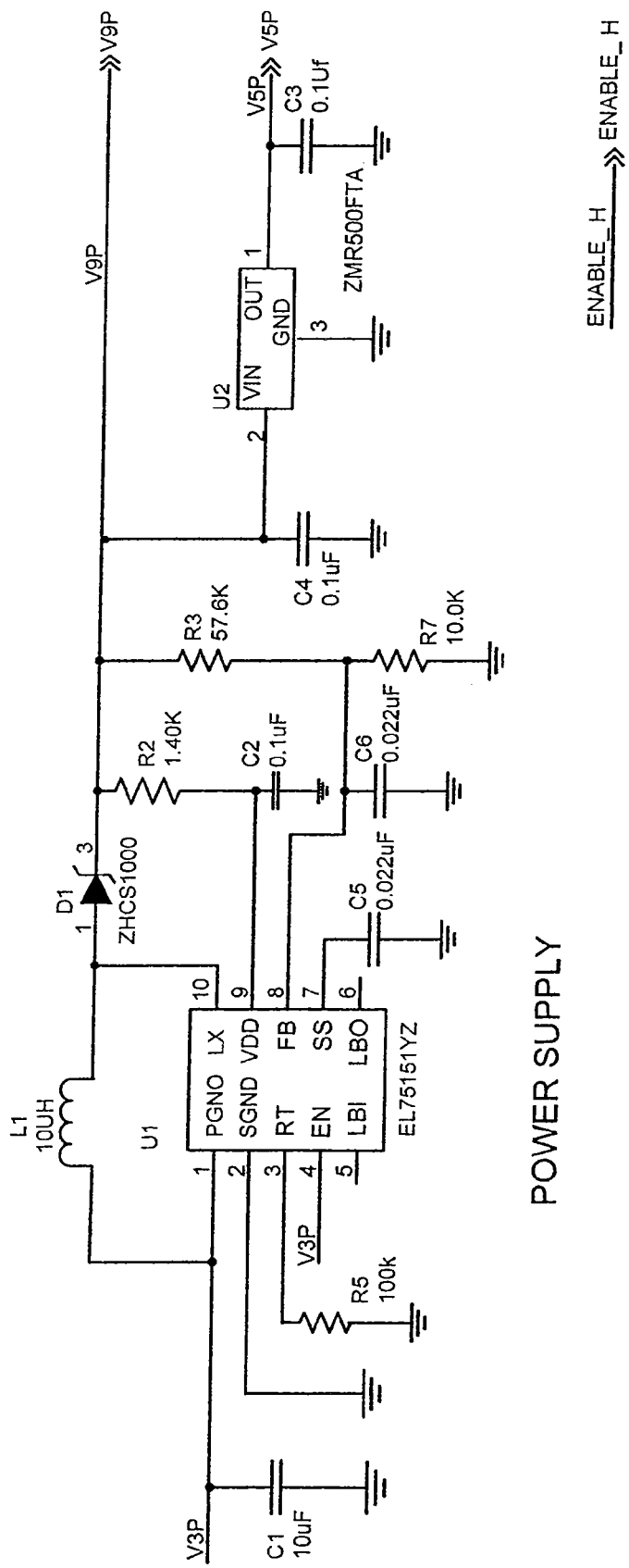
FIG. 50B is an exemplary schematic diagram of the power supply shown in FIG. 49.
Figure 50C:
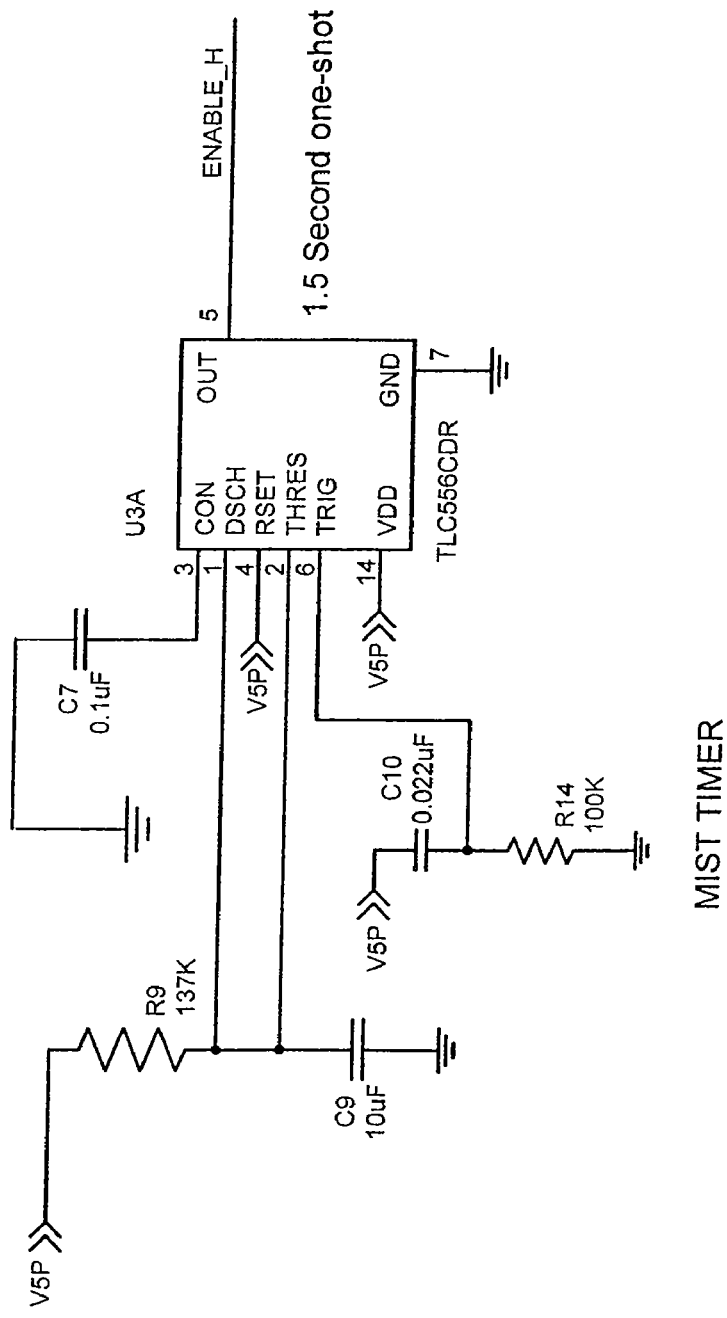
FIG. 50C is an exemplary schematic diagram of the mist timer shown in FIG. 49.
Figure 50D:
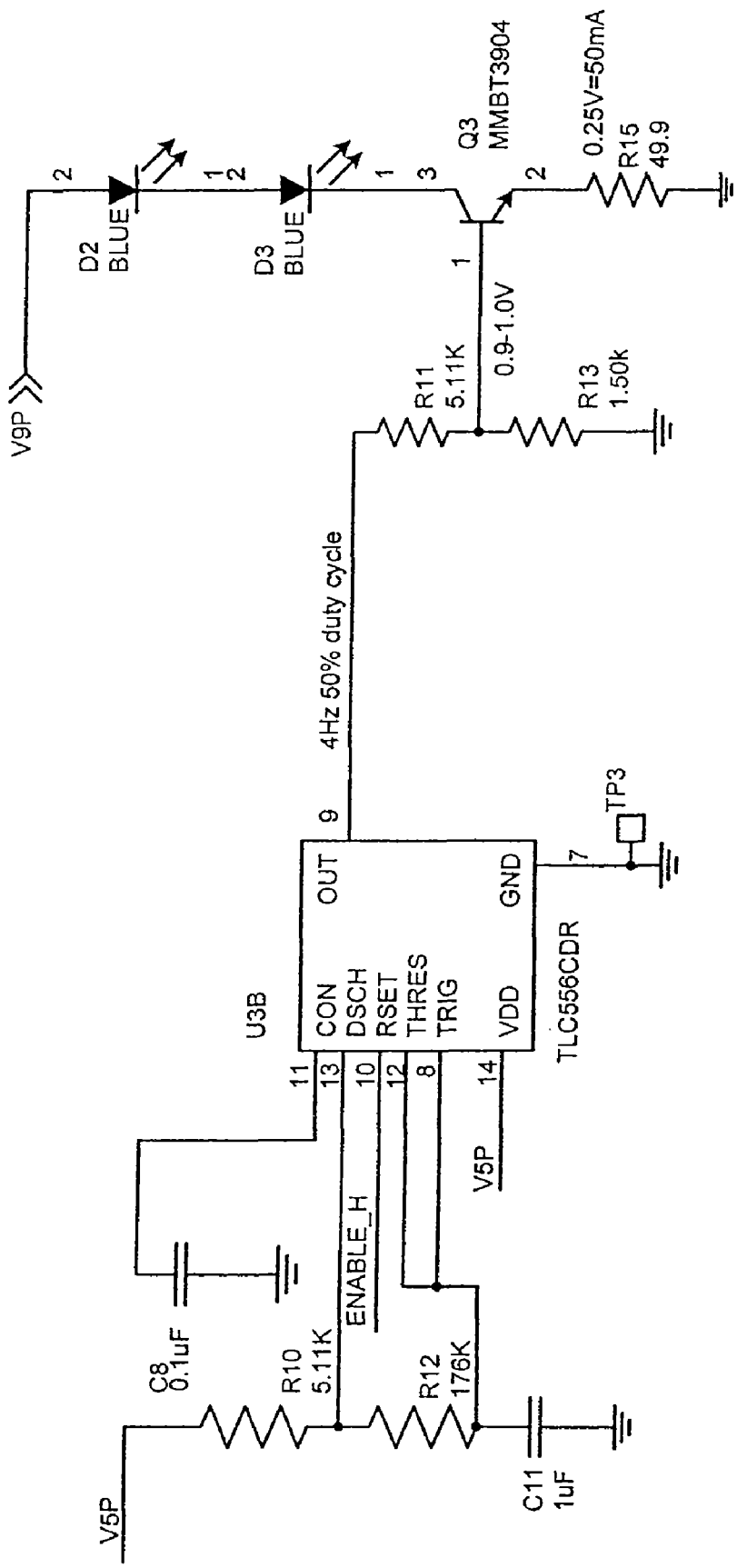
FIG. 50D is an exemplary schematic diagram of the LED drive shown in FIG. 49.

In an exemplary embodiment, when power from power supply amplifier circuit 3200 and an electric signal from power latch circuit 3100 is supplied to mist timer circuit 3300, mist timer circuit 3300 measures the length of time in which power latch circuit 3100 is activated. Mist timer circuit 3300 sends electric signals to an LED drive circuit 3400 and a piezo drive circuit 3600. The electric signal sent from mist timer circuit 3300 to LED drive circuit 3400 causes LEDs 2637 to blink intermittently when power to the power supply amplifier 3200 is received by LED drive circuit 3400. In an alternative embodiment, LED drive circuit 3400 may receive an electric signal from an arming circuit, which is closed by arming switch 2542, which may illuminate LEDs 2637 continuously when the electric signal from mist timer circuit 3300 is not received by LED drive circuit 3400. Exemplary embodiments of mist timer circuit 3300 and LED drive circuit 3400 are illustrated in FIGS. 50C and 50D, respectively.

Figure 50E:
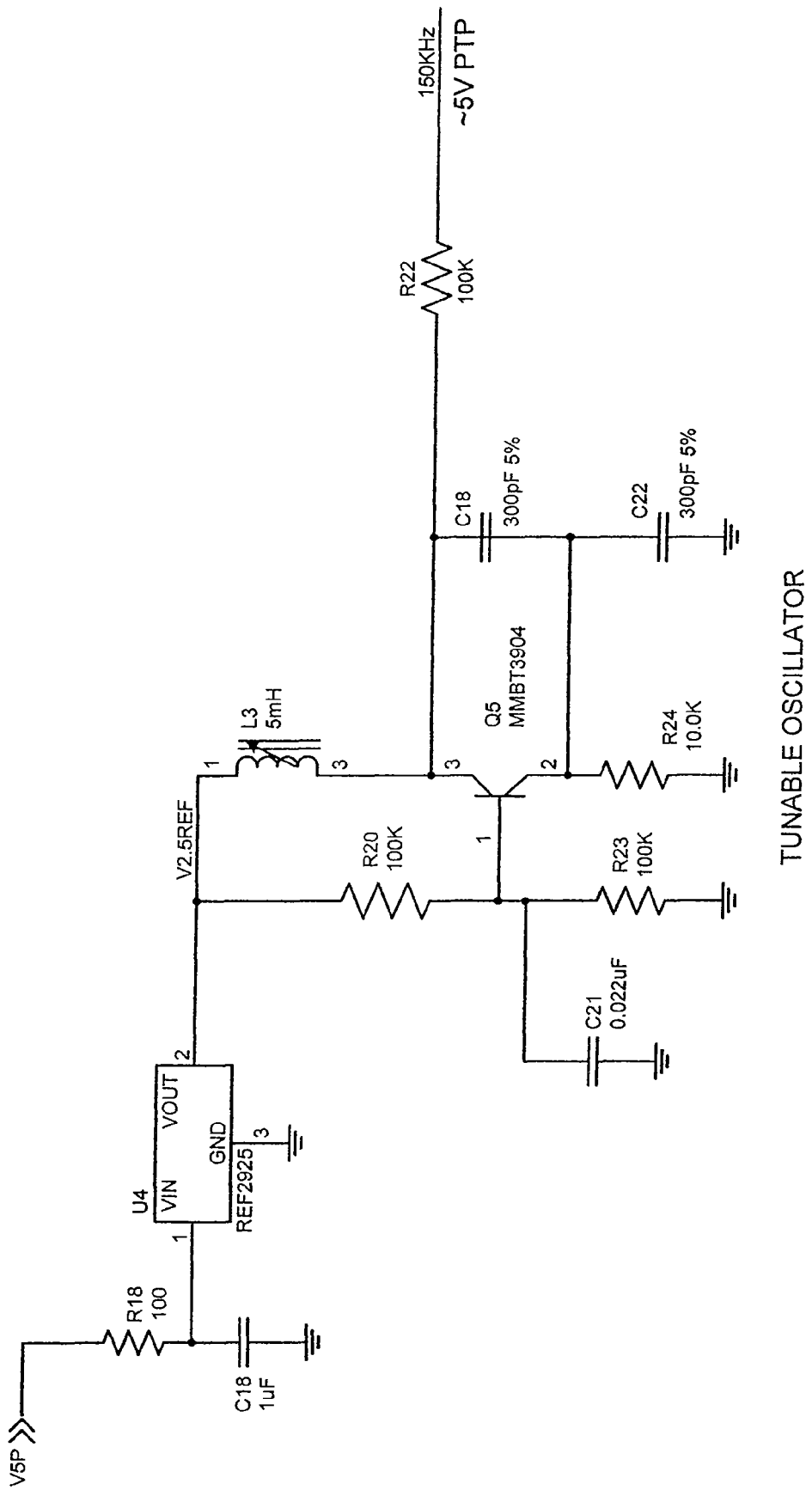
FIG. 50E is an exemplary schematic diagram of the tunable oscillator shown in FIG. 49.
Figure 50F:
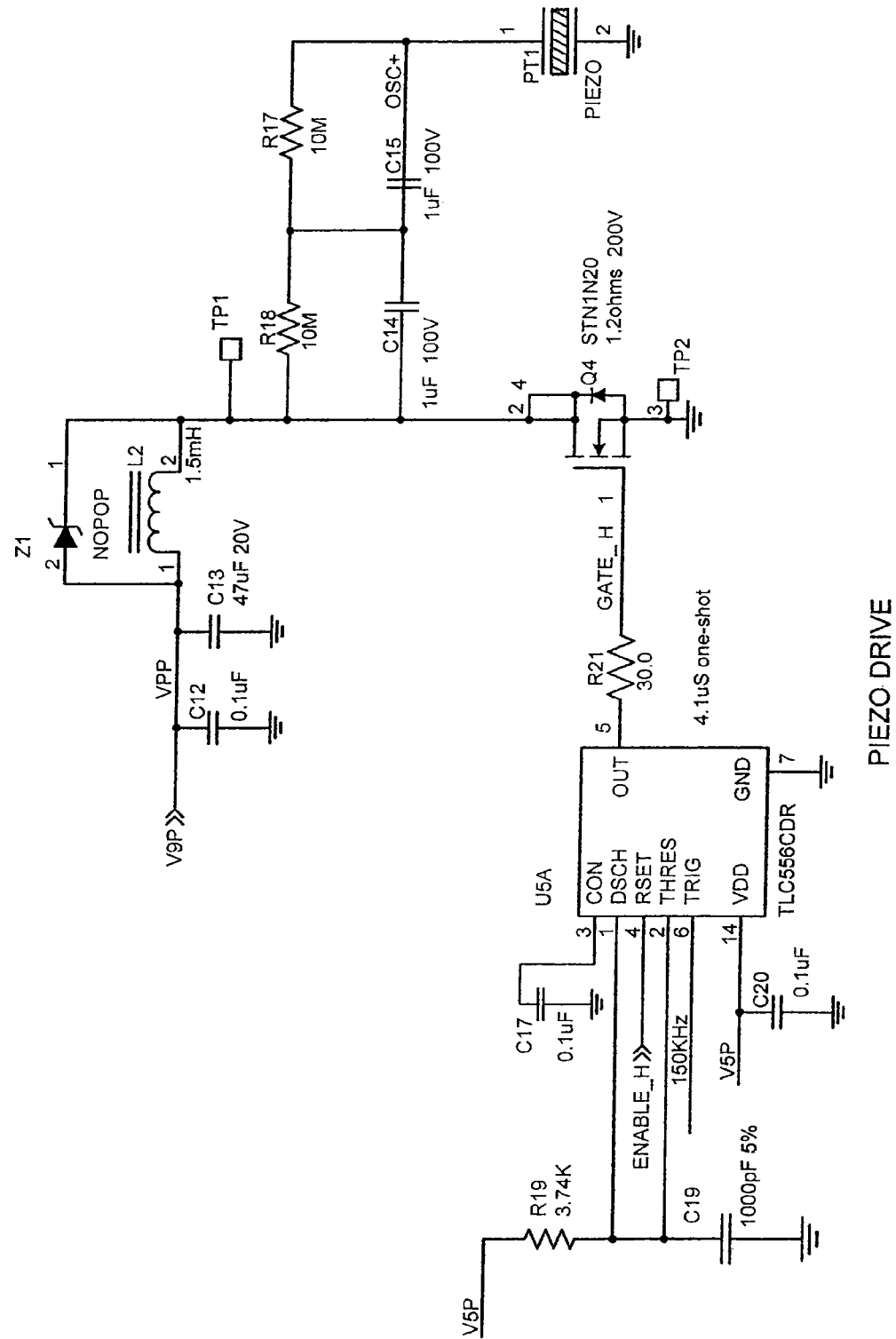
FIG. 50F is an exemplary schematic diagram of the piezo drive shown in FIG. 49.

The operation of a tunable oscillator circuit 3500 will now be described with reference to FIGS. 49 and 50E. It should be noted that the exemplary circuits and circuit components shown in the figures, including the values of such circuit components, are for purposes of illustration only. The invention is not limited to any particular circuit, circuit component or component value.

Figure 50G:
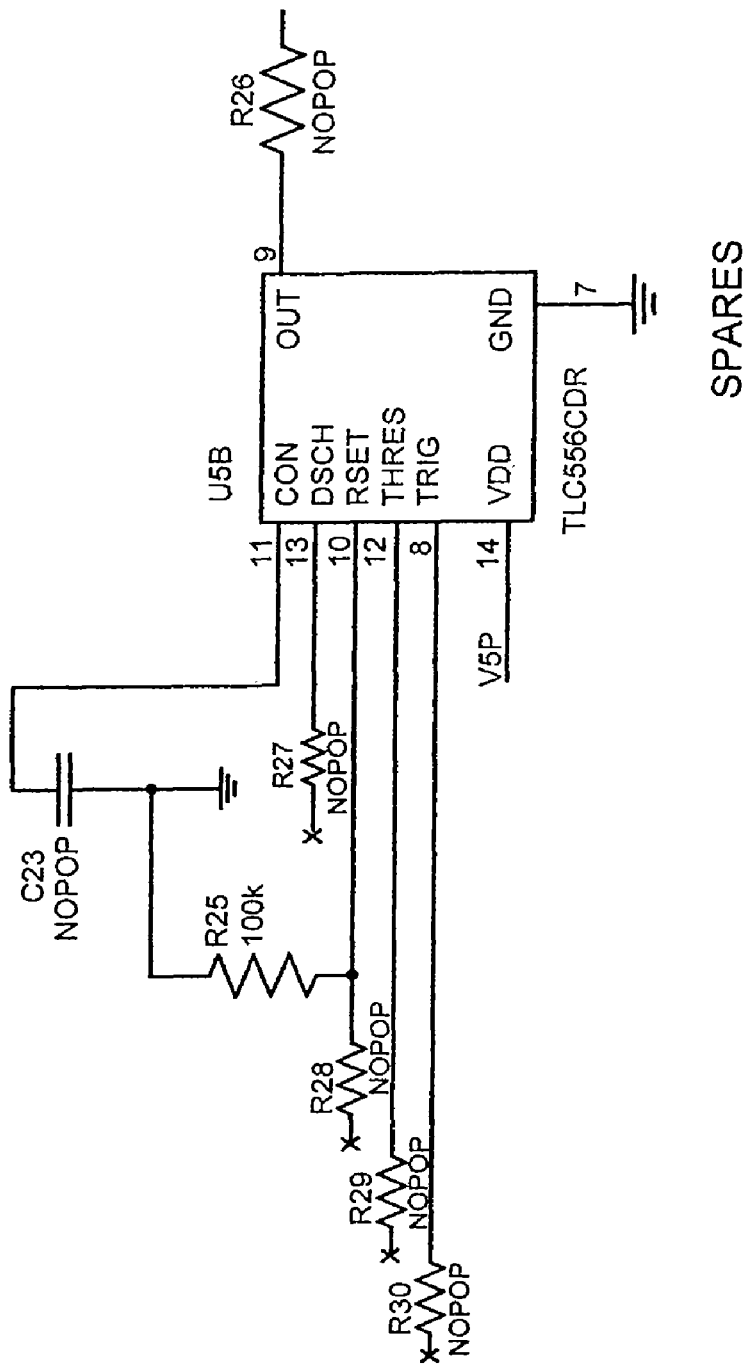
FIG. 50G is an exemplary schematic diagram of the spare circuit shown in FIG. 49.

Tunable oscillator circuit 3500 receives power from power supply amplifier circuit 3200 and sends an electric signal to a piezo drive circuit 3600. The electric signal which is output from tunable oscillator circuit 3500 includes a resonant frequency that causes piezoelectric device 2152 to resonate at the resonant frequency. In an exemplary embodiment, when piezo drive circuit 3600 illustrated in FIGS. 49 and 50F receives power from power supply amplifier circuit 3200 and electric signals from tunable oscillator circuit 3500 and mist timer circuit 3300, misting of fluid in device 200 is initiated. In an exemplary embodiment, misting is initiated when piezoelectric device 2152 resonates at the resonant frequency of tunable oscillator circuit 3500 for a period of time determined by the electric signal from mist timer circuit 3300. A spare circuit 3700, illustrated in FIGS. 49 and 50G, is provided for the inclusion of additional features, which may include, but are not limited to, counters, alarms, adjustable timing, battery low power indicator, fluid low volume indicator, etc.

Although not shown, tunable oscillator circuit 3500 may include a software feedback loop so that PCB 2520 can track the resonant frequency and lock on to it. Such feedback loop helps device 200 work at optimum efficiency despite variations in temperature, fluid content, mechanical constraints, etc. that may shift the resonant frequency of transducer 2104.

Figure 51:
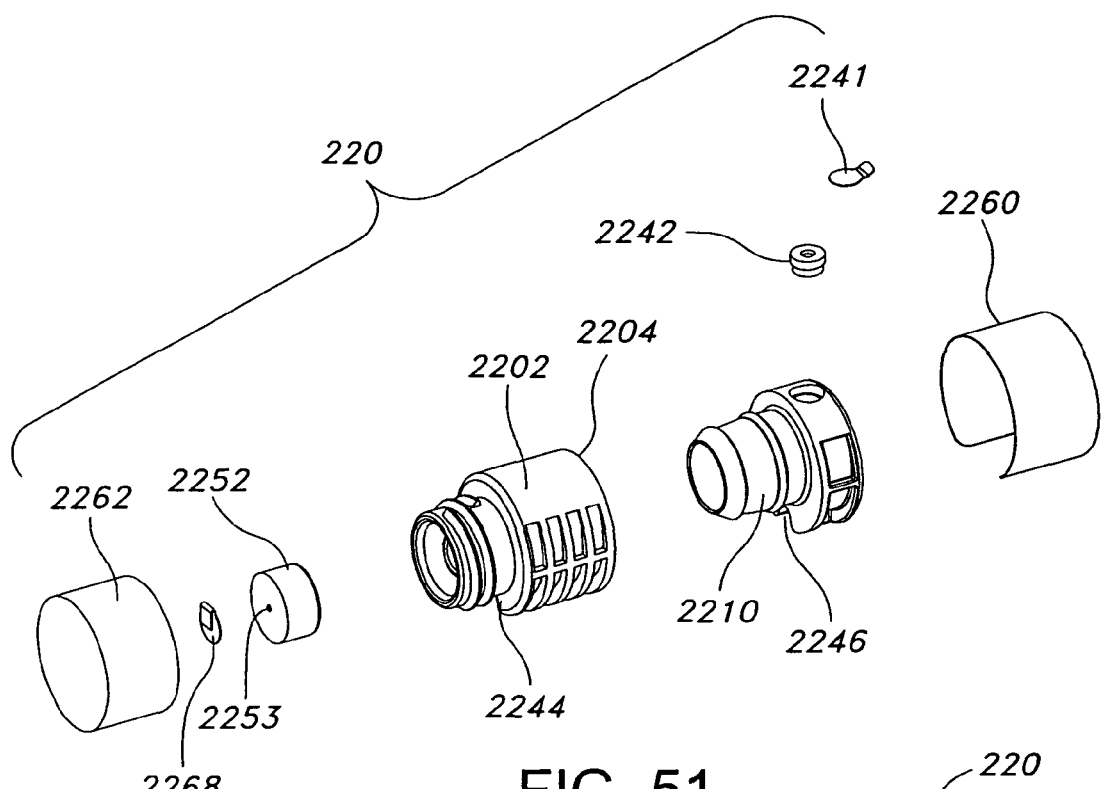
FIG. 51 is an exploded view of a reservoir assembly used in the device shown in FIG. 28.
Figure 52:
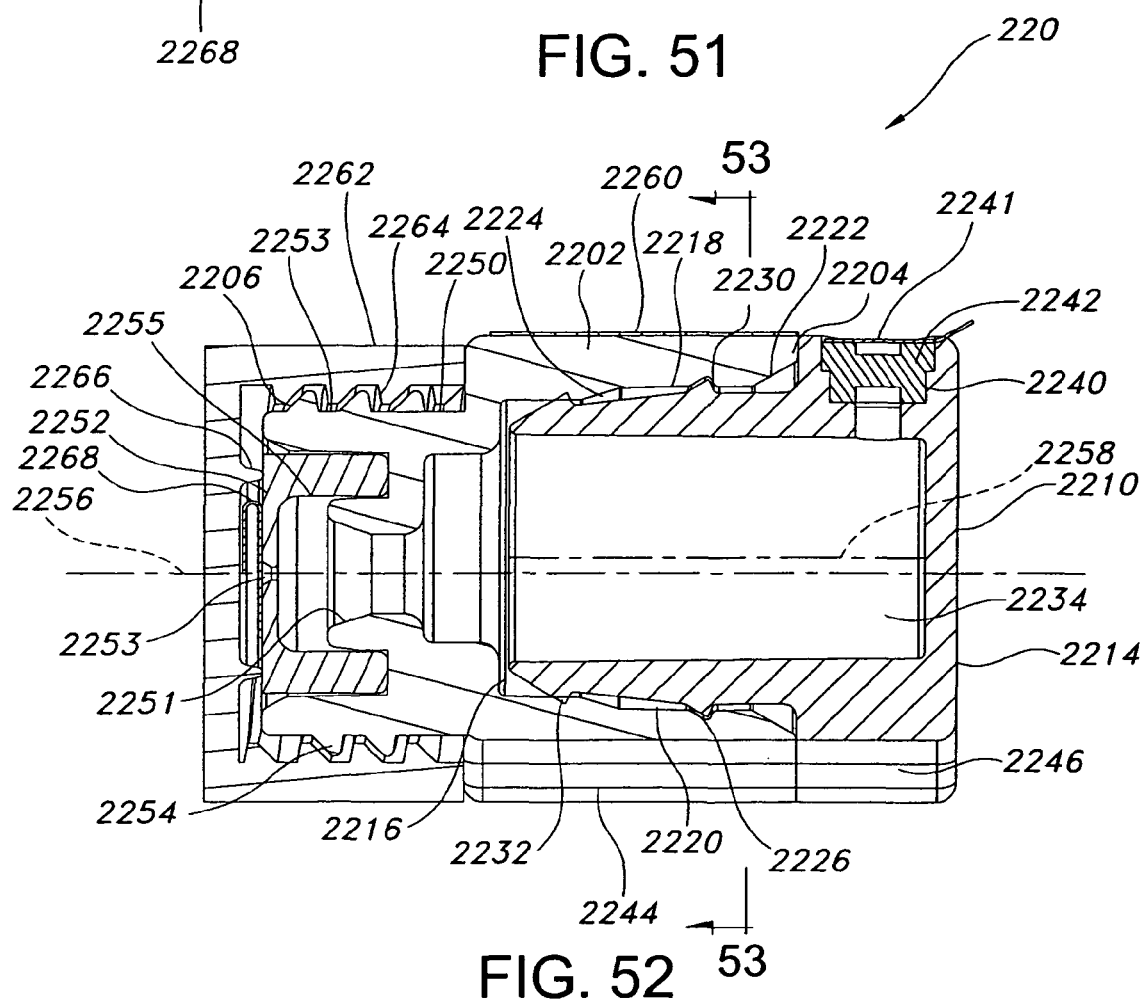
FIG. 52 is a side elevational view, in section, of the reservoir assembly of FIG. 51.

A reservoir assembly 220 according to an exemplary embodiment of the present invention is shown in FIGS. 51 and 52. Reservoir assembly 220 includes a generally cylindrical distal body portion 2202 having a proximal end 2204 and a distal end 2206 and a generally cylindrical proximal body portion 2210 having a proximal end 2214 and a distal end 2216. Body portions 2202, 2210 may be constructed from low density polyethylene, polypropylene, or some other suitable biocompatible material.

Proximal end 2204 of distal body portion 2202 includes a wall 2218 that defines a cavity 2220. Wall 2218 includes a proximal detent ring 2222 and a distal seal 2224 that both extend from wall 2218 into cavity 2220. Distal end 2216 of proximal body portion 2210 includes a wall 2226. Wall 2226 includes a proximal detent ring 2230 and a distal seal 2232 that both extend outwardly from wall 2226.

Wall 2226 is inserted into cavity 2220 such that detent ring 2222 and seal 2224 engage detent ring 2230 and seal 2232, respectively, locking distal body portion 2202 and proximal body portion 2210 together, defining a cavity 2234 having an inner portion. A fluid type is disposed within cavity 2234 and touches the inner wall defining cavity 2234. Fluid type may be water, one of a plurality of types of fluid, one of a plurality of types of diagnostic agents, antibiotics, corticosteroids, antibiotic/corticosteroid combinations, lubricants, tear substitutes, tear production enhancement agents, decongestants, antihistamines, decongestant/antihistamine combination agents, antibacterial agents, antiviral agents, antimicrobial agents, steroidal anti-inflammatory agents, antibiotic/steroidal anti-inflammatory combination agents, nonsteroidal anti-inflammatory agents, topical anesthetic agents, topical anesthetic/fluorescein combination agents, hypertonic saline solution, mydriatic/cycloplegics, miotics, ocular hypotensive agents (anti-glaucoma agents) including: miotics, alpha-adrenergic agents, carbonic anhydrase inhibitors, beta-blocking agents, prostaglandin analogs, combination agents, or one of any type of fluid that is pharmacologically compatible with the eye. The fluid in cavity 2234 comprises a therapeutic reactive agent and a liquid carrier. The viscosity of the fluid may be between about 0.7 and about 10 centipoise.

Proximal end 2214 of proximal body portion 2210 includes a vent 2240 in fluid communication with cavity 2234 and with atmosphere. Vent 2240 includes a generally annular vent cap 2242 extending between cavity 2234 and the atmosphere. Vent cap 2240 is constructed from a liquid impermeable/gas permeable material to allow make-up air to pass through liquid impermeable seal and into cavity 2234 upon discharge of fluid from cavity 2234. A vent cover 2241 is releasably disposed over vent cap 2240. Vent cover 2241 may be constructed from a laminate including medical grade adhesive tape made from a polyethylene or polyurethane film. Vent cover 2241 may be attached to vent cap 2240 by heat or by an adhesive such that vent cover 2241 is readily removed from vent cap 2240 prior to insertion of reservoir assembly 220 into device 200.

As shown in FIG. 52, walls 2218 and 2226 may each include a contour 2244, 2246, respectively, incorporated therewith. Contours 2244, 2246 may be a recess that extends inwardly toward cavity 2234, with contours 2244, 2246 shown in each of FIGS. 51 and 52, and contour 2246 shown in FIG. 53. Alternatively, contour may be a rib or other feature that extends outwardly from cavity 2234. Contour 2244 engages with a mating keyed surface contour 2608 on body 2606 to ensure that reservoir is properly inserted within device.

Contours 2244, 2246 may also correspond to the particular fluid type retained within cavity 2234. By way of example, contours 2244, 2246 for a first reservoir containing a saline solution may include a single longitudinal recess, whereas a second reservoir containing a diagnostic agent such as tropicamide may include more than one longitudinal recess, with the recesses aligned in a keyed relationship with keyed surface contour 2608 such that the first reservoir may only be inserted into a device 200 with a mating alignment feature that permits insertion of the first reservoir into device 200, but precludes insertion of second reservoir into device 200.

An aperture comprising a discharge port 2250 extends from distal end 2206 of distal body portion 2202 and is in fluid communication with cavity 2234. Discharge port 2250 is defined by an inner lip 2251 that extends distally from cavity 2234. Distal end 2206 of distal body portion 2202 also includes an outer lip 2253 that includes a male thread connection 2254. Thread connection 2254 mates with a disposable cap (not shown) that is threadedly coupled to reservoir assembly 220 prior to use. Cap is removed from reservoir assembly 220 prior to inserting reservoir assembly 220 into device 200.

A resealable gasket 2252 is attached to discharge port 2250. Gasket 2252 includes a proximal lip 2255 that is received and held between inner lip 2251 and outer lip 2253 of distal end 2206 of distal body portion 2202. Gasket 2252 may be a rubber gasket having a slit or a pin opening. FIG. 51 shows gasket 2252 having a pin opening 2253. Pin opening expands to facilitate insertion of proximal end 2110 of the lumen of the transducer 2104 through gasket 2252 into cavity 2234.

Gasket 2252 is in the closed position where reservoir 220 is not inserted into device 200 and proximal end 2110 of transducer 2104 is not inserted through opening 2253. When reservoir assembly 220 is inserted into device 200, proximal end 2110 of lumen of transducer 2104 engages gasket 2252 and penetrates opening 2253 such that proximal end 2110 of transducer 2104 fluidly communicates with cavity 2234. Gasket 2252 prevents leakage of fluid from cavity 2234 around transducer 2104.

Cavity 2234 is sized to contain a volume of approximately 1 milliliter of fluid within cavity 2234. This volume is sufficient to provide at least approximately 30 applications per reservoir assembly 220.

Referring to FIG. 52, reservoir assembly 220 includes two longitudinal axes 2256 and 2258. Aperture axis 2256 is a centerline for reservoir assembly 220 and extends through pin opening 2253. Cavity axis 2258 is a centerline for cavity 2234. As shown in FIG. 52, cavity axis 2258 extends closer to vent 2240 than aperture axis 2256.

Reservoir assembly 220 includes a label 2260 that provides information about the fluid disposed within reservoir assembly 220. Fluid is optimally an FDA-approved drug for ophthalmic applications and/or indications. Label 2260 may include such information as the proprietary name of the fluid, the established name of the fluid, if such established name exists, an identifying lot or control number, and the name of the manufacturer, packer, or distributor of the fluid. While reservoir 220 is shown in FIGS. 51, 52 to be constructed from components 2202 and 2210, those skilled in the art will recognize that these components of reservoir assembly 220 may be combined into a single component.

A removable reservoir cap 2262 may be threadably, releasably coupled to male thread connection 2254. Reservoir cap 2262 includes female threads 2264 that mate with male thread connection 2254. Reservoir cap 2262 also includes an annular seal 2266 that engages gasket 2252 to help seal opening 2253 when reservoir assembly 220 is not inserted into device 200, such as during transport. A reservoir gasket cover 2268 is inserted into an interior of reservoir cap 2262 within annular seal 2266 to further seal opening 2253. Gasket cover 2268 is attached to reservoir cap 2262, such as with adhesive, such that gasket cover 2268 remains with reservoir cap 2262 when reservoir cap 2262 is removed from reservoir assembly 220. Reservoir cap 2262 may be constructed from polyethylene, polypropylene, or some other suitable biocompatible material. Filling of reservoir assembly 220 may be performed in a sterile environment in accordance with 21 C.F.R. Parts 210-226.

Operation of device 200 is as follows. A method of delivering an ophthalmic fluid using ophthalmic fluid delivery device 200 comprises the steps of moving at least one shutter 2428 with respect to aperture 2411 of nozzle 2402 of ophthalmic fluid delivery device 200 from a closed position at least partially covering aperture 2411 toward an open position permitting flow of the ophthalmic fluid through aperture 2411 and discharging ophthalmic fluid through aperture 2411 of nozzle 2402 of ophthalmic fluid delivery device 200. The method optionally also comprises moving plural shutters 2428 with respect to aperture 2411 of nozzle 2402. The method further optionally comprises moving shutter actuator 2440 and rotating shutter actuator 2440 with respect to nozzle 2402.

Another method of delivering an ophthalmic fluid from ophthalmic fluid delivery device 200, having handle axis 2508 and discharge axis 2412, comprises the steps of orienting discharge axis 2412 between about 105 degrees and 125 degrees from handle axis 2508 and discharging the ophthalmic fluid along discharge axis 2412. The method optionally also comprises orienting discharge axis 2412 between about zero degrees and about 10 degrees from a horizontal axis.

Still another method of preparing ophthalmic fluid delivery device 200 to deliver an ophthalmic fluid comprises the steps of inserting reservoir 220 containing the ophthalmic fluid into cavity 2606 defined by ophthalmic fluid delivery device 200 and visualizing label 2260 on reservoir 220 through aperture 2719 defined by ophthalmic fluid delivery device 200. The method optionally further comprises visualizing label 2260 through a substantially transparent window 2720.

Another method of preparing ophthalmic fluid delivery device 200 to deliver an ophthalmic fluid comprises the steps of selecting a reservoir 220 containing the ophthalmic fluid from among a group of reservoirs containing a group of ophthalmic fluids and inserting reservoir 220 into cavity 2606 of ophthalmic fluid delivery device 200 such that contour 2244, 2246 on reservoir 220 aligns with contour 2608 of cavity 2606, thereby maintaining reservoir 220 in a predetermined alignment and preventing an alignment other than the predetermined alignment. The method optionally further comprises rejecting a reservoir 220 having a contour 2244, 2246 that does not align with the contour 2608 of cavity 2606.

Yet another method of preparing ophthalmic fluid delivery device 200 to deliver an ophthalmic fluid comprises the steps of switching ophthalmic fluid delivery device 200 from an "off" position to an "on" position and performing at least one of the following steps: opening aperture 2411 of ophthalmic fluid delivery device 200 to permit flow of ophthalmic fluid therethrough; opening venturi passage 2422 defined by ophthalmic fluid delivery device 200 to permit flow of air through aperture 2411 with the ophthalmic fluid; or activating an indicator 2637 to indicate that ophthalmic fluid delivery device 200 is ready to deliver the ophthalmic fluid. The latter steps are optionally performed separately or together in conjunction with the step of switching ophthalmic fluid delivery device 200 from an "off" position to an "on" position. The steps are also optionally all performed substantially simultaneously.

An operator determines an ophthalmic indication for which treatment is required and selects device 200 having keyed surface contour 2608 in cradle 2606 that corresponds to corresponding contour 2244, 2246 in a reservoir assembly 220 covering treatment of the indication.

Operator removes top housing assembly 270 from remainder of device 200 by sliding top housing assembly 270 proximally relative to device 200. Operator inserts reservoir assembly 220 into cradle 2606 such that contours 2244, 2246 in reservoir assembly 220 align with keyed surface contour 2608 in cradle 2606. Additionally, reservoir assembly 220 is slid distally such that proximal transducer end 2110 is inserted through gasket 2252, bringing fluid in cavity 2234 into fluid communication with transducer lumen 2112.

Top housing assembly 270 is reinserted onto device 200 by sliding locking rails 2710 distally under respective base rails 2612 until knob 2714 seats in respective notch 2618, releasably retaining top housing assembly 270 onto body 260. Operator is able to view and read indicia on label 2260 through aperture 2719 and window 2720 in top housing assembly 270 to ensure that the proper name of the fluid is visible through aperture 2719.

Operator grips device 200 by handle assembly 250 and grips device 200 simulating the holding of a gun. With a free hand, operator grips nosecone assembly 280 and rotates nosecone assembly 280 in a counterclockwise direction looking from distal end 2602 of body 260. Nosecone assembly 280 rotates approximately 60 degrees relative to body 260. Rotation of nosecone assembly 280 performs four (4) functions:

1) Rotation of nosecone assembly 280 rotates shutter actuator 2440, which in turn pivots shutters 2428 about their respective shutter pins 2434, moving shutters 2428 from a closed position to an open position. In the closed position, the longer sides of each shutter 2428 abut each other, closing aperture 2411. When rotated to the open position, the longer sides of shutters 2428 pivot away from each other, opening aperture 2411 and allowing flow through nozzle passage 2410.

2) Rotation of nosecone assembly 280 transmits an electrical signal through PCB 2520 to LEDs 2637, lighting LEDs 2637. Light from LEDs 2637 is transmitted through nosecone lens 2802, which acts as a light pipe to illuminate distal end of nose cone lens 2802 and provide a visual indication to operator that device 200 is ready for operation.

3) Rotation of nosecone assembly 280 also activates arming switch 2542 on PCB 2520, enabling operation of device 200.

4) Finally, rotation of nosecone assembly 280 rotates venturi cut-outs 2846 to fluidly communicate with venturi openings 2422 in nozzle 2402, providing fluid communication into nozzle passage 2410 from atmosphere.

With a free hand, operator next grips spacer assembly 290 and extends spacer assembly 290 from body 260 by pulling extension 2904 distally along extension slider 2908 a desired distance. Operator places distal face piece 2930 against inferior orbital rim of eye that is being treated. Desirably, axis 2412 is between about zero (0) degrees and about ten (10) degrees from the horizontal axis. Operator then pulls activation switch 2514. Operation of activation switch 2514 transmits a signal through PCB 2520 to transducer assembly 210, exciting piezoelectric device 2152, and generating longitudinal vibration of transducer 2104, which in turn transmits fluid from cavity 2234 into transducer lumen 2112.

Fluid travels through lumen 2112 and to mesh plate 2320. Mounting of mesh plate 2320 on mesh spring 2302 allows mesh plate 2320 to oscillate with lumen transducer 2104. Fluid is transmitted through openings in mesh plate 2320 and into nozzle passage 2410. Passage of fluid through passage 2410 generates a venturi effect within venturi openings 2422, which draws air from external to device 200 through venturi cutouts 2846 in nosecone assembly 280, into venturi openings 2422 and into passage 2410, where air is entrained into fluid, generating a mist.

Figures 53, 54:
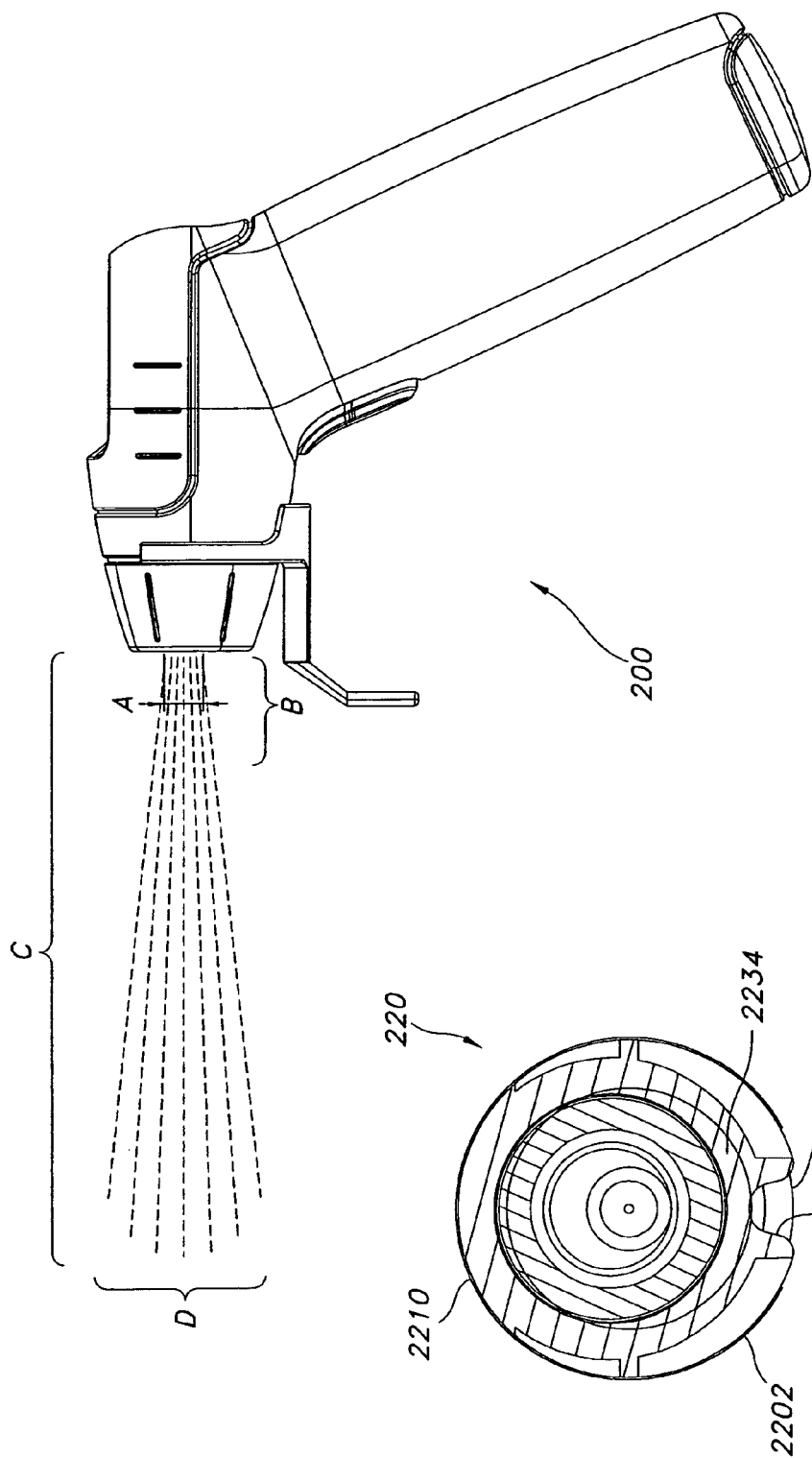
FIG. 53 is a transverse sectional view of the reservoir assembly taken along lines 53—53 of FIG. 52.
FIG. 54 is a side elevational view of an exemplary device according to the present invention generating a mist of fluid.

Mist exits aperture 2411 and exits distal end 202 of device 200 as shown in FIG. 54. As show in FIG. 54, mist forms a plume having an initial diameter or thickness "A" of approximately 7 millimeters that extends for a distance "B" of approximately 20 millimeters. Total mist length extends for a distance "C" of approximately 100 millimeters and expands to a diameter "D" of approximately 34 millimeters. Mist may be dispensed as a single plume, as shown in FIG. 54. Alternatively, mist may be generated in a series of pulses.

Activation of activation switch 2514 transmits a signal to transducer assembly 210 to operate transducer assembly 210, but does not determine the length of time that transducer assembly 210 is operated. Duration of operation of transducer assembly 210 is independent of duration of activation of activation switch 2514, and dependent upon setting of mist timer 3300.

Activation of activation switch 2514 also transmits a signal to PCB 2520 to blink LED's 2637 in an on/off pattern while transducer assembly 210 is operating. When transducer assembly 210 ceases operation, a signal is sent to LED's 2637 to provide constant illumination.

After operator dispenses the mist into the eye of a patient, operator rotates nosecone assembly 280 approximately 60 degrees clockwise looking from distal end 202 of device 200. Such rotation disarms arming switch 2542, disabling device 200 regardless of whether activation switch 2514 is depressed. The rotation of nosecone assembly 280 also shuts off power supply to LEDs 2627. Rotation also pivots shutters 2428 about their respective pivot pins 2426 such that shutters 2428 close off aperture 2411. Rotation of nosecone assembly 280 also closes venturi openings 2422, preventing-flow of air from external to device 200 through venturi openings 2422 and into nozzle passage 2408.

Without limitation to any particular theory or hypothesis, it is believed that the blink reflex, when triggered in response to contacting the eye with a mist, is dependent at least in part on the momentum at which such a mist contacts the eye. Such mist momentum is based, at least in part, on the mass of the mist particles and the velocity of those particles. Therefore, the velocity and mass (perhaps in terms of particle size) of the mist contributes to the blink reflex. The benefit of delivering a low momentum fluid infusion to the eye is that the ocular defenses of blinking (blepharospasm) and tearing (lacrimation), which seek to rid the eye of a foreign substance, are not stimulated to the degree that would result from a high momentum infusion, such as by delivery of an eye drop to the eye. There is therefore a longer residence time on the eye, allowing for enhanced efficacy. The low momentum infusion comes in "under the radar" and is therefore not expelled as quickly and efficiently by the eye's defenses. It is also believed that an additional benefit of the present invention accrues with regard to less medication subject to systemic absorption (via the lacrimal drainage apparatus) and, therefore, less likelihood of systemic side effects.

In an exemplary embodiment of the present invention, in order to deliver mist at a level subliminal to the blink reflex, transducer 2104 is configured to transport ophthalmic fluid at a velocity less than about 2.5 meters per second and with a particle size less than about 15 microns.

It is also believed that the flow characteristics of the plume can be a factor in the efficacy of the mist therapy. Accordingly, transducer 2104 is optionally configured to transport ophthalmic fluid in a plume having substantially laminar flow characteristics for at least about 2 cm from the transducer 2104 and up to at least about 8 cm from the transducer 2104. The plume optionally has transitional flow characteristics blending from laminar flow to turbulent flow from about 2 cm to about 4 cm from the transducer 2104. The plume may become mostly turbulent and increasingly divergent beyond about 4 cm from the transducer 2104.

It is further believed that the flow rate of the ophthalmic fluid in the plume can be a factor in the efficacy of the mist therapy. Accordingly, transducer 2104 may also be configured to transport a discharge of about 3 microliters per second of the ophthalmic fluid. Transducer 2104 may optionally be configured to transport the ophthalmic fluid at a flow rate of about 1 to about 3 microliters per second, and at a flow rate of about 2 microliters per second. Transducer 2104 may also be configured to transport the ophthalmic fluid for about 1 to about 2 seconds, and for about 1½ seconds.

The frequency at which the transducer becomes resonant is a factor in the performance of the mist delivery device. Accordingly, transducer 2104 may be configured to be resonant at about 175 to about 190 kHz and may be optionally configured to be resonant at about 180 to about 185 kHz. The resonant frequency of transducer 2104 is directly related to its geometry. The length of transducer 2104 is a multiple of the wavelength of the frequency in the transducer material. Transducer geometry is configured to amplify the vibrations imparted by the piezo device 2152, so that the maximum energy is present at the distal transducer tip 2108, next to mesh plate 2320.

It is also believed that the flow divergence of the plume can be a factor in the efficacy of the mist therapy. Accordingly, the nozzle 2402 may be configured to generate a plume divergent at an angle of about 2 to about 5 degrees inclusive. Aperture 2411 of nozzle 2402 may have an inside diameter of between about 5 mm and about 6 mm.

The mist that is generated from device 200 as shown in FIG. 54 exits device 200 having a velocity of between about 50 centimeters per second and about 140 centimeters per second. Flow rate of the mist is between about 1.5 microliters per second and about 3 microliters per second, with particle size having a Sauter Mean diameter (D32) of between about 5 microns and about 15 microns.

Discharge period of the mist from device 200 is between about 0.5 seconds and about 2 seconds. Transducer 2104 oscillates at a frequency of between about 180 kilohertz and about 185 kilohertz to dispense fluid from lumen 2112. Without limitation to any particular theory of operation, it is believed that the dispensed liquid is replaced in lumen 2112 by capillary force.

A total volume of between about 2 microliters and about 5 microliters per operation is discharged from device 200 as a result of each activation of activation switch 2514.

As the mist exits distal end 202 of device 200, mist is formed in a tight columnar plume with laminar flow characteristics for about the first two centimeters distal of distal end 202. Nozzle length and air entrained within fluid as a result of venturi effect are attributed to formation of these laminar flow characteristics. Flow characteristics are transitional from about two (2) centimeters to about four (4) centimeters distal of distal end 202, with mist plume flow becoming mostly turbulent and increasingly divergent beyond about four (4) centimeters from distal end 202 of device 200. The transitional phase between about two (2) centimeters and about four (4) centimeters diverges at a divergence angle of between about two (2) degrees and about five (5) degrees. At four (4) centimeters from distal end 202 of device 200, plume divergence angle increases rapidly.

The mist transmitted to the eye is optionally delivered to the corneal surface of the eye in a therapeutic amount subliminal to both the blink reflex and the lacrimal reflex of the patient. Mist particle size, total volume of mist to the corneal surface, the delivering time period, and the velocity of the mist are all factors that are to be considered in the generation of the mist subliminal to the blink and lacrimal reflexes.

According to another exemplary aspect of this invention, a method for delivering an ophthalmic fluid to an eye of a patient for ophthalmic therapy is provided according to an embodiment of the present invention. The method comprises generating a mist from an ophthalmic fluid including a therapeutic amount of a therapeutically active agent and a liquid carrier. The method also includes directing the mist toward the corneal surface of the eye of the patient in the form of a plume having finely divided droplets with a particle size in the range of about 7 microns to about 10 microns mean diameter and a velocity in the range of about 0.4 meters/second to about 2.5 meters/second. The method also includes delivery of the mist for a duration of about 0.5 seconds to about 2 seconds per application, including a duration of about 0.7 second to about 1.5 seconds per application, and a duration of about 1 second to about 1.5 seconds per application.

The method, according to one exemplary aspect, also includes maintaining the particle size and the velocity such that the blink reflex of the eye to which the delivery is made is not triggered by introduction of the mist into the eye and such that the lacrimal reflex of the eye to which the delivery is made is also not triggered by introduction of the mist into the eye. The method also comprises delivering the mist at a rate of about 1 to about 5 microliters (μl) per second. The method also comprises generating a mist from an ophthalmic fluid having a viscosity of about 0.5 to about 10 centipoise (cps), more preferably including an ophthalmic fluid having a viscosity of about 0.75 to about 5 centipoise (cps), and most preferably including an ophthalmic fluid having a viscosity of about 1 centipoise (cps).

A method for delivering a dosage of an ophthalmic fluid to an eye of a patient for ophthalmic therapy according to an embodiment of the present invention comprises generating a mist from an ophthalmic fluid including a therapeutic amount of a therapeutically active agent and a liquid carrier and directing the mist toward the corneal surface of the eye of the patient in the form of a plume in a plurality of pulses, each of the pulses having a duration less than about 2 seconds. The method preferably includes directing the mist in a plurality of pulses, each of the pulses having a duration less than about 1.5 seconds, and most preferably each of the pulses having a duration of about 1 second to about 1.5 seconds.

According to another exemplary aspect of the invention, a method is provided for treating an ophthalmic condition with an ophthalmic fluid according to an embodiment of the present invention. The method comprises generating a mist from an ophthalmic fluid including a therapeutic amount of a therapeutically active agent and a liquid carrier and applying the mist to the corneal surface of the eye of the patient in a volume not exceeding about 30 microliters. The method preferably includes directing the plume in a volume not exceeding about 20 microliters and more preferably directing the plume in a volume not exceeding about 10 microliters. The method most preferably includes directing the plume in a volume of about 6 microliters.

According to yet another exemplary aspect of the invention, a method is provided for treating an ophthalmic condition using an ophthalmic fluid by generating a mist from an ophthalmic fluid including a therapeutic amount of a therapeutically active agent and a liquid carrier and applying the mist toward the corneal surface of the eye of the patient in a plurality of pulses, each of the pulses having a duration less than about 2 seconds, including preferred pulses having a duration less than about 1.5 seconds, and including more preferred pulses having a duration of about 1 second to about 1.5 seconds.

In addition to all other treatments and indications in which ophthalmic fluids are administered to the ocular region of a patient, it is believed that the mist generated by device 100, 200 may be particularly effective in the treatment of blepharitis, which is an inflammation of the eyelids which can result from infections, allergies, skin conditions such as seborrhea and rosacea, chemicals and other irritants. The inventors believe that fine particles containing anti-inflammatory medication (corticosteroid derivatives, for example) and antibiotic medication are more likely to be deposited at the lash roots and lid margins (where there are many inflamed and occluded gland orifices) than the currently used medication vehicle (ointment).

Although device 100, 200 may be primarily used in ophthalmic applications, it is also capable of effective use in treating dermatologic conditions. It is believed that certain skin conditions, such as eczema, herpes simplex dermatitis, impetigo, psoriasis, burns, and abrasions, where frequent "thin film" applications of medicated mist generated by device 100, 200 may effectively deliver medication to the desired site, can also be effectively treated using a device such as device 100, 200.

Additionally, it is contemplated that device 100, 200 can be used as a vehicle for the application of "cosmeceuticals", a relatively new hybrid class of "medicaments" that are both therapeutic to a degree and also promote better skin health and appearance (smoother skin, fewer wrinkles, etc.).

It is also believed that device 100, 200 can be used effectively to deliver "nanopackaged" drugs and/or cosmeceuticals (liposomes, dendrimeres, nanotubes, etc.) that may be delivered via a mist. It is believed that the combined effect of increasing total surface area of the medication or other fluid by many orders of magnitude while allowing for enhanced penetration due to small particle size may improve pharmacodynamics considerably.

Additionally, it is also contemplated that device 100, 200 may be used for ear, nose, and throat applications, such as in the treatment of otitis externa and otitis media, as well as systemic drug delivery (e.g., insulin and other hormones, etc.). Also, those skilled in the art will recognize that the embodiments of the present invention may alternatively be used with a respiratory fluid instead of an ophthalmic fluid, and that the invention may be used in the treatment of respiratory ailments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An ophthalmic fluid delivery device adapted to deliver an ophthalmic fluid in the form of a mist to an ocular region of a patient from a reservoir containing the ophthalmic fluid, the ophthalmic fluid delivery device comprising:
   a body defining a cavity sized to accommodate a reservoir;
   a reservoir connected to said body and disposed within said cavity, wherein said reservoir contains an ophthalmic fluid disposed therein;
   propulsion means for transmitting said ophthalmic fluid from said reservoir to a discharge plate, wherein transmission of said ophthalmic fluid across said discharge plate generating a plume of ophthalmic fluid along a direction directly toward said eye;
   a nozzle assembly coupled to said body proximate said cavity, said nozzle assembly being configured to deliver said plume directly along a direction directly toward said eye, wherein said plume of ophthalmic fluid travels, without being subject to a dynamic force generated by a mechanical device of said ophthalmic fluid delivery system that is physically separate from said propulsion means, from said discharge plate to said eye and at said eye has a momentum that has a magnitude that is insufficient to trigger at least one of an ocular blink reflex and a lacrimation reflex of said eye; and
   an aperture defined by said body adjacent said cavity defined by said body, said aperture being positioned to permit visualization of said reservoir from outside said body when said reservoir is positioned within said cavity of said body;
   wherein the body comprises a proximal end and a distal end;
   the discharge plate is disposed at the distal end;
   the discharge plate includes a plurality of openings extending therethrough;
   the aperture comprises a window;
   the window is substantially translucent or transparent;
   the ophthalmic fluid is discharged from the discharge plate at a velocity of between approximately 4 and 30 centimeters per second;
   the ophthalmic fluid is discharged from the discharge plate at a rate of between approximately 2 and 10 microliters per second; and
   the ophthalmic fluid discharged from the discharge plate has average particle sizes between approximately 0.5 and 10 microns in diameter.

2. The ophthalmic fluid delivery device according to claim 1, said body having a door movable to an open position to facilitate access to said cavity.

3. The ophthalmic fluid delivery device according to claim 2, said door being slidably movable with respect to said cavity.

4. The ophthalmic fluid delivery device according to claim 2, said door being removable from said body.

5. The ophthalmic fluid delivery device according to claim 2, said aperture being defined by said door.

6. The ophthalmic fluid delivery system according to claim 1, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

7. The ophthalmic fluid delivery system according to claim 6, wherein the glaucoma medications are selected from the group consisting of prestaglandins, beta blockers, alpha adrenergic agents, carbonic anhydrase inhibitors, and miotics.

8. The ophthalmic fluid delivery system according to claim 1, wherein the plume of ophthalmic fluid has a volume that can entirely be retained by the eye.

9. The ophthalmic fluid delivery system of claim 1, wherein the plume of ophthalmic fluid contains an amount of ophthalmic medicine and the momentum of the plume is such that substantially all of the amount of ophthalmic medicine is received and retained by the human eye.

10. The ophthalmic fluid delivery device according to claim 1, wherein said substantially translucent or transparent window comprises volume graduation markings.

11. The ophthalmic fluid delivery device according to claim 1, further comprising a label affixed to said substantially translucent or transparent window.

12. The ophthalmic fluid delivery device according to claim 11, wherein indicia is included on said label, wherein said indicia is selected from the group consisting of company name, logo and color coding.

* * * * *